United States Patent [19]
Dickson, Jr. et al.

[11] Patent Number: 5,827,875
[45] Date of Patent: Oct. 27, 1998

[54] INHIBITORS OF MICROSOMAL TRIGLYCERIDE TRANSFER PROTEIN AND METHOD

[75] Inventors: John K. Dickson, Jr., Eastampton, N.J.; Jeffrey A. Robl, Newtown, Pa.; Scott A. Biller, Hopewell, N.J.

[73] Assignee: Bristol-Myers Squibb Company, Princeton, N.J.

[21] Appl. No.: 842,132

[22] Filed: Apr. 23, 1997

[51] Int. Cl.$^6$ .................. A61K 31/40; C07D 207/26
[52] U.S. Cl. .................. 514/424; 548/528; 548/518; 548/550; 548/557; 514/422; 514/426
[58] Field of Search ..................... 548/528, 550, 548/557, 518, 525, 527; 514/422, 424, 426

[56] References Cited

U.S. PATENT DOCUMENTS

| | | | |
|---|---|---|---|
| 3,910,931 | 10/1975 | Cavalla et al. | 260/293.62 |
| 3,963,745 | 6/1976 | Cale, Jr. et al. | 260/326.55 |
| 4,289,781 | 9/1981 | Bengtsson et al. | 424/267 |
| 4,367,232 | 1/1983 | Boix-Igleasias et al. | 424/267 |
| 4,576,940 | 3/1986 | Tahara et al. | 514/212 |
| 4,581,355 | 4/1986 | Tahara et al. | 514/212 |
| 4,607,042 | 8/1986 | Pierce | 514/323 |
| 4,826,975 | 5/1989 | Picciola et al. | 544/391 |
| 5,026,858 | 6/1991 | Vega-Noverola et al. | 546/224 |
| 5,028,616 | 7/1991 | Desai et al. | 514/321 |
| 5,032,598 | 7/1991 | Baldwin et al. | 514/318 |
| 5,098,915 | 3/1992 | Desai et al. | 514/324 |
| 5,130,333 | 7/1992 | Pan et al. | 514/460 |
| 5,189,045 | 2/1993 | Peglion et al. | 514/319 |
| 5,212,182 | 5/1993 | Musser et al. | 514/314 |
| 5,215,989 | 6/1993 | Baldwin et al. | 514/252 |
| 5,292,883 | 3/1994 | Martin et al. | 546/201 |
| 5,527,801 | 6/1996 | Masuda et al. | 514/255 |

FOREIGN PATENT DOCUMENTS

| | | |
|---|---|---|
| 0584446A2 | 3/1994 | European Pat. Off. . |
| 0643057A1 | 3/1995 | European Pat. Off. . |
| WO93/05778 | 4/1993 | WIPO . |
| WO96/40640 | 12/1996 | WIPO . |

OTHER PUBLICATIONS

Bulleid & Freedman, Nature 335, 649–651 (1988). "Defective co–translational formation of disulphide bonds in protein disulphideisomerase–deficient microsomes".

Koivu et al., J. Biol. Chem. 262, 6447–6449 (1987). "A Single Polypeptide Acts both as the β Subunit of Prolyl 4–Hydroxylase and as a Protein Disulfide–Isomerase".

Kane & Havel in the Metabolic Basis of Inherited Disease, Sixth Edition, 1139–1164 (1989). "Disorders of the Biogenesis and Secretion of Lipoproteins Containing the B Apolipoproteins".

Schaefer et al., Clin. Chem. 34, B9–B12 (1988). "Genetics and Abnormalities in Metabolism of Lipoproteins".

Drayna et al., Nature 327, 632–634 (1987). "Cloning and sequencing of human cholesteryl ester transfer protein cDNA".

Pihlajaniemi et al., EMBO J. 6, 643–649 (1987). "Molecular cloning of the β–subunit of human prolyl–4–hydroxylase. This subunit and protein disulphide isomerase are products of the same gene".

Yamaguchi et al., Biochem. Biophys. Res. Comm. 146, 1485–1492 (1987). "Sequence of Membrane–Associated Thyroid Hormone Binding Protein From Bovine Liver: Its Identity with protein Disulphide Isomerase".

Edman et al., Nature 317, 267–270 (1985). Sequence of protein disulphide isomerase and implications of its relationship to thioredoxin.

Kao et al., Connective Tissue Research 18, 157–174 (1988). "Isolation of cDNA Clones and Genomic DNA Clones of β–Subunit of Chicken Prolyl 4–Hydroxylase".

Wetterau, J. et al., Biochem 30, 9728–9735 (1991). "Protein Disulfide Isomerase Appears Necessary To Maintain the Catalytically Active Structure of the Microsomal Triglyceride Transfer Protein".

Morton, R.E. et al., J. Biol. Chem. 256, 1992–1995 (1981). "A Plasma Inhibitor of Triglyceride and Chloesteryl Ester Transfer Activities".

Wetterau, J. et al., Biochem. 30, 4406–4412 (1991). "Structural Properties of the Microsomal Triglyceride–Transfer Protein Complex".

Wetterau, J. et al., J. Biol. Chem. 265, 9800–9807 (1990). "Protein Disulfide Isomerase Is a Component of the Microsomal Triglyceride Transfer Protein Complex".

Wetterau, J. and Zilversmit, D.B., Chem. and Phys. of Lipids 38, 205–22 (1985). "Purification and Characterization of Microsomal Triglyceride and Cholesteryl Ester Transfer Protein From Bovine Liver Microsomes".

(List continued on next page.)

Primary Examiner—John Kight
Assistant Examiner—Charanjit S. Aulakh
Attorney, Agent, or Firm—Burton Rodney

[57] ABSTRACT

Compounds are provided which inhibit microsomal triglyceride transfer protein and thus are useful for lowering serum lipids and treating atherosclerosis and related diseases. The compounds have the structure

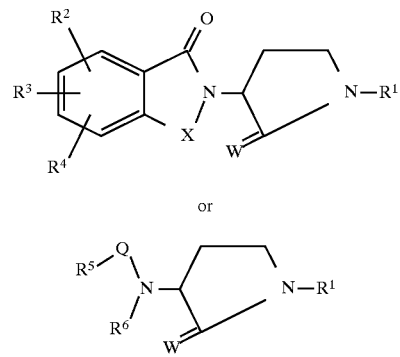

wherein $R^1$ to $R^6$, Q, W and X are as defined herein.

16 Claims, No Drawings

OTHER PUBLICATIONS

Wetterau, J. and Zilversmit, D.B., Biochimica et Biophysica Acta 875, 610–617 (1986). "Localization of intracellular triacylglycerol and cholesteryl ester transfer activity in rat tissues".

Wetterau, J. and Zilversmit, D.B., J. Biol. Chem. 259, 10863–10866 (1984). "A Triglyceride and Cholesteryl Ester Transfer Protein Associated with Liver Microsomes".

Wetterau, J., Grant Application entitled: "Intracellular Tryglyceride Transport and Metabolism".

Presentation Materials, Aspen Bile Acid/Cholesterol Conference, Aug. 15, 1992.

Wetterau, J. R., et al., Science, vol. 258, 999–1001, Nov. 6, 1992, "Absence of Microsomal Triglyceride Transfer Protein in Individuals with Abetalipoproteinemia".

Archibald, J. L., et al., Journal of Medicinal Chemistry, vol. 14, No. 11, pp. 1054–1059 (1991).

Cortizo, L. et al., J. Med. Chem., 34, pp. 2242–2247, 1991.

Hall, I. H. et al., Pharmaceutical Research, vol. 9, No. 10, pp. 1324–1329, 1992.

Hall, I. H., et al., Pharmacological Research Communications, vol. 19, No. 12, pp. 839–858, 1987.

Murthy et al., Eur. J. Med. Chem.–Chim. Ther., vol. 20, No. 6, pp. 547–550, 1985.

INHIBITORS OF MICROSOMAL TRIGLYCERIDE TRANSFER PROTEIN AND METHOD

FIELD OF THE INVENTION

This application is based on provisional application No. 60/017,253 filed May 10, 1996.

This invention relates to novel compounds which inhibit microsomal triglyceride transfer protein, and to methods for decreasing serum lipids and treating atherosclerosis employing such compounds.

BACKGROUND OF THE INVENTION

The microsomal triglyceride transfer protein (MTP) catalyzes the transport of triglyceride (TG), cholesteryl ester (CE), and phosphatidylcholine (PC) between small unilamellar vesicles (SUV). Wetterau & Zilversmit, *Chem. Phys. Lipids* 38, 205–22 (1985). When transfer rates are expressed as the percent of the donor lipid transferred per time, MTP expresses a distinct preference for neutral lipid transport (TG and CE), relative to phospholipid transport. The protein from bovine liver has been isolated and characterized. Wetterau & Zilversmit, *Chem. Phys. Lipids* 38, 205–22 (1985). Polyacrylamide gel electrophoresis (PAGE) analysis of the purified protein suggests that the transfer protein is a complex of two subunits of apparent molecular weights 58,000 and 88,000, since a single band was present when purified MTP was electrophoresed under nondenaturing condition, while two bands of apparent molecular weights 58,000 and 88,000 were identified when electrophoresis was performed in the presence of sodium dodecyl sulfate (SDS). These two polypeptides are hereinafter referred to as 58 kDa and 88 kDa, respectively, or the 58 kDa and the 88 kDa component of MTP, respectively, or the low molecular weight subunit and the high molecular weight subunit of MTP, respectively.

Characterization of the 58,000 molecular weight component of bovine MTP indicates that it is the previously characterized multifunctional protein, protein disulfide isomerase (PDI). Wetterau et al., *J. Biol. Chem.* 265, 9800–7 (1990). The presence of PDI in the transfer protein is supported by evidence showing that (1) the amino terminal 25 amino acids of the bovine 58,000 kDa component of MTP is identical to that of bovine PDI, and (2) disulfide isomerase activity was expressed by bovine MTP following the dissociation of the 58 kDa–88 kDa protein complex. In addition, antibodies raised against bovine PDI, a protein which by itself has no TG transfer activity, were able to immunoprecipitate bovine TG transfer activity from a solution containing purified bovine MTP.

PDI normally plays a role in the folding and assembly of newly synthesized disulfide bonded proteins within the lumen of the endoplasmic reticulum. Bulleid & Freedman, *Nature* 335, 649–51 (1988). It catalyzes the proper pairing of cysteine residues into disulfide bonds, thus catalyzing the proper folding of disulfide bonded proteins. In addition, PDI has been reported to be identical to the beta subunit of human prolyl 4-hydroxylase. Koivu et al., *J. Biol. Chem.* 262, 6447–9 (1987). The role of PDI in the bovine transfer protein is not clear. It does appear to be an essential component of the transfer protein as dissociation of PDI from the 88 kDa component of bovine MTP by either low concentrations of a denaturant (guanidine HCl), a chaotropic agent (sodium perchlorate), or a nondenaturing detergent (octyl glucoside) results in a loss of transfer activity. Wetterau et al., *Biochemistry* 30, 9728–35 (1991). Isolated bovine PDI has no apparent lipid transfer activity, suggesting that either the 88 kDa polypeptide is the transfer protein or that it confers transfer activity to the protein complex.

The tissue and subcellular distribution of MTP activity in rats has been investigated. Wetterau & Zilversmit, *Biochem. Biophys. Acta* 875, 610–7 (1986). Lipid transfer activity was found in liver and intestine. Little or no transfer activity was found in plasma, brain, heart, or kidney. Within the liver, MTP was a soluble protein located within the lumen of the microsomal fraction. Approximately equal concentrations were found in the smooth and rough microsomes.

Abetalipoproteinemia is an autosomal recessive disease characterized by a virtual absence of plasma lipoproteins which contain apolipoprotein B (apoB). Kane & Havel in *The Metabolic Basis of Inherited Disease*, Sixth Edition, 1139–64 (1989). Plasma TG levels may be as low as a few mg/dL, and they fail to rise after fat ingestion. Plasma cholesterol levels are often only 20–45 mg/dL. These abnormalities are the result of a genetic defect in the assembly and/or secretion of very low density lipoproteins (VLDL) in the liver and chylomicrons in the intestine. The molecular basis for this defect has not been previously determined. In subjects examined, triglyceride, phospholipid, and cholesterol synthesis appear normal. At autopsy, subjects are free of atherosclerosis. Schaefer et al., *Clin. Chem.* 34, B9–12 (1988). A link between the apoB gene and abetalipoproteinemia has been excluded in several families. Talmud et al., *J. Clin. Invest.* 82, 1803–6 (1988) and Huang et al., *Am. J. Hum. Genet.* 46, 1141–8 (1990).

Subjects with abetalipoproteinemia are afflicted with numerous maladies. Kane & Havel, supra. Subjects have fat malabsorption and TG accumulation in their enterocytes and hepatocytes. Due to the absence of TG-rich plasma lipoproteins, there is a defect in the transport of fat-soluble vitamins such as vitamin E. This results in acanthocytosis of erythrocytes, spinocerebellar ataxia with degeneration of the fasciculus cuneatus and gracilis, peripheral neuropathy, degenerative pigmentary retinopathy, and ceroid myopathy. Treatment of abetalipoproteinemic subjects includes dietary restriction of fat intake and dietary supplementation with vitamins A, E and K.

In vitro, MTP catalyzes the transport of lipid molecules between phospholipid membranes. Presumably, it plays a similar role in vivo, and thus plays some role in lipid metabolism. The subcellular (lumen of the microsomal fraction) and tissue distribution (liver and intestine) of MTP have led to speculation that it plays a role in the assembly of plasma lipoproteins, as these are the sites of plasma lipoprotein assembly. Wetterau & Zilversmit, *Biochem. Biophys. Acta* 875, 610–7 (1986). The ability of MTP to catalyze the transport of TG between membranes is consistent with this hypothesis, and suggests that MTP may catalyze the transport of TG from its site of synthesis in the endoplasmic reticulum (ER) membrane to nascent lipoprotein particles within the lumen of the ER.

Olofsson and colleagues have studied lipoprotein assembly in HepG2 cells. Bostrom et al., *J. Biol. Chem.* 263, 4434–42 (1988). Their results suggest small precursor lipoproteins become larger with time. This would be consistent with the addition or transfer of lipid molecules to nascent lipoproteins as they are assembled. MTP may play a role in this process. In support of this hypothesis, Howell and Palade, *J. Cell Biol.* 92, 833–45 (1982), isolated nascent lipoproteins from the hepatic Golgi fraction of rat liver. There was a spectrum of sizes of particles present with varying lipid and protein compositions. Particles of high density lipoprotein (HDL) density, yet containing apoB, were found. Higgins and Hutson, *J. Lipid Res.* 25, 1295–1305 (1984), reported lipoproteins isolated from Golgi were consistently larger than those from the endoplasmic reticulum, again suggesting the assembly of lipoproteins is a progressive event.

Recent reports (Science, Vol. 258, page 999, 1992; D. Sharp et. al., Nature, Vol. 365, page 65, 1993) demonstrate that the defect causing abetalipoproteinemia is in the MTP gene, and as a result, the MTP protein. Individuals with abetalipoproteinemia have no MTP activity, as a result of mutations in the MTP gene, some of which have been characterized. These results indicate that MTP is required for the synthesis of apoB containing lipoproteins, such as VLDL, the precursor to LDL. It therefore follows that inhibitors of MTP would inhibit the synthesis of VLDL and LDL, thereby lowering VLDL levels, LDL levels, cholesterol levels, and triglyceride levels in animals and man.

Canadian Patent Application No. 2,091,102 published Mar. 2, 1994 (corresponding to U.S. application Ser. No. 117,362, filed Sep. 3, 1993 (file DC21b)) reports MTP inhibitors which also block the production of apoB containing lipoproteins in a human hepatic cell line (HepG2 cells). This provides further support for the proposal that an MTP inhibitor would lower apoB containing lipoprotein and lipid levels in vivo. This Canadian patent application discloses a method for identifying the MTP inhibitors

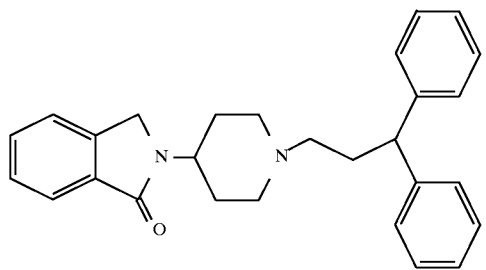

which has the name 2-[1-(3,3-diphenylpropyl)-4-piperidinyl]-2,3-dihydro-3-oxo-1H-isoindole hydrochloride and

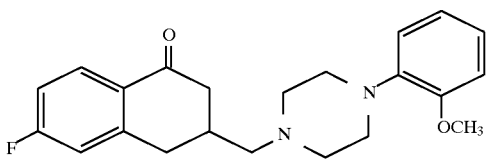

which has the name 1-[3-(6-fluoro-1-tetralanyl)methyl]-4-O-methoxyphenyl piperazine EP 0643057A1 published Mar. 15, 1995, discloses MTP inhibitors of the structure

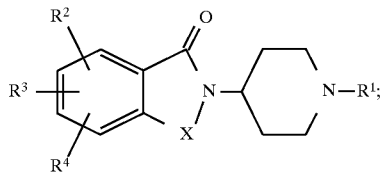

or

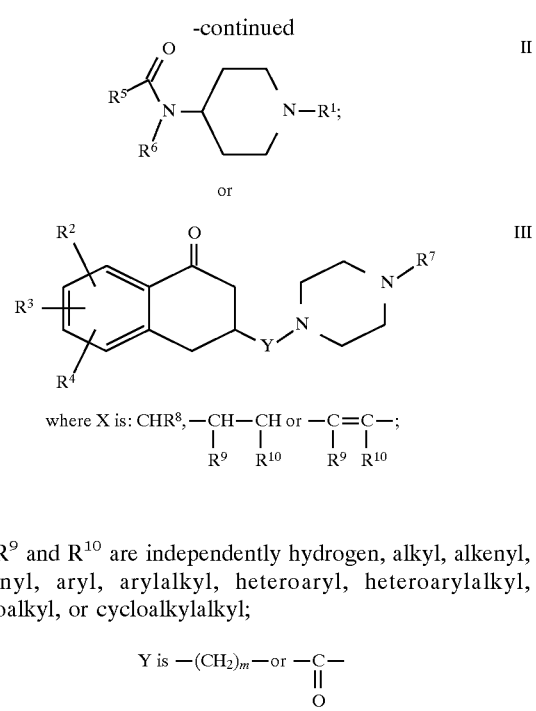

where X is: $CHR^8$, $-\underset{R^9}{CH}-\underset{R^{10}}{CH}-$ or $-\underset{R^9}{C}=\underset{R^{10}}{C}-$;

$R^8$, $R^9$ and $R^{10}$ are independently hydrogen, alkyl, alkenyl, alkynyl, aryl, arylalkyl, heteroaryl, heteroarylalkyl, cycloalkyl, or cycloalkylalkyl;

$$Y \text{ is } -(CH_2)_m- \text{ or } -\underset{\underset{O}{\|}}{C}-$$

where m is 2 or 3;

$R^1$ is alkyl, alkenyl, alkynyl, aryl, heteroaryl, arylalkyl (wherein alkyl has at least 2 carbons), diarylalkyl, arylalkenyl, diarylalkenyl, arylalkynyl, diarylalkynyl, diarylalkylaryl, heteroarylalkyl (wherein alkyl has at least 2 carbons), cycloalkyl, or cycloalkylalkyl (wherein alkyl has at least 2 carbons); all of the aforementioned $R^1$ groups being optionally substituted through available carbon atoms with 1, 2, or 3 groups selected from halo, haloalkyl, alkyl, alkenyl, alkoxy, aryloxy, aryl, arylalkyl, alkylmercapto, arylmercapto, cycloalkyl, cycloalkylalkyl, heteroaryl, fluorenyl, heteroarylalkyl, hydroxy or oxo; or $R^1$ is a group of the structure

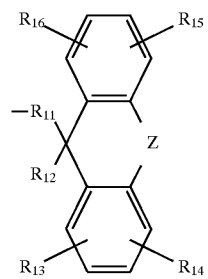

$R^{11}$ is a bond, alkylene, alkenylene or alkynylene of up to 6 carbon atoms, arylene (for example

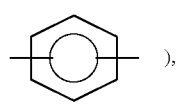 ), or mixed arylene-alkylene (for example

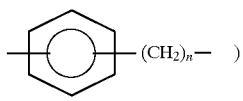
)

where n is 1 to 6;

$R^{12}$ is hydrogen, alkyl, alkenyl, aryl, heteroaryl, haloalkyl, arylalkyl, arylalkenyl, cycloalkyl, aryloxy, alkoxy, arylalkoxy, heteroarylalkyl or cycloalkylalkyl;

Z is a bond, O, S, N-alkyl, N-aryl, or alkylene or alkenylene of from 1 to 5 carbon atoms;

$R^{13}$, $R^{14}$, $R^{15}$, and $R^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, arylsulfonyl, alkylthio, arylthio, carboxy, aminocarbonyl, alkylcarbonyloxy, alkylcarbonylamino, arylalkyl, heteroaryl, heteroarylalkyl, or aryloxy;

or $R^1$ is

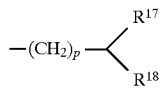

wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl, at least one of $R^{17}$ and $R^{18}$ being other than H;

or $R^1$ is

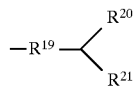

wherein $R^{19}$ is aryl or heteroaryl;

$R^{20}$ is aryl or heteroaryl;

$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;

$R^2$, $R^3$, $R^4$ are independently hydrogen, halo, alkyl, haloalkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;

$R^5$ is alkyl of at least 2 carbons, alkenyl, alkynyl, aryl, heteroaryl, arylalkyl, heteroarylalkyl, cycloalkyl, cycloalkylalkyl, polycycloalkyl, polycycloalkylalkyl, cycloalkenyl, cycloalkenylalkyl, polycycloalkenyl, polycycloalkenylalkyl, heteroarylcarbonyl, all of the $R^5$ and $R^6$ substituents being optionally substituted through available carbon atoms with 1, 2, or 3 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino (wherein the amino includes 1 or 2 substituents which are alkyl, or aryl or any of the other aryl compounds mentioned in the definitions), thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino; with the proviso that when $R^5$ is $CH_3$, $R^6$ is not H; and where $R^5$ is phenyl, the phenyl preferably includes an ortho hydrophobic substituent such as alkyl, haloalkyl, aryl, aryloxy or arylalkyl;

$R^6$ is hydrogen or $C_1$–$C_4$ alkyl or $C_1$–$C_4$ alkenyl;

$R^7$ is alkyl, aryl or arylalkyl wherein alkyl or the alkyl portion is optionally substituted with oxo; and including pharmaceutically acceptable salts and anions thereof.

In the formula I compounds, where X is $CH_2$ and $R^2$, $R^3$ and $R^4$ are each H, $R^1$ will be other than 3,3-diphenylpropyl.

In the formula III compounds, where one of $R^2$, $R^3$ and $R^4$ is 6-fluoro, and the others are H, $R^7$ will be other than 4-O-methoxyphenyl.

U.S. application Ser. No. 472,067, filed Jun. 6, 1995 (file DC21e) discloses compounds of the structure

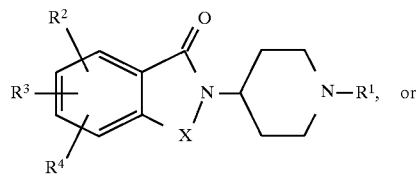

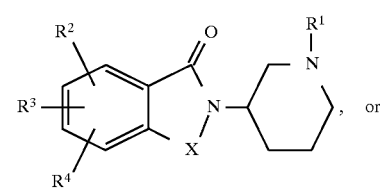

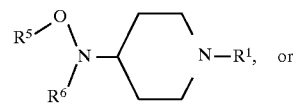

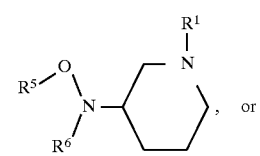

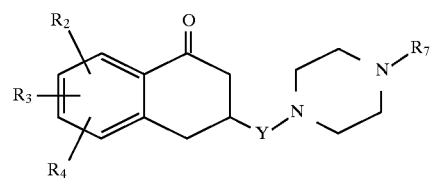

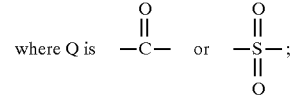

$R^8$, $R^9$ and $R^{10}$ are independently hydrogen, alkyl, alkenyl, alkynyl, aryl, arylalkyl, heteroaryl, heteroarylalkyl, cycloalkyl, or cycloalkylalkyl;

Y is —(CH$_2$)$_m$— or —C(=O)— wherein m is 2 or 3;

$R^1$ is alkyl, alkenyl, alkynyl, aryl, heteroaryl, arylalkyl wherein alkyl has at least 2 carbons, diarylalkyl, arylalkenyl, diarylalkenyl, arylalkynyl, diarylalkynyl, diarylalkylaryl, heteroarylalkyl wherein alkyl has at least 2 carbons, cycloalkyl, or cycloalkylalkyl wherein alkyl has at least 2 carbons, all optionally substituted through available carbon atoms with 1, 2, 3 or 4 groups selected from halo, haloalkyl, alkyl, alkenyl, alkoxy, aryloxy, aryl, arylalkyl, alkylmercapto, arylmercapto, cycloalkyl, cycloalkylalkyl, heteroaryl, fluorenyl, heteroarylalkyl, hydroxy or oxo;

or $R^1$ is a fluorenyl-type group of the structure

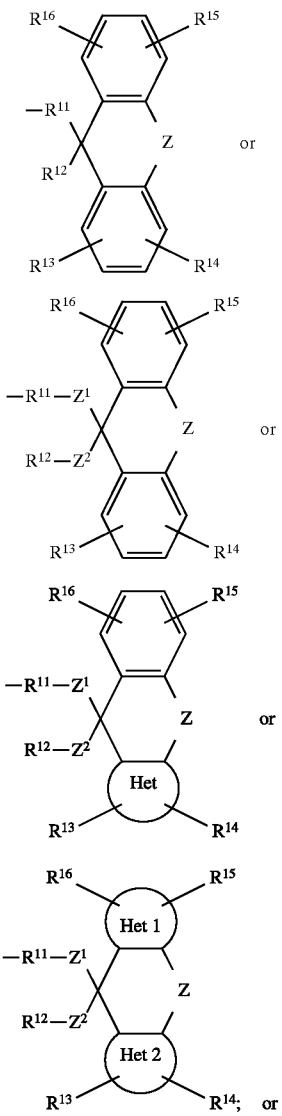

$R^1$ is an indenyl-type group of the structure

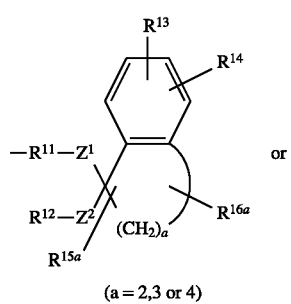

-continued

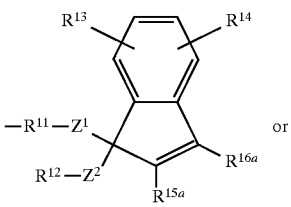

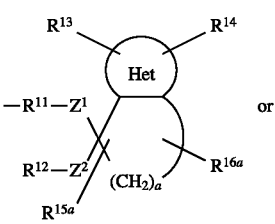

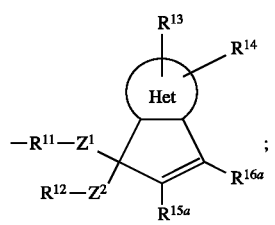

$Z^1$ and $Z^2$ are the same or different and are independently a bond, O, S, $$-\underset{O}{\overset{S}{\overset{\|}{C}}}-, \quad \left(\underset{O}{\overset{S}{\overset{\|}{C}}}-\right)_2, \quad -NH-\underset{O^-}{\overset{C}{\overset{\|}{C}}}-, \quad -\underset{alkyl}{\overset{|}{N}}-\underset{O}{\overset{C}{\overset{\|}{C}}}-, \quad -\underset{O}{\overset{C}{\overset{\|}{C}}}- \quad or \quad -\underset{OH}{\overset{H}{\overset{|}{C}}}-,$$

with the proviso that with respect to B, at least one of $Z^1$ and $Z^2$ will be other than a bond; $R^{11}$ is a bond, alkylene, alkenylene or alkynylene of up to 10 carbon atoms; arylene or mixed arylene-alkylene; $R^{12}$ is hydrogen, alkyl, alkenyl, aryl, haloalkyl, trihaloalkyl, trihaloalkylalkyl, heteroaryl, heteroarylalkyl, arylalkyl, arylalkenyl, cycloalkyl, aryloxy, alkoxy, arylalkoxy or cycloalkylalkyl, with the provisos that (1) when $R^{12}$ is H, aryloxy, alkoxy or arylalkoxy, then $Z^2$ is $$-NH-\underset{O}{\overset{C}{\overset{\|}{C}}}-, \quad -\underset{alkyl}{\overset{|}{N}}-\underset{O}{\overset{C}{\overset{\|}{C}}}-, \quad -\underset{O}{\overset{C}{\overset{\|}{C}}}-$$

or a bond and (2) when $Z^2$ is a bond, $R^{12}$ cannot be heteroaryl or heteroarylalkyl;

Z is bond, O, S, N-alkyl, N-aryl, or alkylene or alkenylene from 1 to 5 carbon atoms; $R^{13}$, $R^{14}$, $R^{15}$, and $R^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl or aryloxy;

$R^{15a}$ and $R^{16a}$ are independently hydrogen, alkyl, halo, haloalkyl, aryl, cycloalkyl, cycloheteroalkyl, alkenyl, alkynyl, alkoxy, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl, or aryloxy;

or $R^1$ is a group of the structure

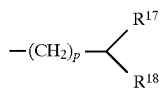

wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl at least one of $R^{17}$ and $R^{18}$ being other than H;

or $R^1$ is a group of the structure

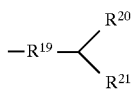

wherein $R^{19}$ is aryl or heteroaryl;

$R^{20}$ is aryl or heteroaryl;

$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;

$R^2$, $R^3$, $R^4$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;

$R^5$ is independently alkyl, alkenyl, alkynyl, aryl, alkoxy, aryloxy, arylalkoxy, heteroaryl, arylalkyl, heteroarylalkyl, cycloalkyl, cycloalkylalkyl, polycycloalkyl, polycycloalkylalkyl, cycloalkenyl, cycloheteroalkyl, heteroaryloxy, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino, thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, alkylsulfinyl;

$R^6$ is hydrogen or $C_1$-$C_4$ alkyl or $C_1$-$C_4$ alkenyl; all optionally substituted with 1, 2, 3 or 4 groups which may independently be any of the substituents listed in the definition of $R^5$ set out above;

$R^7$ is alkyl, aryl or arylalkyl wherein alkyl by itself or as part of arylalkyl is optionally substituted with oxo

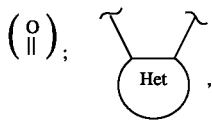

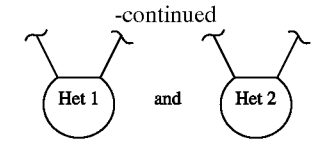

are the same or different and are independently selected from heteroaryl containing 5- or 6-ring members; and
N-oxides

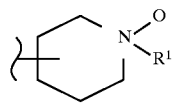

thereof; and pharmaceutically acceptable salts thereof;

with the provisos that where in the first formula X is $CH_2$, and $R^2$, $R^3$ and $R^4$ are each H, then $R^1$ will be other than 3,3-diphenylpropyl, and in the fifth formula, where one of $R^2$, $R^3$ and $R^4$ is 6-fluoro, and the others are H, $R^7$ will be other than 4-(2-methoxyphenyl).

U.S. application Ser. No. 548,811 filed Jan. 11, 1996 (file DC21h), discloses compounds having the structure

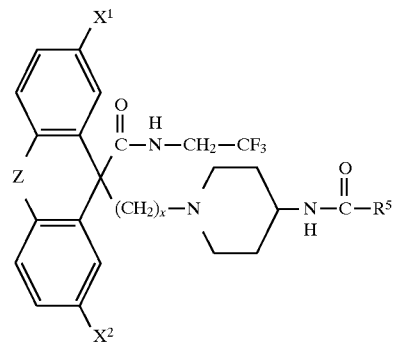

including the piperidine N-oxide thereof or a pharmaceutically acceptable salt thereof, wherein Z is a bond, O or S;

$X^1$ and $X^2$ are independently selected from H or halo;

x is an integer from 2 to 6;

$R^5$ is heteroaryl, aryl, heterocycloalkyl or cycloalkyl, each $R^5$ group being optionally substituted with 1, 2, 3 or 4 substituents which may be the same or different.

SUMMARY OF THE INVENTION

In accordance with the present invention, novel compounds are provided which are inhibitors of MTP and have the structure

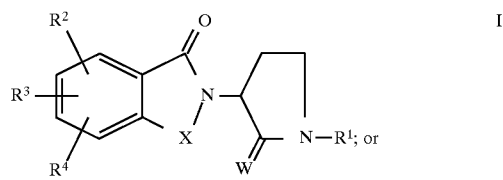

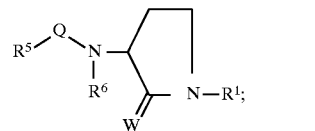

W is H,H or O;

X is

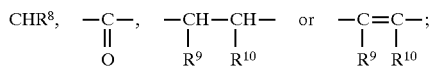

$R^8$, $R^9$ and $R^{10}$ are independently hydrogen, alkyl, alkenyl, alkynyl, aryl, arylalkyl, heteroaryl, heteroarylalkyl, cycloalkyl, or cycloalkylalkyl;

$R^1$ is alkyl, alkenyl, alkynyl, aryl, heteroaryl, arylalkyl (wherein alkyl preferably has at least 2 carbons, more preferably at least 3 carbons), diarylalkyl, arylalkenyl, diarylalkenyl, arylalkynyl, diarylalkynyl, diarylalkylaryl, heteroarylalkyl (wherein alkyl preferably has at least 2 carbons, more preferably at least 3 carbons), cycloalkyl, or cycloalkylalkyl (wherein alkyl preferably has at least 2 carbons, more preferably at least 3 carbons); all of the aforementioned $R^1$ groups being optionally substituted through available carbon atoms with 1, 2, 3 or 4 groups selected from halo, haloalkyl, alkyl, alkenyl, alkoxy, aryloxy, aryl, arylalkyl, alkyl-mercapto, arylmercapto, cycloalkyl, cycloalkyl-alkyl, heteroaryl, fluorenyl, heteroarylalkyl, hydroxy or oxo; or $R^1$ is a fluorenyl-type group of the structure

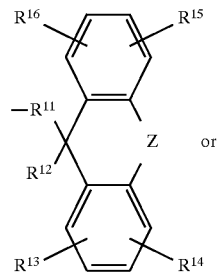
A

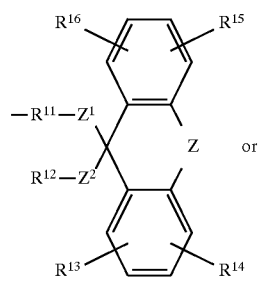
B

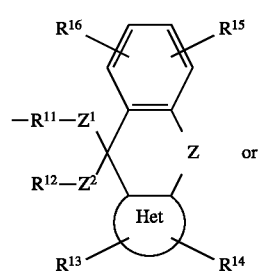
C $R^1$ is an indenyl-type group of the structure

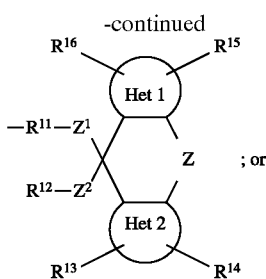
D

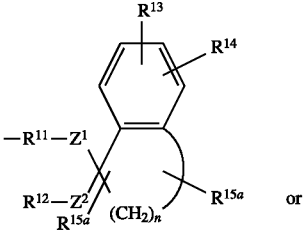
E
(a = 2,3 or 4)

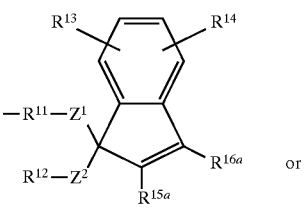
F

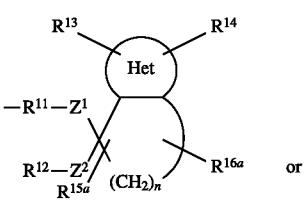
G

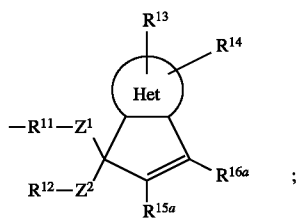
H $Z^1$ and $Z^2$ are the same or different and are independently a bond, O, S,

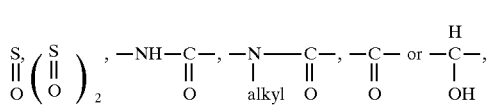

with the proviso that with respect to B, at least one of $Z^1$ and $Z^2$ will be other than a bond;

$R^{11}$ is a bond, alkylene, alkenylene or alkynylene of up to 10 carbon atoms, arylene (for example

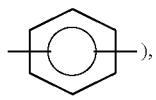

or mixed arylene-alkylene (for example

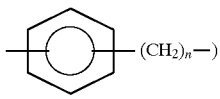

where n is 1 to 6;

$R^{12}$ is hydrogen, alkyl, alkenyl, aryl, haloalkyl, trihaloalkyl, trihaloalkylalkyl, heteroaryl, heteroarylalkyl, arylalkyl, arylalkenyl, cycloalkyl, aryloxy, alkoxy, arylalkoxy or cycloalkylalkyl; with the provisos that (1) when $R^{12}$ is H, aryloxy, alkoxy or arylalkoxy, then $Z^2$ is

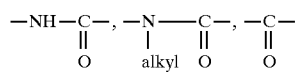

or a bond;

and (2) when $Z^2$ is a bond, $R^{12}$ cannot be heteroaryl or heteroarylalkyl;

Z is a bond, O, S, N-alkyl, N-aryl, or alkylene or alkenylene of from 1 to 5 carbon atoms;

$R^{13}, R^{14}, R^{15}$, and $R^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl, or aryloxy;

$R^{15a}$ and $R^{16a}$ are independently any of the $R^{15}$ or $R^{16}$ groups except hydroxy, nitro, amino or thio;

or $R^1$ is

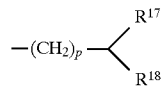

wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl, at least one of $R^{17}$ and $R^{18}$ being other than H;

or $R^1$ is

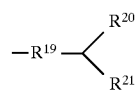

wherein
$R^{19}$ is aryl or heteroaryl;
$R^{20}$ is aryl or heteroaryl;
$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;

$R^2, R^3, R^4$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;

$R^5$ is alkyl, alkenyl, alkynyl, aryl, alkoxy, aryloxy, arylalkoxy, heteroaryl, arylalkyl, heteroarylalkyl, cycloalkyl, cycloheteroalkyl, heteroaryloxy, cycloalkylalkyl, polycycloalkyl, polycycloalkylalkyl, cycloalkenyl, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all of the $R^5$ substituents and $R^6$ substituents (set out hereinafter) being optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino (wherein the amino includes 1 or 2 substituents which are alkyl, aryl or heteroaryl, or any of the other aryl compounds mentioned in the definitions), thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, or alkylsulfinyl. Where $R^5$ is phenyl, aryl, heteroaryl or cycloalkyl; this group preferably includes an ortho hydrophobic substituent such as alkyl, haloalkyl (with up to 5 halo groups), alkoxy, haloalkoxy (with up to 5 halo groups), aryl, aryloxy or arylalkyl;

$R^6$ is hydrogen or $C_1$–$C_4$ alkyl or $C_1$–$C_4$ alkenyl;

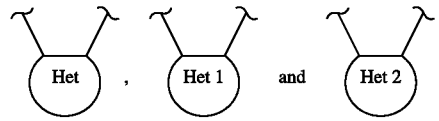

are the same or different and are independently selected from heteroaryl containing 5- or 6-ring members; and including N-oxides of the formulae I and II compounds, that is

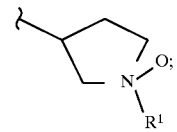

and including pharmaceutically acceptable salts thereof such as alkali metal salts such as lithium sodium or potassium, alkaline earth metal salts such as calcium or magnesium, as well as zinc or aluminum and other cations such as ammonium, choline, diethanolamine, ethylenediamine, t-butylamine, t-octylamine, dehydroabietylamine, as well as pharmaceutically acceptable anions such as chloride, bromide, iodide, tartrate, acetate, methanesulfonate, maleate, succinate, glutarate, and salts of naturally occurring amino acids such as arginine, lysine, alanine and the like, and prodrug esters thereof.

In the formula I compounds, where X is $CH_2$ and $R^2, R^3$ and $R^4$ are each H, $R^1$ will preferably be other than 3,3-diphenylpropyl.

Thus, the compounds of formulae I and II of the invention encompass compounds of the structure

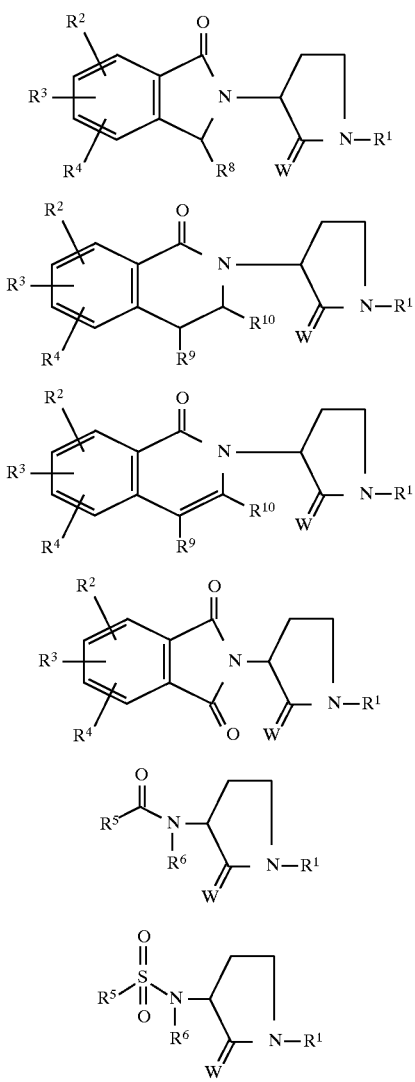

It will be understood that the pyrrolidinyl ring shown in the above formulas depicting compounds of the invention as well as in starting materials and intermediates shown in the Reaction Schemes to follow can be in racemic form or are R- or S-enantiomers.

In addition, in accordance with the present invention, a method for preventing, inhibiting or treating atherosclerosis, pancreatitis or obesity is provided, wherein a compound of formula I or II as defined hereinbefore is administered in an amount which decreases the activity of microsomal triglyceride transfer protein.

Furthermore, in accordance with the present invention, a method is provided for lowering serum lipid levels, cholesterol and/or triglycerides, or inhibiting and/or treating hyperlipemia, hyperlipidemia, hyperlipoproteinemia, hypercholesterolemia and/or hypertriglyceridemia, wherein a compound of formula I or II is administered in an amount which decreases the activity of microsomal triglyceride transfer protein.

DETAILED DESCRIPTION OF THE INVENTION

The following definitions apply to the terms as used throughout this specification, unless otherwise limited in specific instances.

The term "MTP" refers to a polypeptide or protein complex that (1) if obtained from an organism (e.g., cows, humans, etc.), can be isolated from the microsomal fraction of homogenized tissue; and (2) stimulates the transport of triglycerides, cholesterol esters, or phospholipids from synthetic phospholipid vesicles, membranes or lipoproteins to synthetic vesicles, membranes, or lipoproteins and which is distinct from the cholesterol ester transfer protein [Drayna et al., Nature 327, 632–634 (1987)] which may have similar catalytic properties. However, the MTP molecules of the present invention do not necessarily need to be catalytically active. For example, catalytically inactive MTP or fragments thereof may be useful in raising antibodies to the protein.

The phrase "stabilizing" atherosclerosis as used in the present application refers to slowing down the development of and/or inhibiting the formation of new atherosclerotic lesions.

The phrase "causing the regression of" atherosclerosis as used in the present application refers to reducing and/or eliminating atherosclerotic lesions.

Unless otherwise indicated, the term "lower alkyl", "alkyl" or "alk" as employed herein alone or as part of another group includes both straight and branched chain hydrocarbons, containing 1 to 40 carbons, preferably 1 to 20 carbons, more preferably 1 to 12 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups including 1 to 4 substituents such as halo, for example F, Br, Cl or I or $CF_3$, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, acyl, heteroaryl, heteroaryloxy, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio, as well as any of the other substituents as defined for $R^5$ and $R^6$.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 4 to 12 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

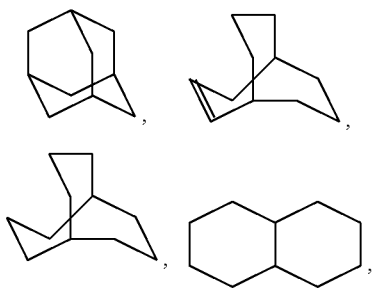

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio, as well as any of the other substituents as defined for $R^5$ or $R^6$.

The term "cycloalkenyl" as employed herein alone or as part of another group refers to cyclic hydrocarbons containing 5 to 20 carbons, preferably 6 to 12 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "polycycloalkyl" as employed herein alone or as part of another group refers to a bridged multicyclic group containing 5 to 20 carbons and containing 0 to 3 bridges, preferably 6 to 12 carbons and 1 or 2 bridges. Exemplary polycycloalkyl groups include [3.3.0]-bicyclooctanyl, adamantanyl, [2.2.1]-bicycloheptanyl, [2.2.2]-bicyclooctanyl and the like and may be optionally substituted as defined for cycloalkyl.

The term "polycycloalkenyl" as employed herein alone or as part of another group refers to a bridged multicyclic group containing 5 to 20 carbons and containing 0 to 3 bridges and containing 1 or 2 double bonds, preferably 6 to 12 carbons and 1 or 2 bridges. Exemplary polycycloalkyl groups include [3.3.0]-bicyclooctenyl, [2.2.1]-bicycloheptenyl, [2.2.2]-bicyclooctenyl and the like and may be optionally substituted as defined for cycloalkyl.

The term "aryl" or "Ar" as employed herein alone or as part of another group refers to monocyclic and bicyclic aromatic groups containing 6 to 10 carbons in the ring portion (such as phenyl or naphthyl) and may optionally include one to three additional rings fused to Ar (such as aryl, cycloalkyl, heteroaryl or cycloheteroalkyl rings) and may be optionally substituted through available carbon atoms with 1, 2, 3 or 4 groups selected from hydrogen, halo, haloalkyl, alkyl, haloalkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl, or any of the substituents as defined for the $R^5$ or $R^6$ groups set out above.

The term "aralkyl", "aryl-alkyl" or "aryllower alkyl" as used herein alone or as part of another group refers to alkyl groups as discussed above having an aryl substituent, such as benzyl or phenethyl, or naphthylpropyl, or an aryl as defined above.

The term "lower alkoxy", "alkoxy", "aryloxy" or "aralkoxy" as employed herein alone or as part of another group includes any of the above alkyl, aralkyl or aryl groups linked to an oxygen atom.

The term "amino" as employed herein alone or as part of another group may optionally be substituted with one or two substituents such as alkyl and/or aryl.

The term "lower alkylthio", alkylthio", "arylthio" or "aralkylthio" as employed herein alone or as part of another group includes any of the above alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

The term "acyl" as employed herein by itself or part of another group as defined herein, refers to an organic radical linked to a carbonyl

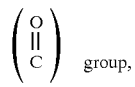  group, examples of acyl groups include alkanoyl, alkenoyl, aroyl, aralkanoyl, heteroaroyl, cycloalkanoyl and the like.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 3 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol and/or alkylthio, as well as any of the other substituents as defined for $R^5$ or $R^6$.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, as well as any of the other substituents as defined for $R^5$ or $R^6$.

The term "alkylene" as employed herein alone or as part of another group (which also encompasses "alkyl" as part of another group such as arylalkyl or heteroarylalkyl) refers to alkyl groups as defined above having single bonds for attachment to other groups at two different carbon atoms and may optionally be substituted as defined above for "alkyl". The definition of alkylene applies to an alkyl group which links one function to another, such as an arylalkyl substituent.

The terms "alkenylene" and "alkynylene" as employed herein alone or as part of another group (which also encompass "alkenyl" or "alkynyl" as part of another group such as arylalkenyl or arylalkynyl), refer to alkenyl groups as defined above and alkynyl groups as defined above, respectively, having single bonds for attachment at two different carbon atoms.

Suitable alkylene, alkenylene or alkynylene groups or $(CH_2)_n$ or $(CH_2)_p$ (which may include alkylene, alkenylene or alkynylene groups) as defined herein, may optionally include 1,2, or 3 alkyl, alkoxy, aryl, heteroaryl, cycloheteroalkyl, alkenyl, alkynyl, oxo, aryloxy, hydroxy, halogen substituents as well as any of the substituents defined for $R^5$ or $R^6$ and in addition, may have one of the carbon atoms in the chain replaced with an oxygen atom, N—H, N-alkyl or N-aryl. Examples of alkylene, alkenylene, alkynylene, $(CH_2)_n$ and $(CH_2)_p$ groups include

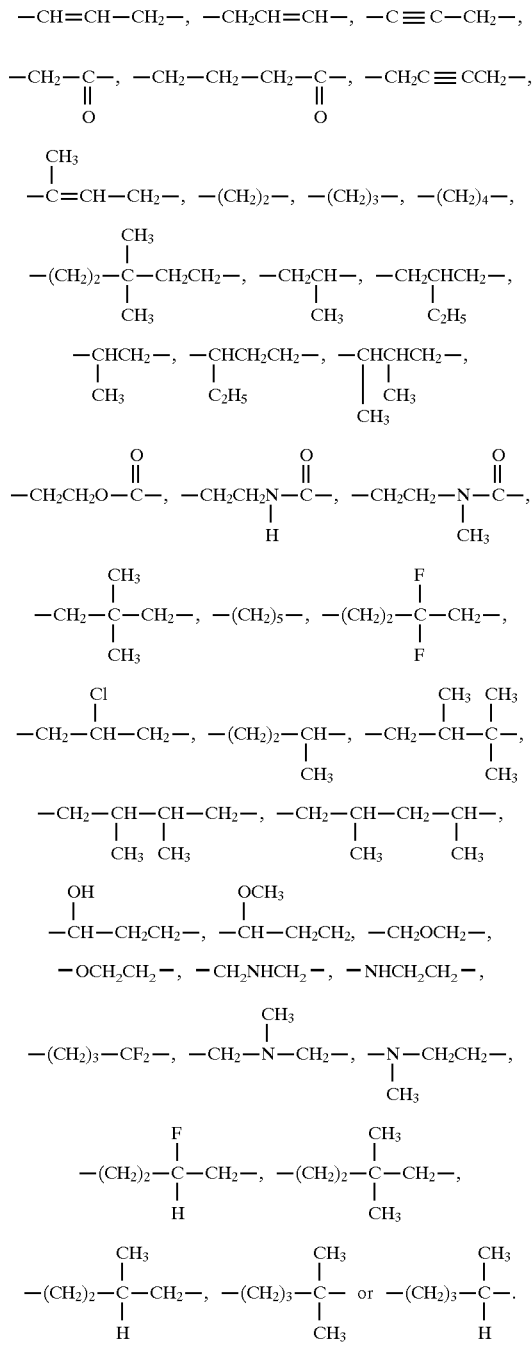

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

The term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (which is defined above), such as

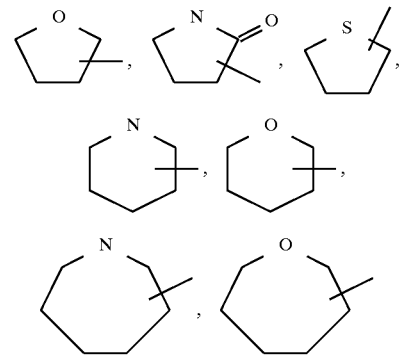

and the like. The above groups may include 1 to 3 substituents such as any of the $R^1$, $R^5$ or $R^6$ groups as defined above. In addition, any of the above rings can be fused to 1 or 2 cycloalkyl, aryl, heteroaryl or cycloheteroalkyl rings.

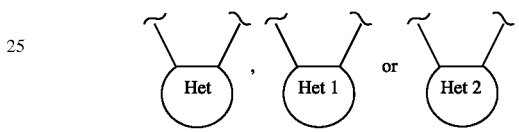

(also referred to as heteroaryl) as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), linked through a carbon atom or a heteroatom, where possible, optionally via the linker $(CH_2)_p$ (which is defined above), such as

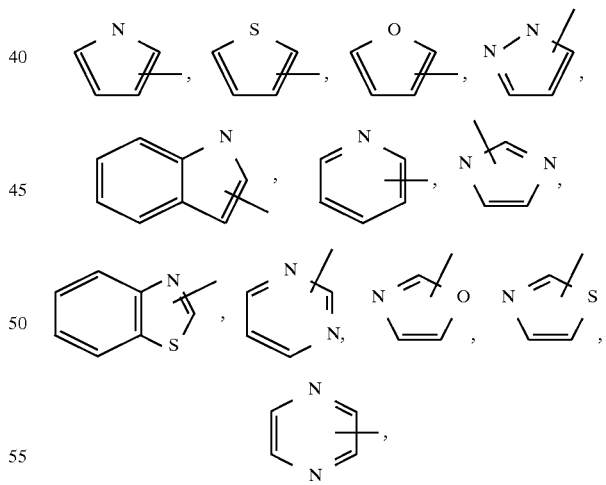

and the like, and includes all possible N-oxide derivatives.

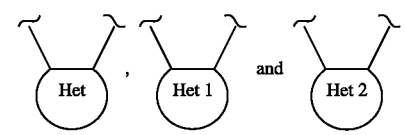

are the same or different as defined hereinbefore and are attached to the central ring of the indenyl or fluorenyl type group at adjacent positions (that is ortho or 1,2-positions). Examples of such groups include

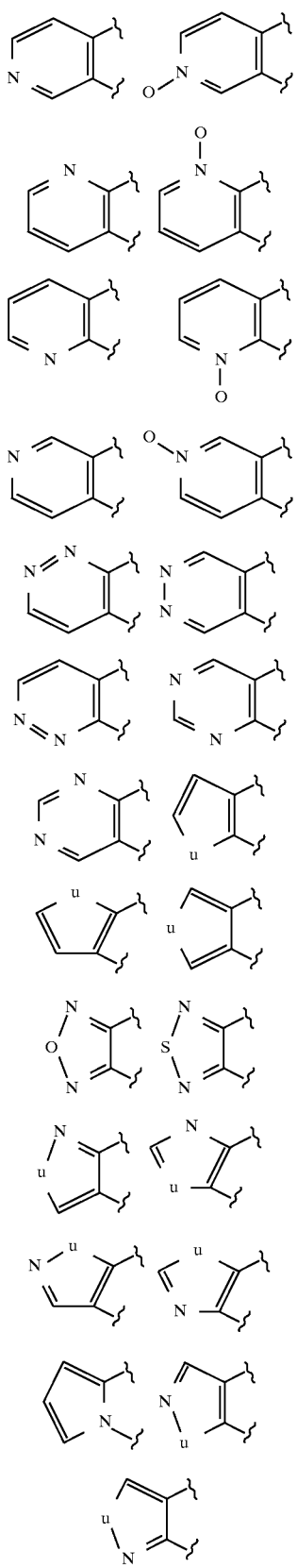

wherein u is selected from O, S, and $NR^{7a}$; $R^{7a}$ is H, lower alkyl, aryl, $-C(O)R^{7b}$, $-C(O)OR^{7b}$; $R^{7b}$ is alkyl or aryl, and includes all possible N-oxide derivatives.

The heteroaryl groups including the above groups may optionally include 1 to 4 substituents such as any of the substituents listed for aryl, or those substituents indicated for $R^5$ or $R^6$ groups as defined above. In addition, any of the above rings can be fused to a cycloalkyl, aryl, heteroaryl or cycloheteroalkyl ring.

The term cycloheteroalkylalkyl" as used herein alone or as part of another group refers to cycloheteroalkyl groups as defined above linked through a C atom or heteroatom to a $(CH_2)_p$ chain.

The term "heteroarylalkyl" or "heteroarylalkenyl" as used herein alone or as part of another group refers to a heteroaryl group as defined above linked through a C atom or heteroatom to a $-(CH_2)_p-$ chain, alkylene or alkenylene as defined above.

The term "fluorenyl" or "fluorenyl analog" or "fluorenyl-type group" as employed herein refers to a group of the structure:

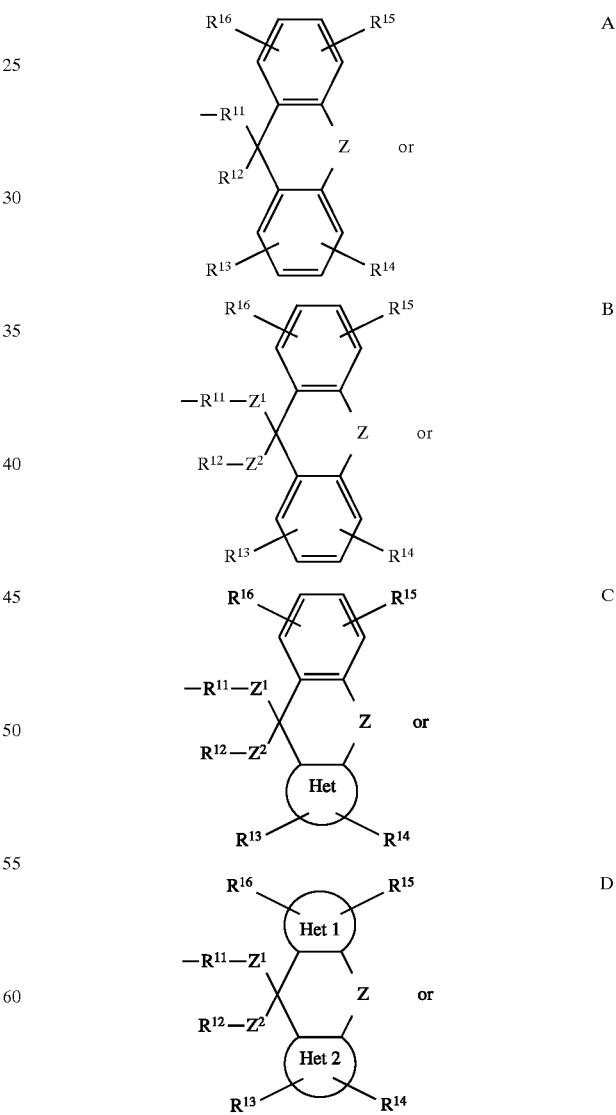

The term "indenyl-type group" as employed herein refers to a group of the structure

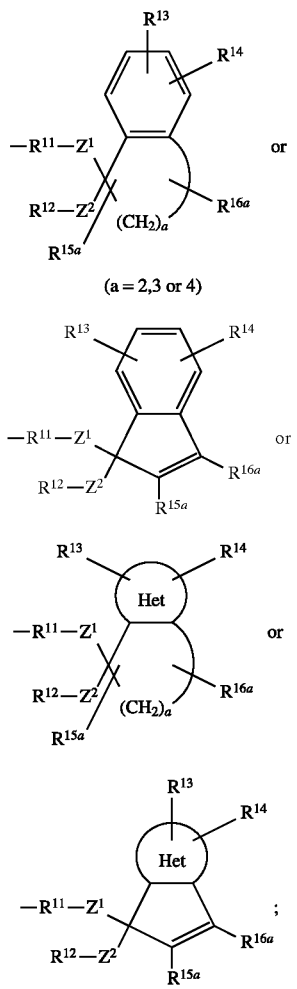

(a = 2,3 or 4)

$Z, Z^1, Z^2, R^{11}, R^{12}, R^{13}, R^{14}, R^{15}, R^{16}, R^{15a}$ and $R^{16a}$ as used in the above groups A through H are as defined hereinbefore.

Preferred are compounds of formulae I and II wherein $R^1$ is arylalkyl, arylalkenyl, heteroarylalkyl, heteroarylalkenyl,

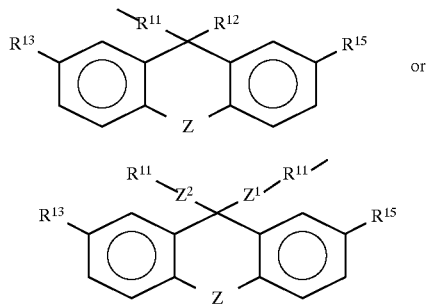

(including where $Z^1$ is a bond and $R^{11}$ is alkylene or alkenylene and $Z^2$ is

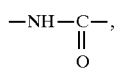

and $R^{12}$ is $C_1$–$C_3$ alkyl or 1,1,1-trifluoroethyl, $R^{13}$ is H or F and $R^{15}$ is H or F, and Z is a bond or O; and where $R^{11}$ is alkylene or alkenylene or alkylene substituted with oxo, $R^{12}$ is alkyl, alkenyl, aralkyl, aralkenyl, Z is O, S or a bond); or

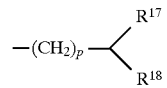

(wherein $R^{17}$ and $R^{18}$ are each independently alkyl, alkenyl, aryl, arylalkyl, heteroaryl, heteroarylalkyl, cycloalkyl or cycloalkylalkyl); or

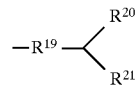

wherein $R^{19}$ is aryl or heteroaryl;

$R^{20}$ is aryl or heteroaryl;

$R^{21}$ is alkyl, aryl, alkylaryl, arylalkyl aryloxy, arylalkoxy, heteroaryl, heteroarylalkyl, heteroarylalkoxy, cycloalkyl, cycloalkylalkyl or cycloalkylalkoxy.

In structure I, it is preferred that $R^2$, $R^3$ and $R^4$ are each H and X is $CH_2$, $CH_2CH_2$, or CH=CH.

In structure II, it is preferred that $R^6$ is H or $CH_3$ and $R^5$ is cycloalkyl, phenyl, aryl or heteroaryl, or cycloalkyl, phenyl, aryl heteroaryl having an ortho hydrophobic substituent which is alkyl, alkoxy, haloalkyl (containing up to five halo groups), trifluoromethyl, aryl, aryloxy, arylalkyl, arylalkoxy, haloalkoxy (containing up to five halo groups).

In structure II, it is also preferred that $R^1$ is arylalkyl or heteroarylalkyl wherein alkyl of each has at least 2 carbons (preferably at least 3 carbons) and $R^5$ and $R^6$ may be as defined hereinbefore and may or may not be the preferred groups set out above.

It is to be understood that combinations of substituents which lead to chemically unstable molecules are not included within the scope of the present invention; for example, compounds of the invention will not include —O—O—, —O—C—OH, N—C—OH and —S—C—OH linkages.

The compounds of formulae I and II may be prepared by the exemplary processes described in the following reaction schemes. Exemplary reagents and procedures for these reactions appear hereinafter and in the working Examples.

Scheme I. Routes to Isoindolinone Piperidines
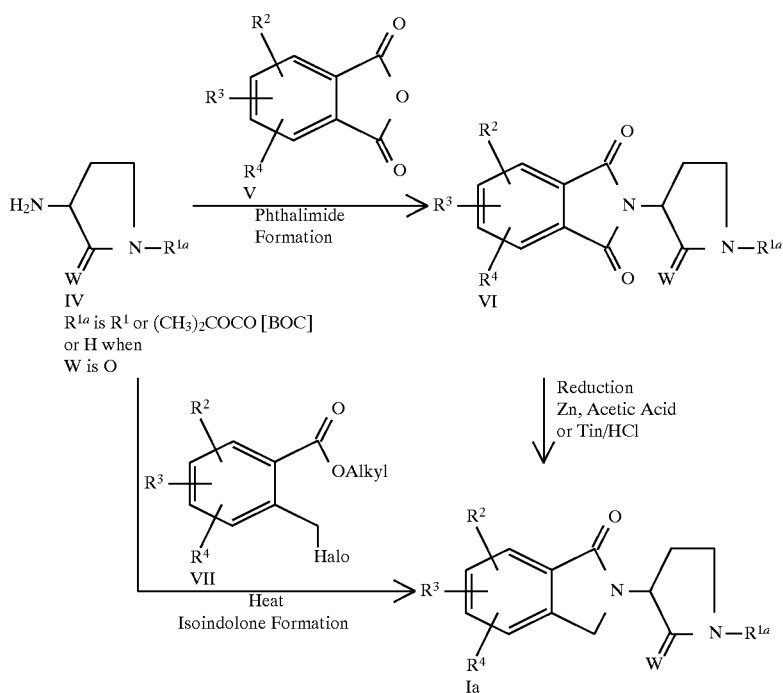
Scheme II. Additional Routes to Isoindolinone Piperidines
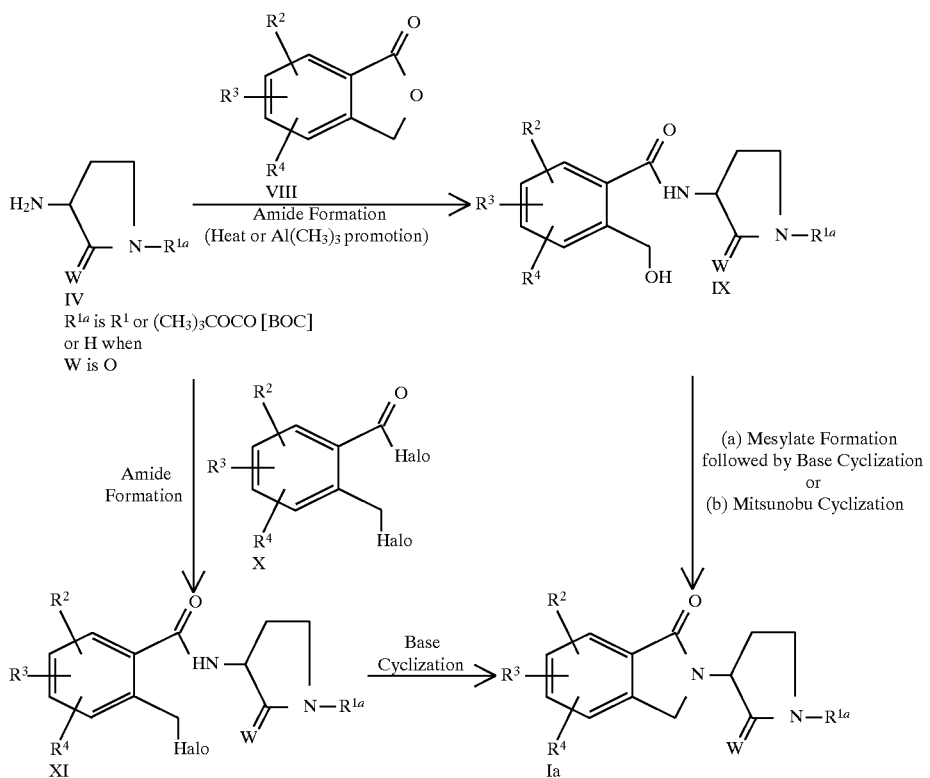

Scheme III. Introduction of R¹ by Alkylation or Arylation
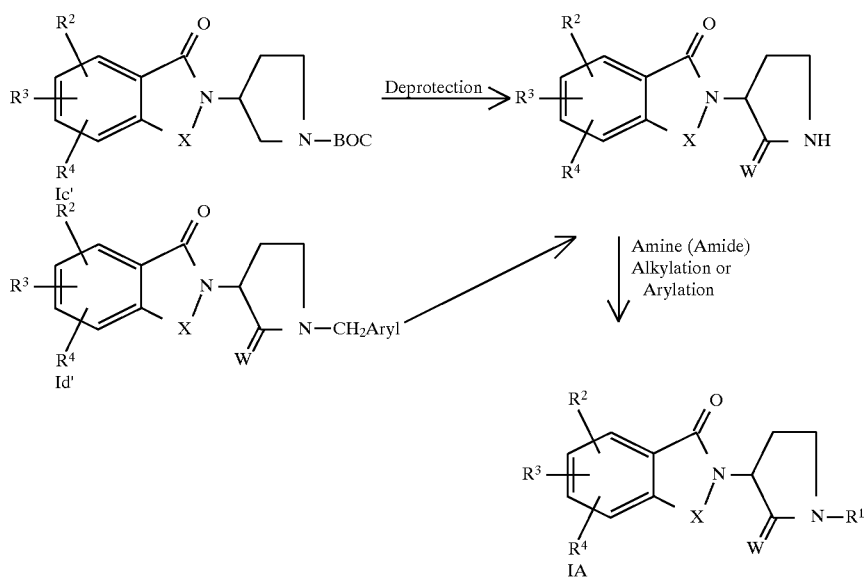
Scheme IV. Routes to Starting Materials IVb and IVc
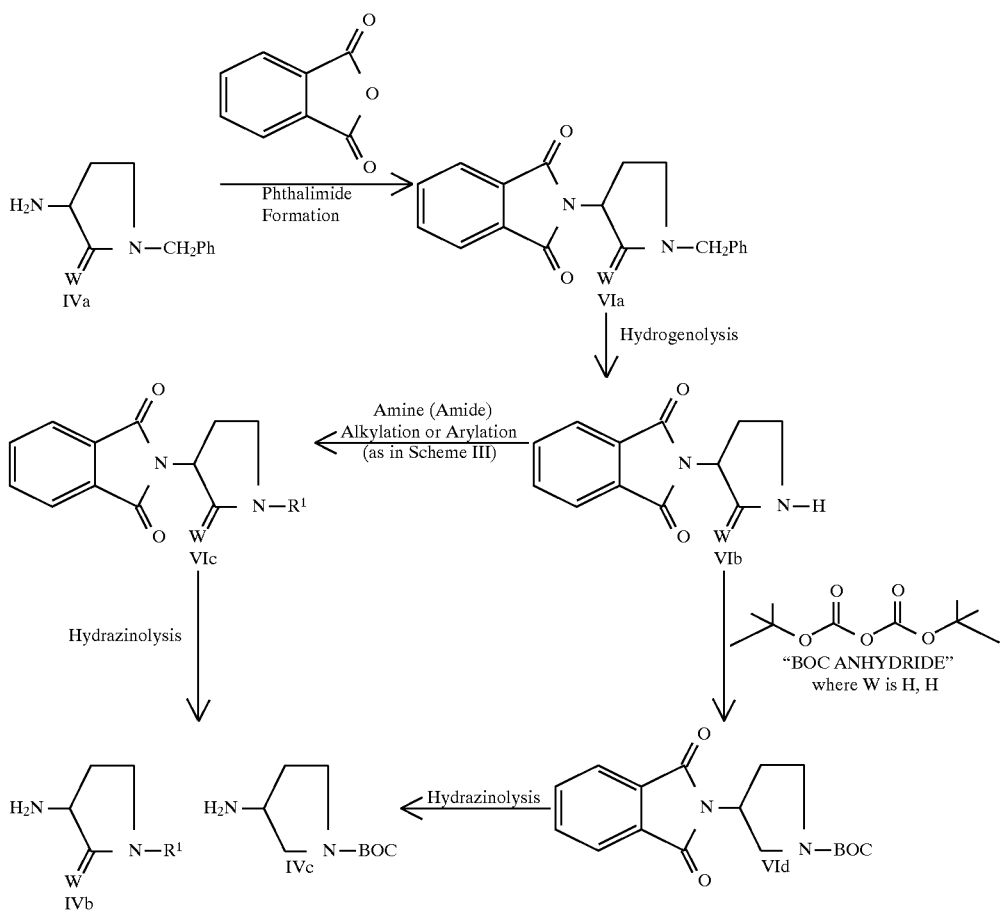

Scheme V. General Routes to Starting Materials IVb
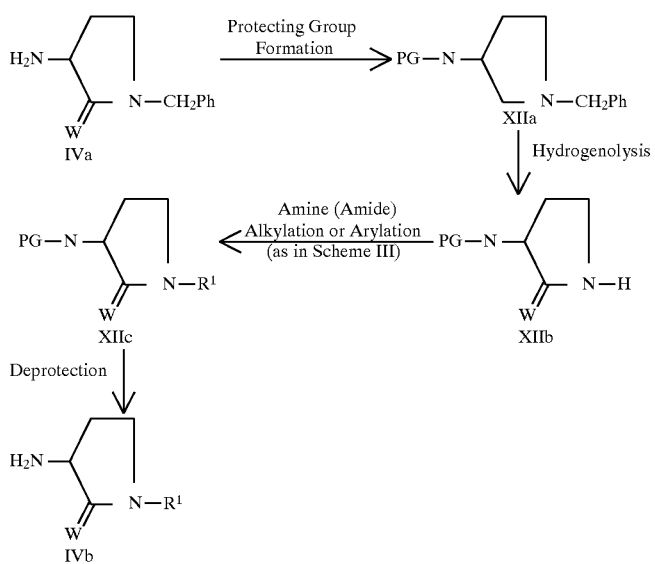
Schemes VI and VII General Routes to II
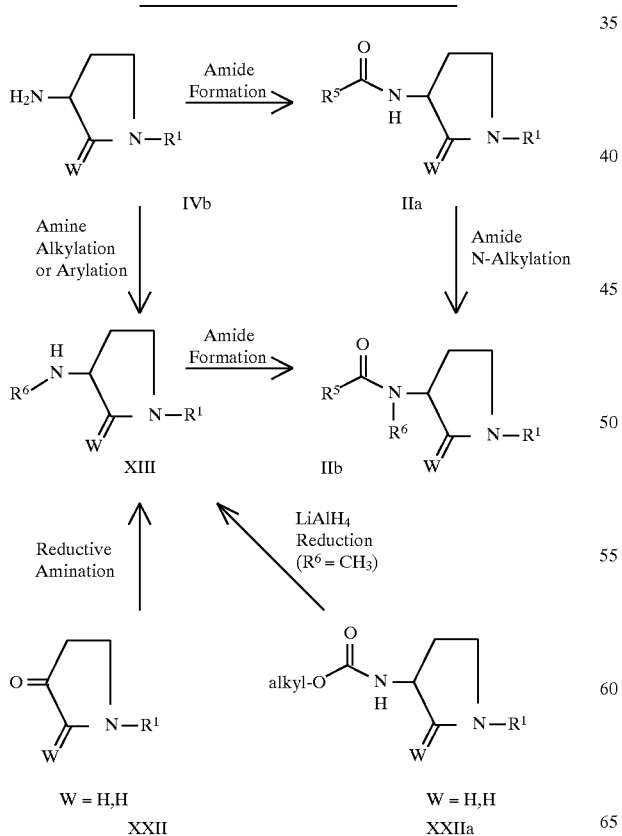

Scheme VIII Preparation of Compounds I$^b$, I$^c$
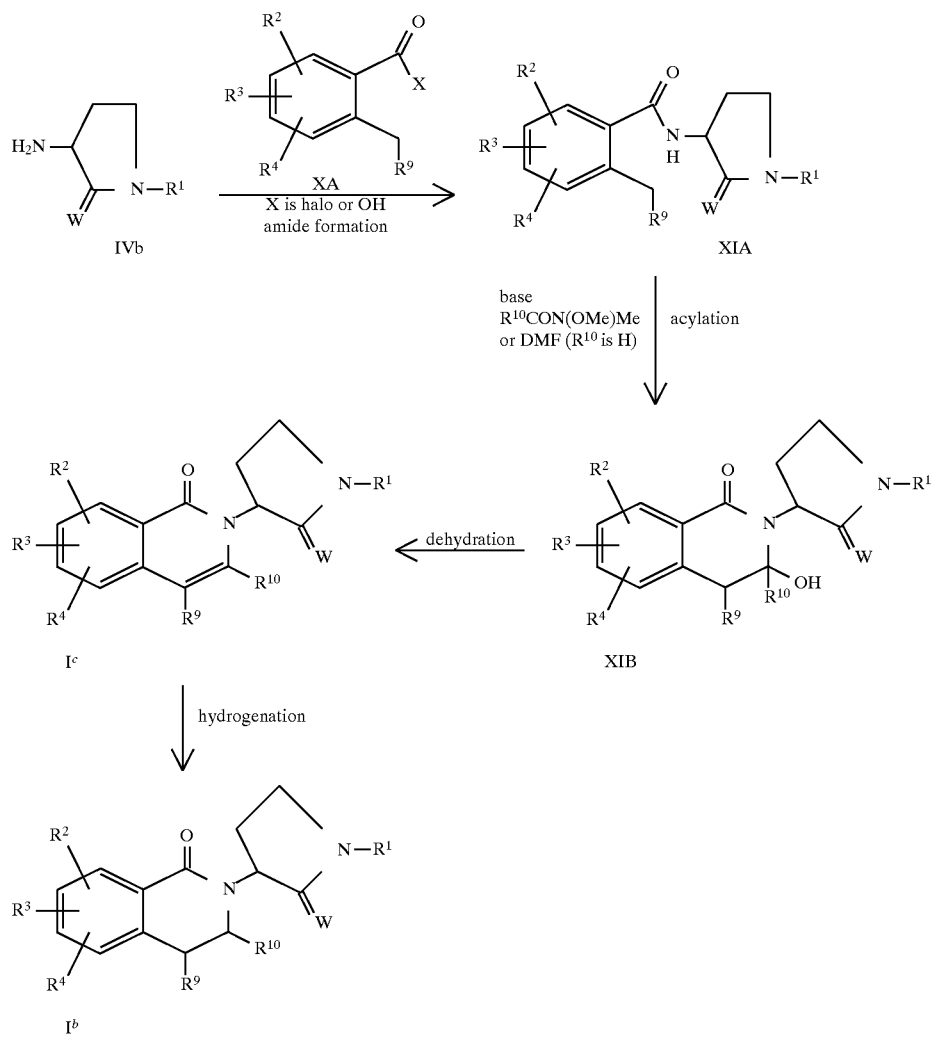
Scheme IX Preparation of Compounds IA$^1$–IA$^2$
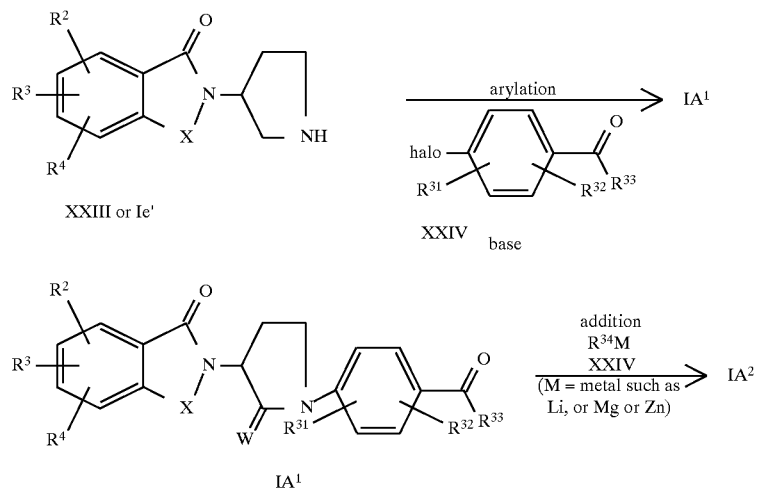

-continued
Scheme IX Preparation of Compounds IA¹–IA²
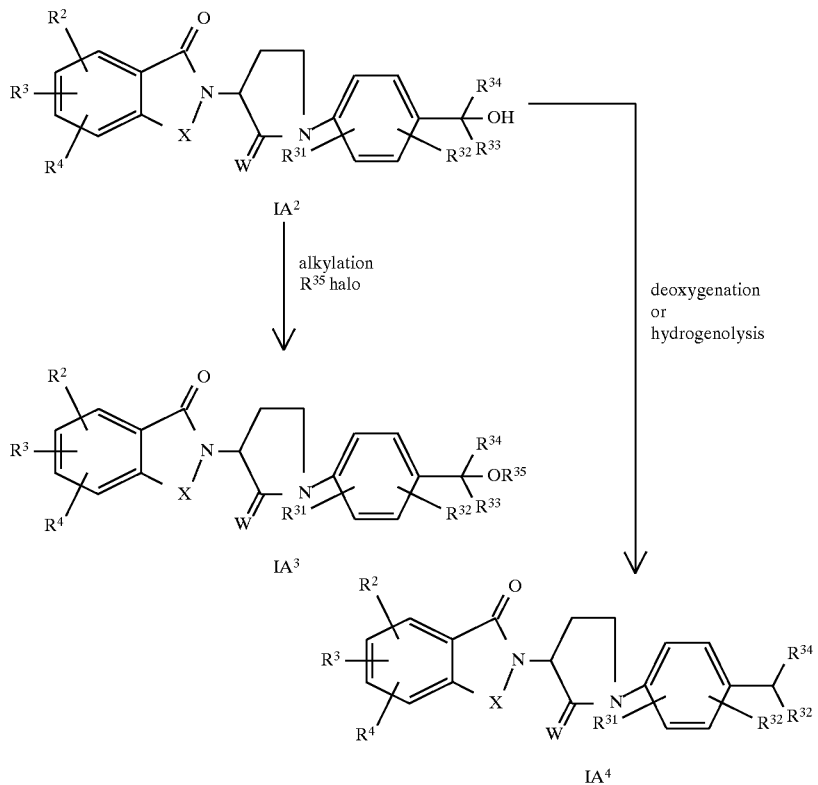
$R^{31}$ and $R^{32}$ are independently selected from any of the $R^2$, $R^3$, or $R^4$ radicals;
$R^{33}$ and $R^{34}$ are independently selected from any of the $R^1$ radicals as well as aryloxy, alkoxy, arylalkoxy, heteroarylalkoxy and heteroaryloxy;
$R^{35}$ can be any of the $R^1$ radicals.
Scheme X Preparation of Compound I$^a$
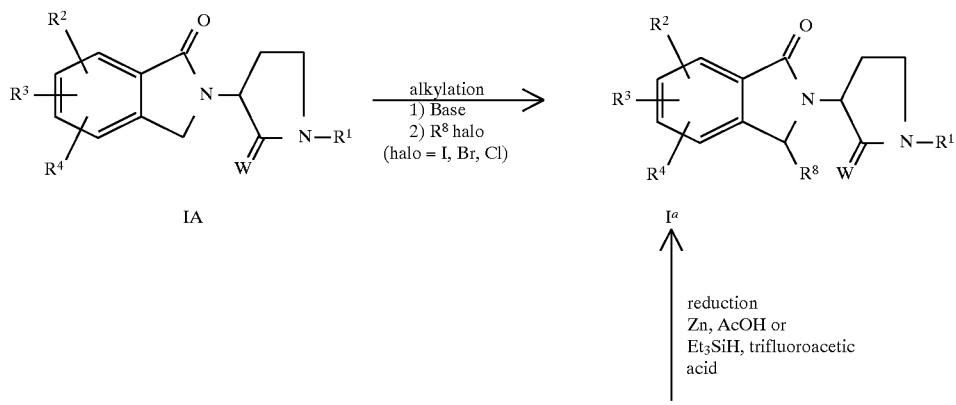

-continued
Scheme X Preparation of Compound I<sup>a</sup>

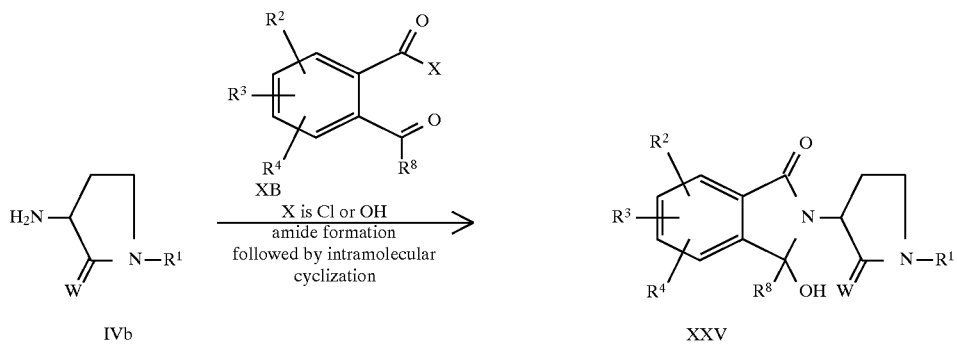

Scheme XI Preparation of Compound II
(Robotic Amide Coupling)

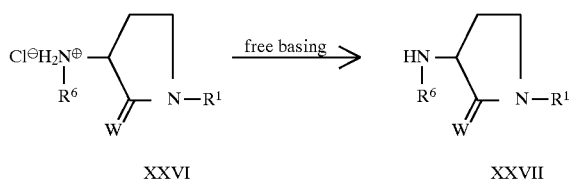

-continued
Scheme XI Preparation of Compound II
(Robotic Amide Coupling)

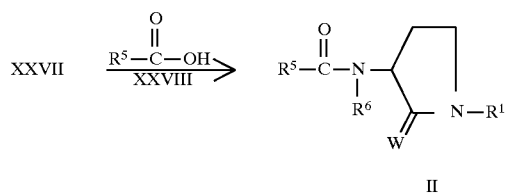

In the following Schemes XII et al, in the fluorenyl rings or fluorenyl analogs, the fused aryl groups:

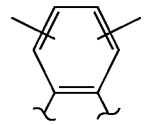

may each optionally be replaced by a 5- or 6-membered heteroaryl ring as defined herein.

Scheme XII

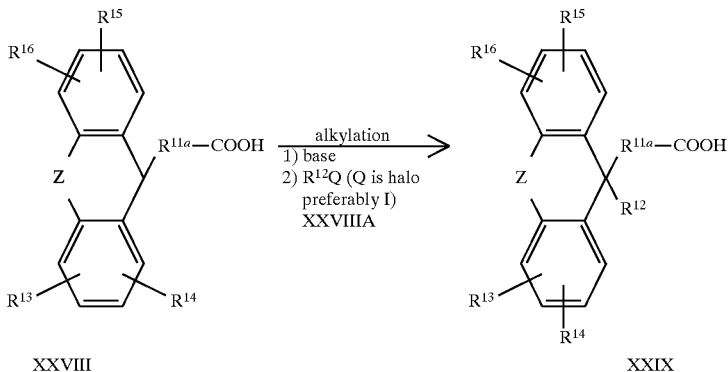

-continued
Scheme XII
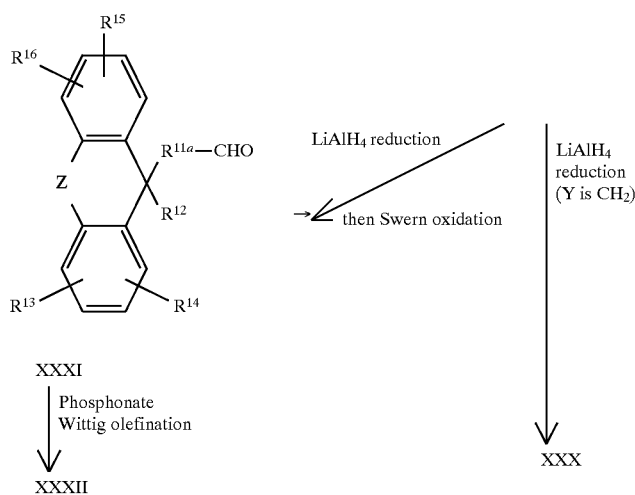
XXXI
Phosphonate Wittig olefination ↓
XXXII
$R^{11a}$ can be any of the $R^{11}$ radicals.
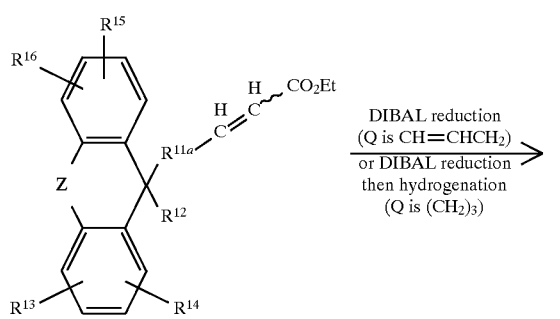
XXXII
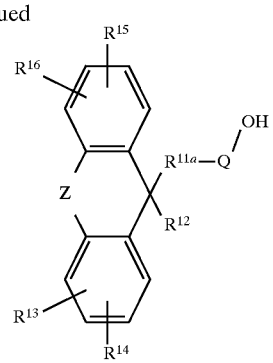
XXX
halogenation or sulfonation ↓
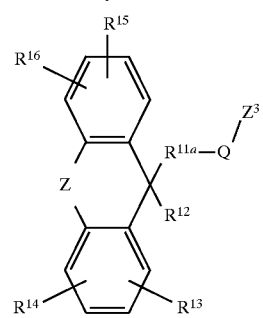
XXXIIIA
$Z^3$ is halo or Osulfonate Scheme XIII
Preparation of Intermediates where $Z^2$ is S, SO or $SO_2$
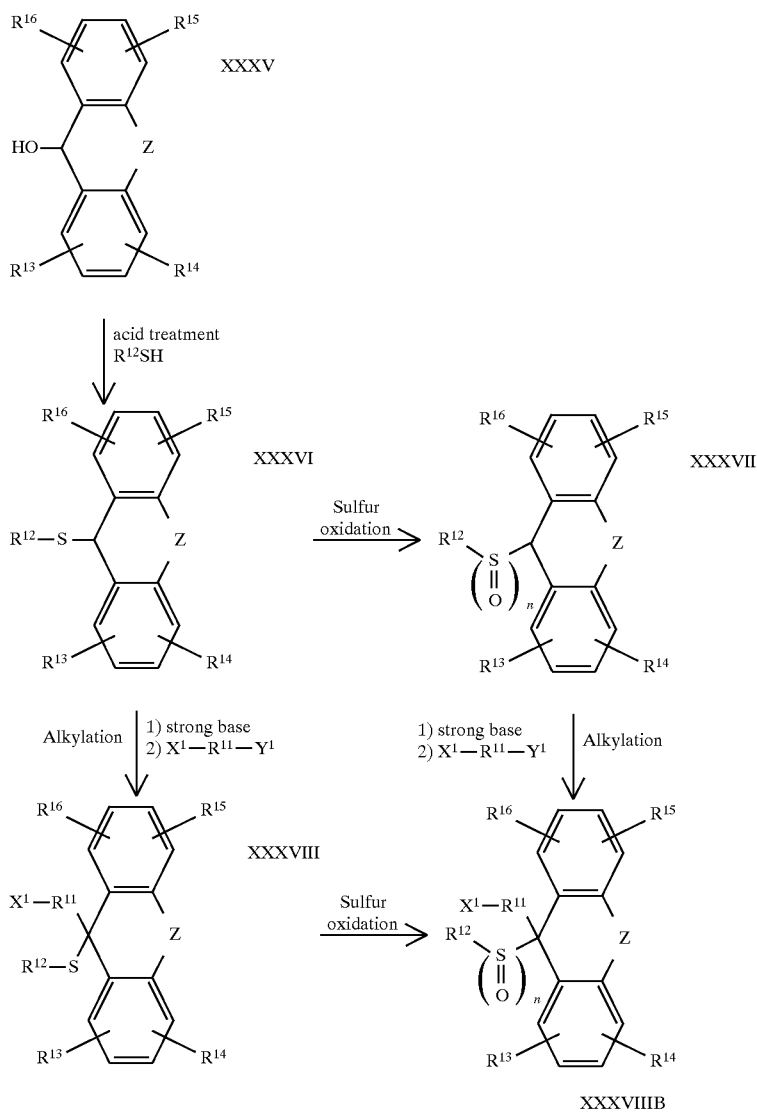
$X^1$, $Y^1$ are same or different halo or Osulfonate n=1 or 2

Scheme XIVA
Preparation of A (Intermediates where $Z^2$ is NHCO)

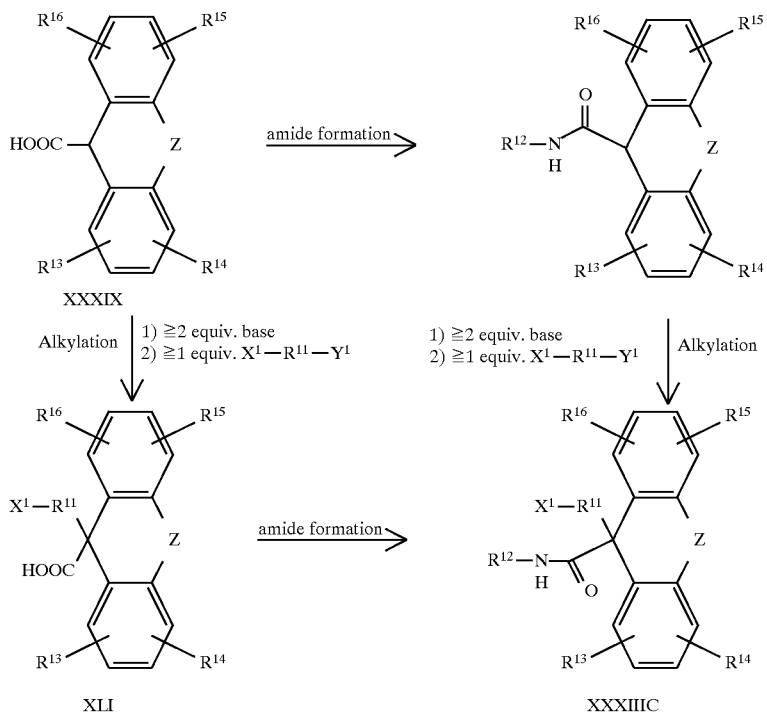

$X^1$, $Y^1$ are same or different halo or Osulfonate

Scheme XIVB
Alternative Procedure for Preparing Intermediate XL
(Shown in Scheme XIVA)

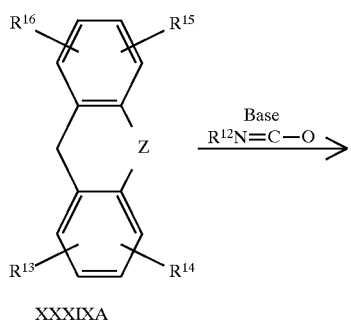

-continued
Scheme XIVB
Alternative Procedure for Preparing Intermediate XL
(Shown in Scheme XIVA)

In carrying out the above reaction, bases such as n-butyllithiun, lithium bis(trimethylsilyl) amide and sodium bis(trimethylsilyl) amide may be employed in an aprotic solvent such as THF, at between −78° C. and 35° C.
It is preferable to have the starting material and isocyanate ($R^{12}N=C-O$) together in solvent, and then add the base, and optionally add further excess isocyanate subsequently.

Scheme XV

Preparation of Intermediate where $Z^1$ is $-\overset{H}{N}-\overset{\|}{\underset{O}{C}}-$

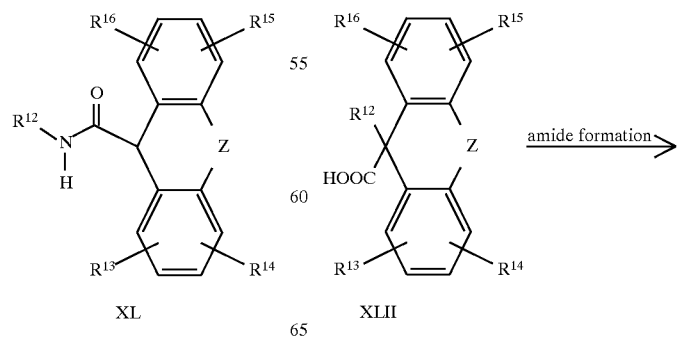

Scheme XV
Preparation of Intermediate where $Z^1$ is $-N-C-$
                                         $\phantom{-N-}H\phantom{C-}$
                                         $\phantom{-N-C}\|$
                                         $\phantom{-N-C-}O$
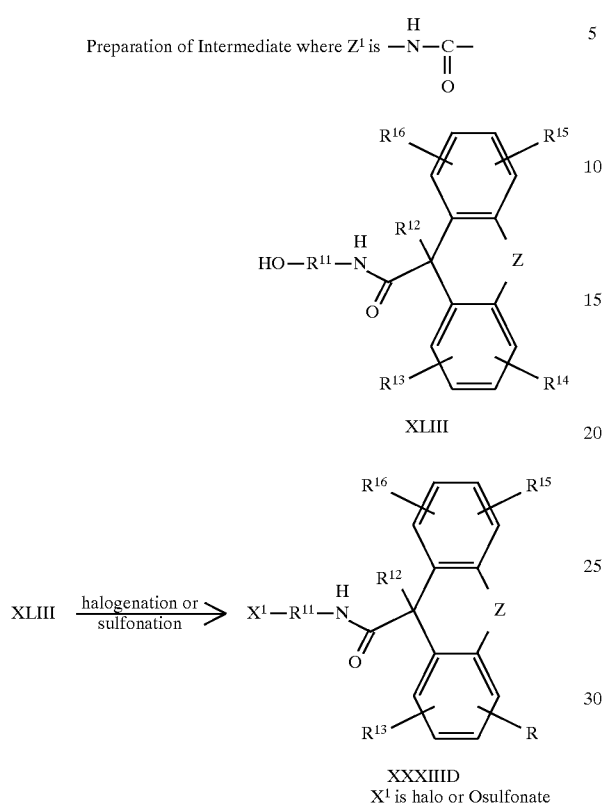
Scheme XVI
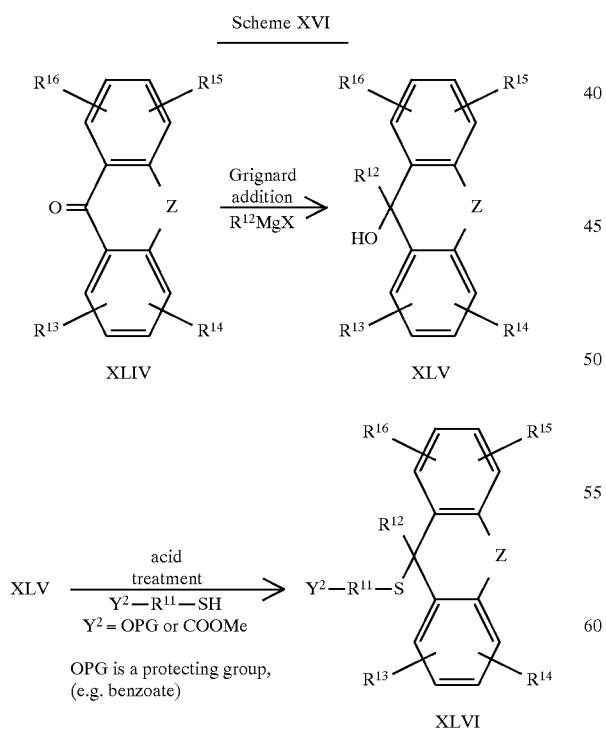
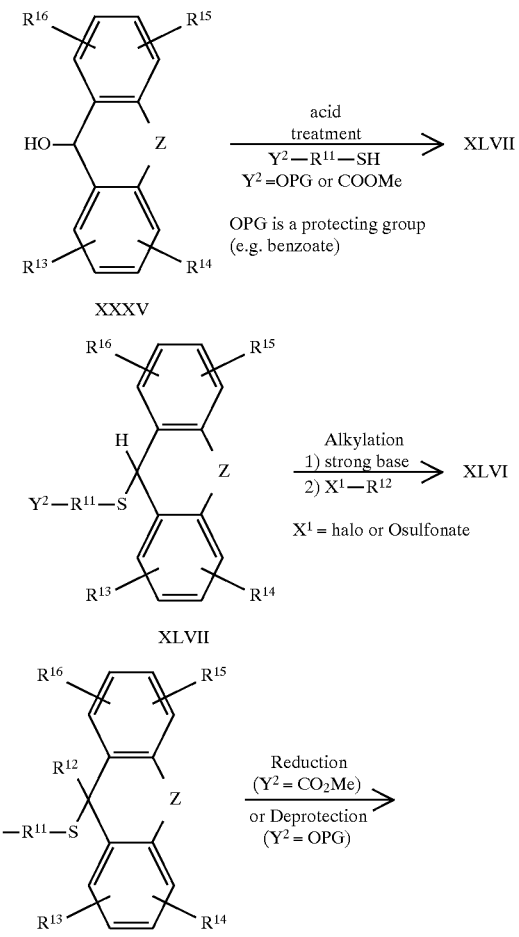

Scheme XVI

XXXIIIE →(Sulfur Oxidation)→ XXXIIIF (n = 1), XXXIIIG (n = 2)

Scheme XVIA
Preparation of Ketones

XXXIX →(alkylation, base, $R^{12}X^1$)→ XLII $X^1$ = halo or Osulfonate

XLII →(1) acid chloride formation for G = Cl (COCl)$_2$; 2) amide formation for G = MeN—OMe)→ XLIIA G = Cl or MeN—OMe XLIIA →(Ketone formation, $X^1MgO—R^{11}—MgX^1$, Optional catalytic Cu(I))→ XLIIB $X^1$ = halo or Osulfonate
$R^{11}$ is a chain of >2 carbons XLIIB →(halogenation)→ XXXIIIH $X^1$ = halo or Osulfonate

Scheme XVIB.
Preparation of Ketones (Preferred Route)

XXXIX →(Alkylation 1) base 2) PG—OR$^{11}$X$^1$; $X^1$ = halo or O-sulfonate)→ XLIIC XLIIC →(Decarboxylation DMSO, RT)→

Scheme XVIB.
Preparation of Ketones (Preferred Route)

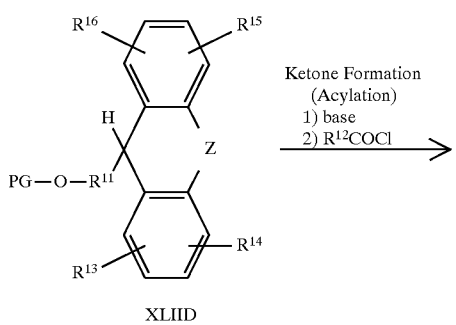

XLIID

Ketone Formation
(Acylation)
1) base
2) $R^{12}COCl$

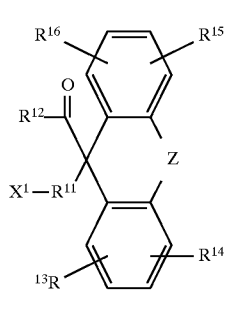

XXXIIII

PG is an appropiate protecting group:
such as t-butyl(dimethyl)silyl or
t-butyl(diphenyl)silyl, which can be
deprotected with aqueous acid or n-$Bu_4NF$.

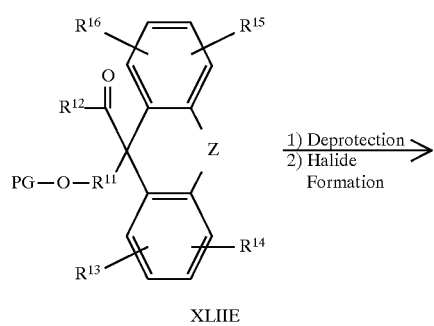

XLIIE

1) Deprotection
2) Halide Formation

Scheme XVIIA
Preparation of Amide Linked Compounds

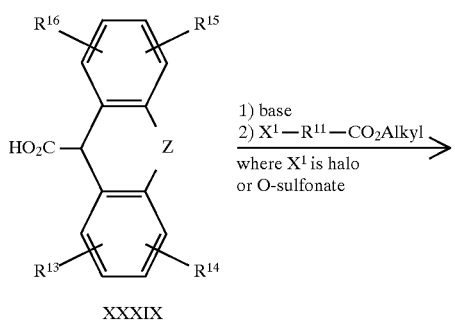

XXXIX 1) base
2) $X^1$—$R^{11}$—$CO_2Alkyl$
where $X^1$ is halo
or O-sulfonate

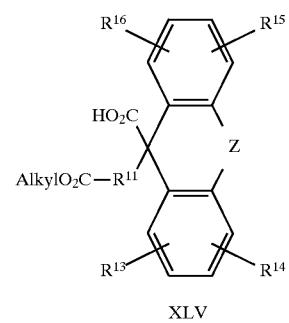

XLV

Amide
Formation
$R^{12}NH_2$

Scheme XVIIA
Preparation of Amide Linked Compounds
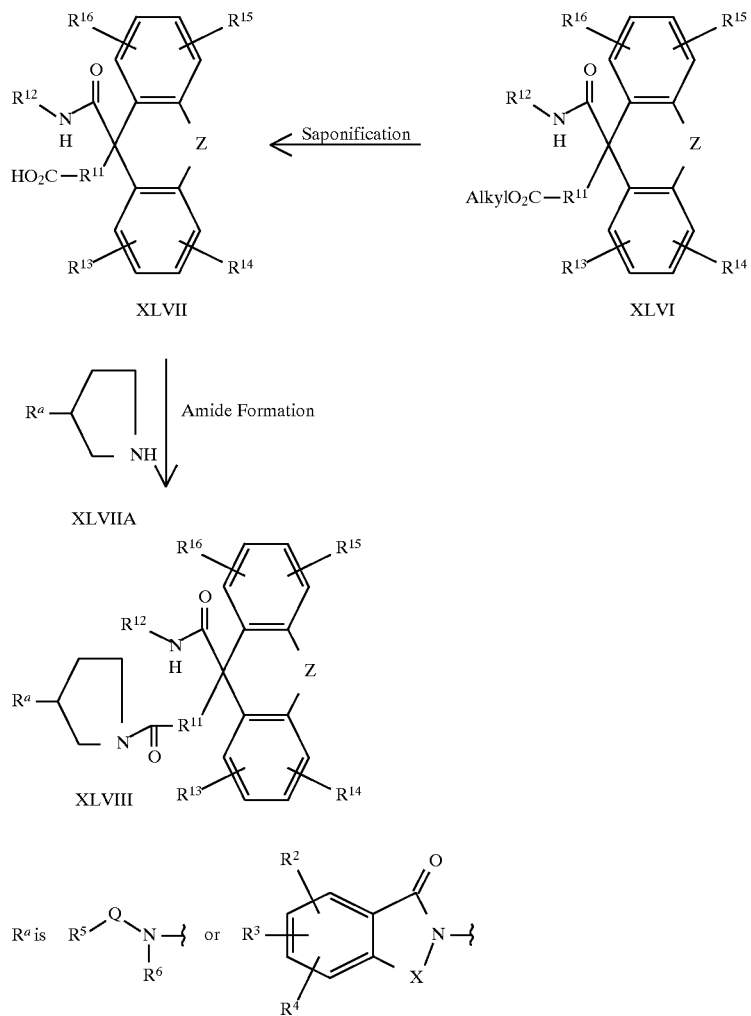
Scheme XVIIB
Preparation of Carbamate and Urea Linked Compounds (where W is H, H)
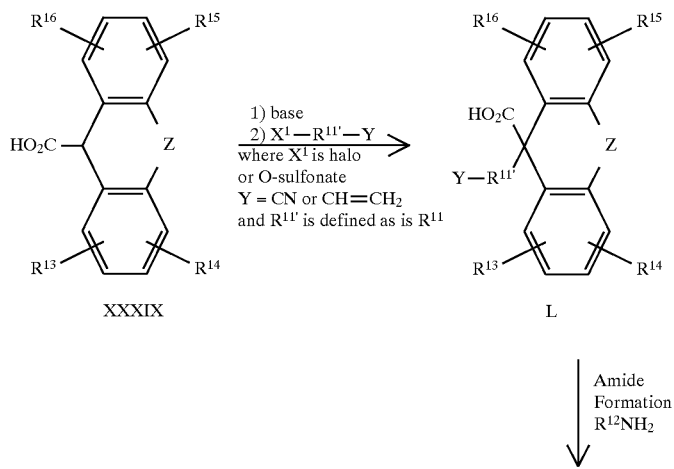

-continued
Scheme XVIIB
Preparation of Carbamate and Urea Linked Compounds (where W is H, H)
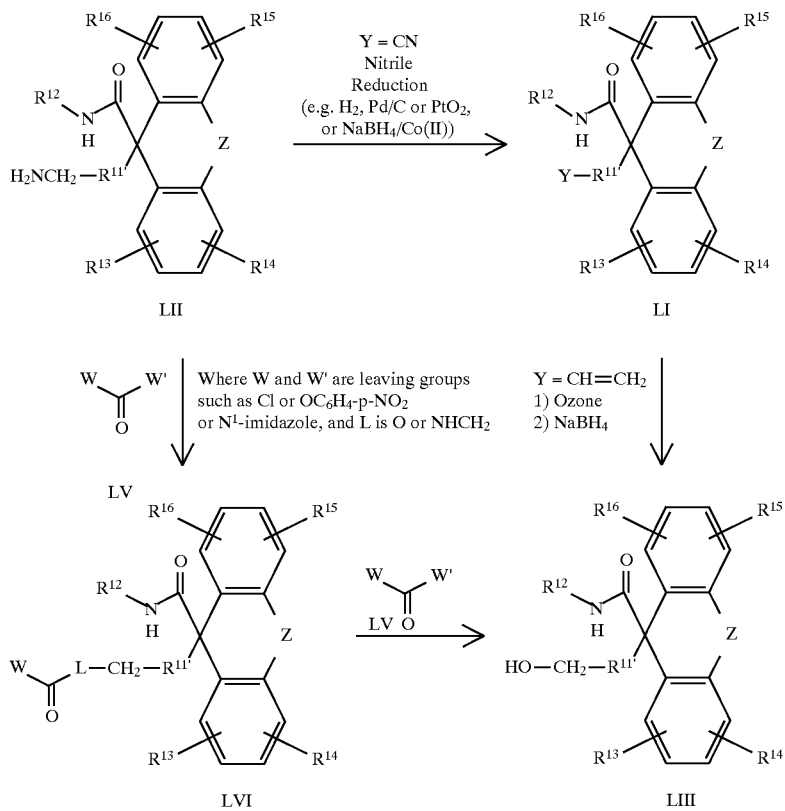
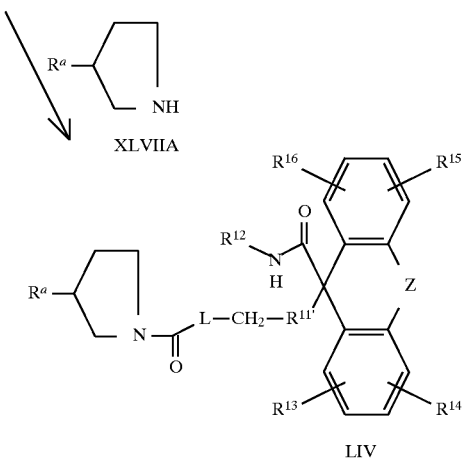
Scheme XVIIIA
Formation of Sulfonamides
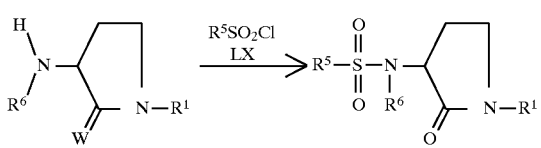
(Reaction in a variety of solvents ($CH_2Cl_2$, THF, pyridine) optionally in the presence of a tertiary amine base, such as pyridine or triethyl amine).
Scheme XVIIIB
Formation of Ureas ($R^5$ is Amino)
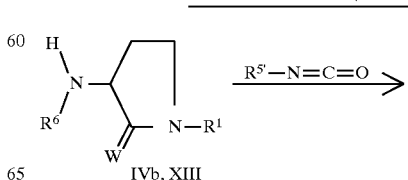

53

-continued
Scheme XVIIIB
Formation of Ureas (R⁵ is Amino)

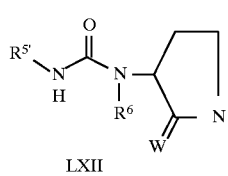

LXII (1 to 10 equiv of R—C=N=O, in aprotic solvent such as toluene, from 0° C. to 150° C.). (R⁵' is alkyl, aryl, heteroaryl or arylalkyl).

Scheme XIXA
General Route to Final Product

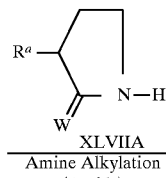

(where $R^1$ is as in XXXIII A–K or any other $R^1$ as defined herein)

Scheme XIXB
General Route to Final Products (I or II)

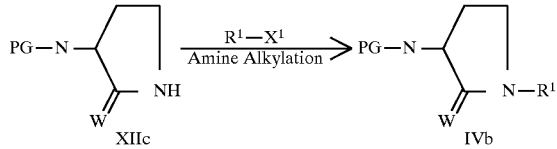

(Where $R^1$ is as in XXXIII A–I or any of the other $R^1$ as defined herein)

54

-continued
Scheme XIXB
General Route to Final Products (I or II)

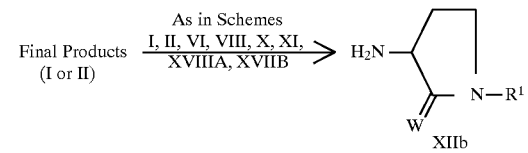

(Example of a protected nitrogen (PG—N) is the t-BuOC=ONH (BOC amino) group, which can be deprotected under mild conditions, such as anhydrous HCl in dioxane or neat trifluoroacetic acid).

Scheme XX
Oxidation of sulfur at the end of the reaction sequence

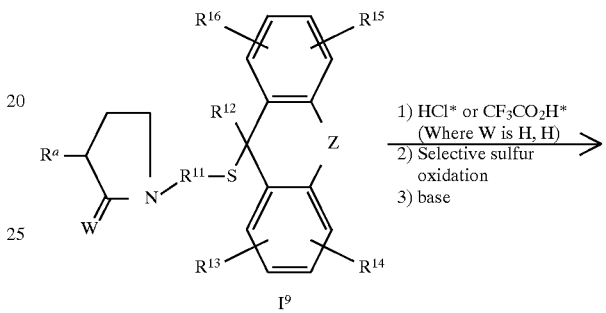

n = 1 or 2

*Acid pretreatment protects basic piperidine from oxidation
($R^a$ is defined as in Scheme XVIIA)

Scheme XXI
Preparation of Halide Intermediates

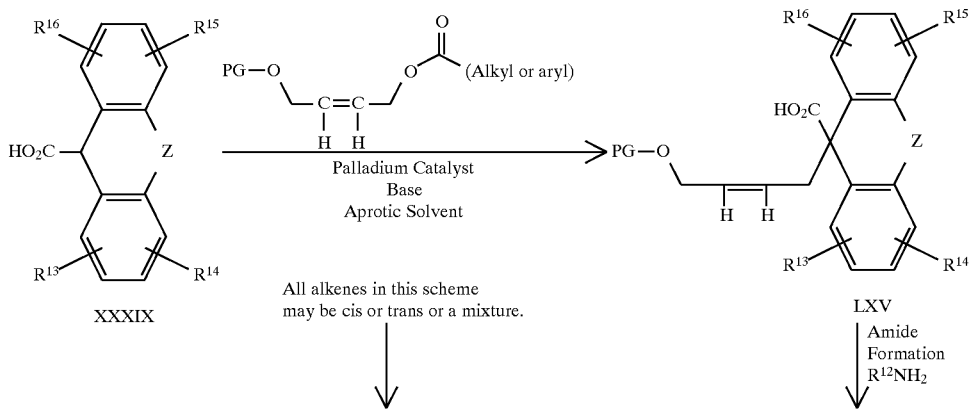

All alkenes in this scheme may be cis or trans or a mixture.

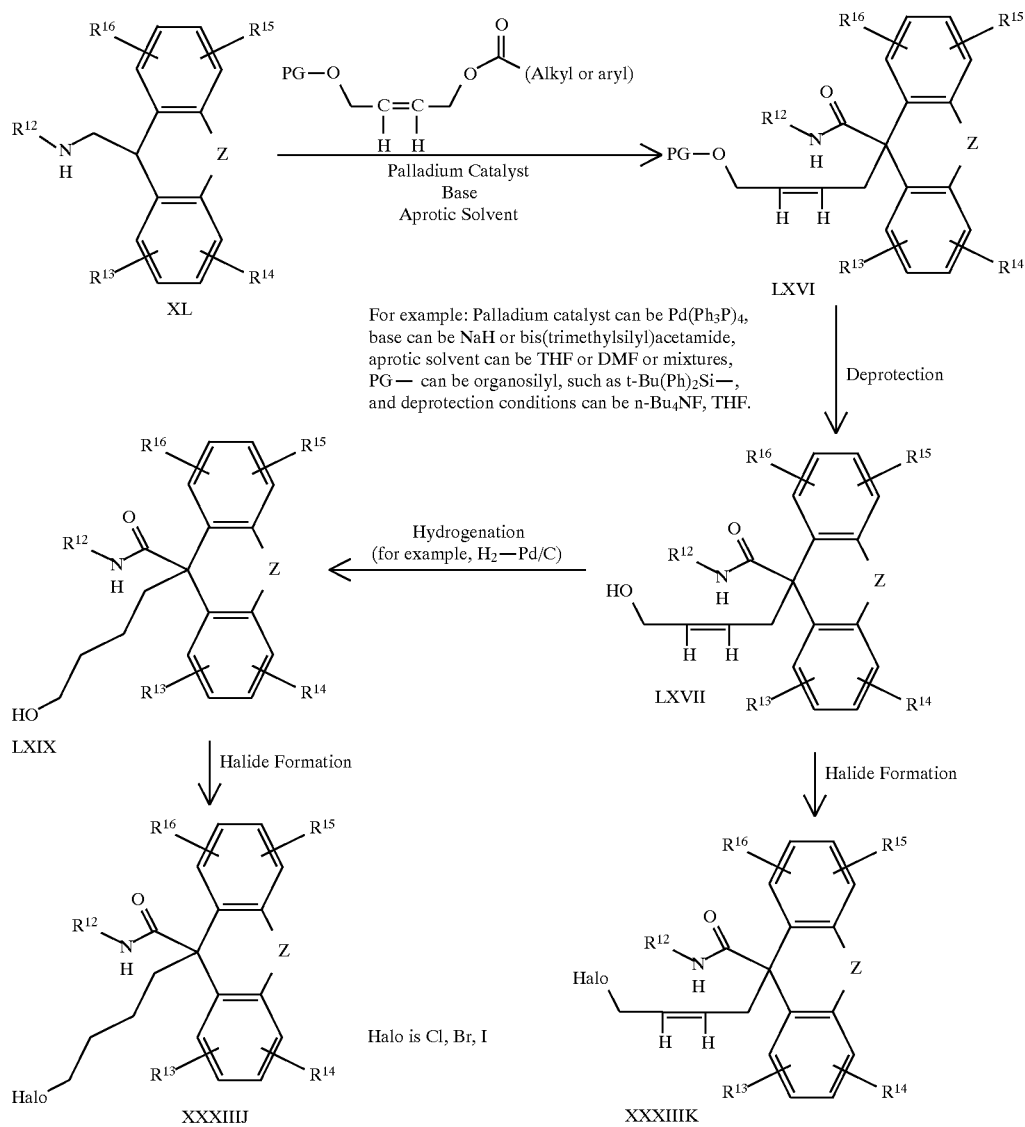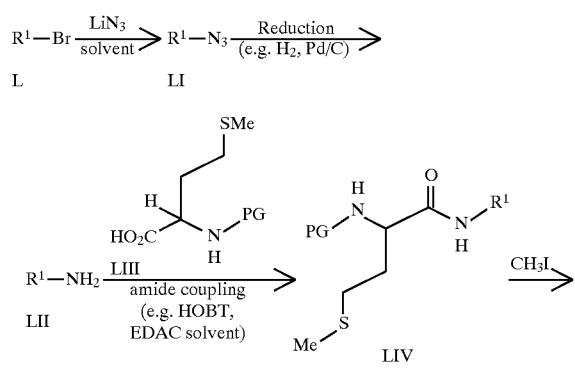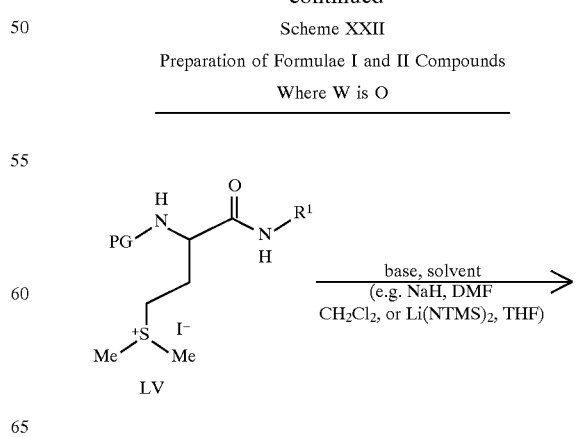

Scheme XXII
Preparation of Formulae I and II Compounds Where W is O

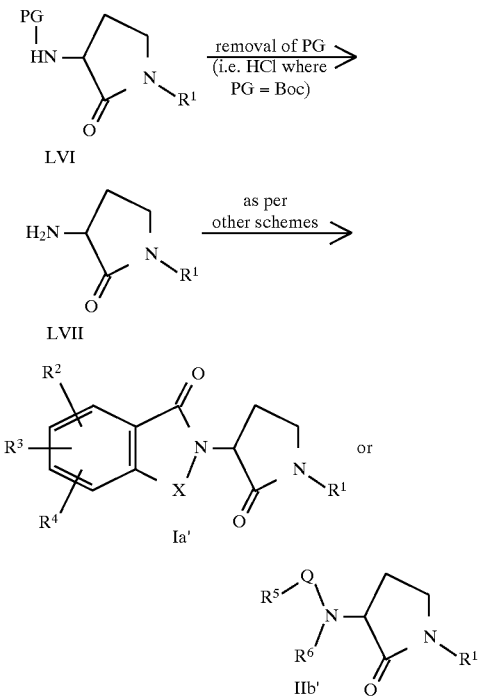

Scheme XXIII
Preparation of N-Oxides of Formulae I and II Compounds

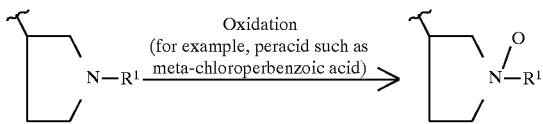

In the above Reaction Schemes XII through XXI, the starting fluorenyl-type acid XXVIII, alcohol XXXV, acids XXXIX and XLII, ketone XLIV, hydride XXXIXA, and amide XL groups may be substituted with corresponding acid, alcohol, ketone, hydride and amide containing fluorenyl type groups as set out in A, B, C and D or indenyl-type groups as set out in E, F, G and/or H to provide an intermediate compound for use in preparing a compound of formula I or II of the invention as per Reaction Schemes I to XXII.

Phthalimide formation (Reaction Schemes I, IV and XXII) may be carried out by heating to about 80° to 150° C. in an oil bath optionally in an inert solvent or by various other procedures known in the art.

Reduction (Reaction Schemes I, XXII) may be carried out by treatment with such reducing agents as zinc in the presence of acetic acid or tin in the presence of hydrochloric acid under an inert atmoshphere (e.g., argon).

Isoindolone formation (Reaction Schemes I, XXII) may be carried out by heating in the range of about 50° to 150° C. in an organic solvent (e.g., toluene, ethanol, dimethylformamide) optionally in the presence of a salt (e.g., potassium carbonate) or a tertiary amine base (e.g., 2,6-di-t-butyl-pyridine or triethylamine).

Amide formation (Reaction Schemes II, VI, VII, VIII, X, XI, XIVA, XV, XVI, XVIA, XVIB, XVIIA, XVIIB, XXI, XXII), may be carried out by a number of methods known in the art. For example, an amine substrate may be treated with (1) an acid halide $R^5C(O)$halo or compound X or XA in an aprotic solvent, optionally in the presence of a tertiary amine base (e.g., triethylamine); (2) the acid halide in the presence of an aqueous base under Schotten-Baumann conditions; (3) a free carboxylic acid ($R^5CO_2H$) in the presence of a coupling agent such as dicyclohexylcarbodiimide (DCC), diisopropyl carbodiimide (DIC) or 1-(3-dimethylamino-propyl)-3-ethylcarbodiimide hydrochloride (WSC), optionally in the presence of 1-hydroxybenzotriazole (HOBT); (4) the free acid in the presence of N, N-carbonyldiimidazole in an aprotic organic solvent followed by the amine substrate; (5) trialkylaluminum (e.g., $Al(CH_3)_3$) in an aprotic solvent, followed by an ester (e.g., $R^5CO_2$alkyl or compound VIII) or (6) mixed anhydride formation, by reacting the acid with an acid chloride (e.g., isobutyl chloroformate or bis-(2-oxo-3-oxazolidinyl)-phosphinic chloride (Bop-Cl)) in the presence of a tertiary amine base (e.g., triethylamine) followed by treatment with the amine substrate.

Mesylate formation (Reaction Scheme II) may be carried out by treatment of the amine-alcohol substrate with methanesulfonyl chloride and triethylamine or pyridine or in an aprotic solvent, such as dichloromethane.

Base cyclization (Reaction Schemes II, VIII, XXII) may be carried out by treatment with a base (e.g., potassium t-butoxide, lithium hexamethyldisilazide ($LiN(TMS)_2$) or sodium hydride) in an inert solvent (e.g., dimethylformamide, tetrahydrofuran, dimethoxymethane, or toluene). Mitsunobu cyclization (Reaction Scheme II) may be carried out by procedures generally known in the art. See, e.g., R. K. Olsen, *J. Org. Chem.*, 49, 3527 (1984); Genin, M. J., et al., *J. Org. Chem.*, 58, 2334–7 (1993).

Alternatively, a mixture of compounds IV and VIII can be converted to compound Ia in a single pot by heating the mixture in a protic solvent (e.g., water, methanol, ethenyl or isopropanol or mixtures thereof) at 100° to 200° C. See, e.g., European patent application 81/26,749, FR 2, 548,666 (1983).

Protection and deprotection (Reaction Schemes III, IV, V, XVI, XVIB, XIXB, XXI, XXII) may be carried out by procedures generally known in the art. See, for example, T. W. Greene, *Protecting Groups in Organic Synthesis*, Second edition, 1991. PG in Scheme V denotes a nitrogen-protecting group. One particularly useful group is tert-butoxy-carbonyl (BOC) which can be derived from the associated anhydride as shown in Scheme IV. BOC-protected amines may typically be deprotected by treatment with acid (e.g., trifluoroacetic acid or hydrochloric acid) in procedures well understood by those having ordinary skill in the art.

Hydrogenolysis (Reaction Schemes III, IV, V) may be carried out with $H_2$ using a balloon apparatus or a Parr Shaker in the presence of a catalyst (e.g., palladium on activated carbon).

Amine/Amide alkylation and arylation (Reaction Schemes III, IV, V, IX, XII, XIXA, XIXB) may be carried out by methods known in the art. Suitable procedures are described in Cortizo, L., *J. Med. Chem.* 34, 2242–2247 (1991). For example, the alkylation or arylation may be carried out by treating the amine substrate with a halide (e.g., $R^1$-halo) or an oxytosylate (e.g., $R^1$-O-tosylate) in an aprotic solvent (e.g., dimethylformamide), optionally in the presence of a tertiary amine (e.g., triethylamine), an inorganic base (e.g., potassium carbonate, NaH), or lithium hexamethyldisilazide).

Reductive amination may be employed as an alternative to the foregoing amine alkylation and arylation procedures where W is H,H when $R^1$, $R^6$ or $R^7$ is $R^9R^{10}CH$— and $R^9$ and $R^{10}$ are each independently hydrogen, alkyl, alkenyl, aryl, heteroaryl, arylalkyl, heteroarylalkyl, cycloalkyl, or cycloalkylalkyl, or $R^9$ and $R^{10}$ together are alkylene (i.e., $R^9R^{10}CH$— forms a cycloalkyl group). Such reductive amination may be carried out by treating the amine with (a) a ketone or aldehyde ($R^9$—C(O)—$R^{10}$), (b) $NaBH_4$, $NaBH_3CN$ or $NaB(acetoxy)_3H$, (c) a protic solvent (e.g., methanol) or a dipolar aprotic solvent (e.g., acetonitrile), and, optionally, (d) an acid (e.g., acetic acid, trifluoroacetic acid, hydrochloric acid, or titanium isopropoxide). When $R^1$ is aryl or heteroaryl, transition metals (e.g., palladium or copper salts or complexes) may be used to promote the arylation reaction.

Alkylation of the isoindolone (Reaction Scheme X, XXII) may be carried out by treatment of the isoindolone with a strong base (i.e. sodium bis(trimethylsilyl)amide or lithium diisopropylamide) followed by an alkyl halide (e.g. $R^8$-halo) or alkyl sulfonate (e.g. $R^8$-tosylate) in an inert solvent (e.g. tetrahydrofuran or dimethoxy-ethane). Alternatively, as seen in Scheme X, amine IVb can be treated under amide formation conditions with a ketone with the structure XB to provide a hydroxylactam XXV, which could be subjected to reduction conditions with such reducing agents as zinc in acetic acid or triethylsilane in trifluoroacetic acid to give $I^a$.

Hydrazinolysis of phthalimides may be carried out by standard means known in the art. See, e.g., T. W. Greene, *Protecting Groups in Organic Synthesis*, Second edition, 1991.

Amide N-alkylation (Reaction Scheme VI, XXII) may be carried out by base treatment (e.g., NaH, KH, $KN[Si(CH_3)_3]_2$, $K_2CO_3$, P4-phosphazene base, or butyl lithium) in an aprotic organic solvent, followed by treatment with $R^6$-halo or $R^6$-O-tosylate. Use of P-phosphazene base is described in T. Pietzonka, D. Seebach, *Angew. Chem. Int. Ed. Engl.* 31, 1481, 1992.

Compound III can also be prepared from compound XX as described by Cortizo, L., *J. Med. Chem.* 34, 2242–2247 (1991).

Dehydration (Scheme VIII) may be carried out employing a strong acid such as hydrochloric acid, sulfuric acid or trifluoroacetic acid.

Hydrogenation (Scheme VIII) may be carried out in the presence of a conventional catalyst such as Pd/C or Pt or Rh under a $H_2$ atmosphere.

The addition reaction shown in Scheme IX may be carried out by treating $IA^1$ with an organometallic reagent XXIV, such as an organolithium or organic magnesium compound where organo is alkyl or aryl.

The deoxygenation or hydrogenation reaction (Scheme IX) is carried out in the presence of a strong acid such as trifluoroacetic acid or boron trifluoride etherate, in the presence of a hydride source such as triethyl silane or tris(trimethylsilyl)silane.

The alkylation in Schemes XII, XIII, XIV, XVI, XVIA, XVIB is carried out in the presence of base such as butyl-lithium or sodium bis(trimethylsilyl)amide. It will be appreciated that $R^{12}$ in $R^{12}Q$ may be any of the $R^{12}$ groups as defined hereinbefore.

Alternatively, the alkylation in the above Schemes can be performed where either or both $Z^1$ or $Z^2$ is a bond, using a palladium catalyzed allylic alkylation procedure. In this reaction, the fluorenyl-type or indenyl-type precursors (compounds XXVIII, XXXVI, XXXVII, XXXIX, XL, XLVII) are reacted with a base (sodium hydride, sodium bis(trimethylsilyl)amide or bis(trimethylsilyl)acetamide), a palladium catalyst (for example $Pd(Ph_3)_4$) and an allylic acetate

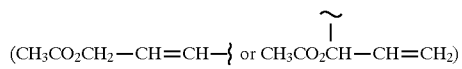

$(CH_3CO_2CH_2$—CH=CH—$\}$ or $CH_3CO_2CH$—CH=$CH_2)$ in an inert solvent (for example THF). This reaction is to introduce either —$R^{12}$ (Scheme XII) or —$R^{11}$—$X^1$ (Schemes XIII, XIV, XVI, XVIA) or —$R^{11}$—OPG (Scheme XVIB, Scheme XXI). The product of this reaction contains either an —$R^{12}$ group or an —$R^{11}$—$X^1$ group (or an —$R^{11}$—OPG group) which begins with —$CH_2$—CH=CH—}. Saturation of the alkene in $R^{11}$ or $R^{12}$ can be accomplished by standard catalytic hydrogenation conditions.

With respect to Scheme XII, the $LiAlH_4$ reduction, Swern oxidation, Wittig olefination and halogenation/sulfonation reactions are conventional reactions well known to those skilled in the art.

The sulfur oxidation in Schemes XIII, XVI and XVIII is carried out as follows.

Sulfides of structures XXXVI, XXXVIII, XXXIIIE and $I^9$ can be selectively oxidized to sulfoxides by 1 molar equivalent of reagents known in the art, such as 30% $H_2O_2$, $NaIO_4$, and peracids (e.g., meta-chloroperbenzoic acid). The resulting sulfoxides can be further transformed to corresponding sulfones by another molar equivalent or excess of 30% $H_2O_2$, $KMnO_4$, $KHSO_5$, or peracids (e.g., meta-chloroperbenzoic acid). Alternatively, the sulfones can be directly prepared from sulfides with 2 molar equivalents or more of oxidizing agents, such as 30% $H_2O_2$ and peracids (e.g., meta-chloroperbenzoic acid). In cases where an amine (such as a pyrrolidine in $I^9$) is present during the oxidation, the basic nitrogen may be protected by pretreatment with an acid such as HCl or $CF_3CO_2H$ (see Scheme XIX).

To prepare examples where $Z^1$ or $Z^2$ is —CHOH, the compounds I and II where $Z^1$ or $Z^2$ is C=O can be reduced with a hydride reagent, for example $NaBH_4$.

The compounds of the invention may be employed in preventing, stabilizing or causing regression of atherosclerosis in a mammalian species by administering a therapeutically effective amount of a compound to decrease the activity of MTP.

The compounds of the invention can be tested for MTP inhibitory activity employing the procedures set out in U.S. application Ser. No. 117,362 filed Sep. 3, 1993, employing MTP isolated from one of the following sources:

(1) bovine liver microsomes, (2) HepG$_2$ cells (human hepatoma cells) or (3) recombinant human MTP expressed in baculovirus.

The compounds of the invention may also be employed in lowering serum lipid levels, such as cholesterol or triglyceride (TG) levels, in a mammalian species, by administering a therapeutically effective amount of a compound to decrease the activity of MTP.

The compounds of the invention may be employed in the treatment of various other conditions or diseases using agents which decrease activity of MTP. For example, compounds of the invention decrease the amount or activity of MTP and therefore decrease serum cholesterol and TG levels, and TG, fatty acid and cholesterol absorption and thus are useful in treating hypercholesterolemia, hypertriglyceridemia, hyperlipidemia, pancreatitis, hyperglycemia and obesity.

The compounds of the present invention are agents that decrease the activity of MTP and can be administered to various mammalian species, such as monkeys, dogs, cats, rats, humans, etc., in need of such treatment. These agents can be administered systemically, such as orally or parenterally.

The agents that decrease the activity or amount of MTP can be incorporated in a conventional systemic dosage form, such as a tablet, capsule, elixir or injectable formulation. The above dosage forms will also include the necessary physiologically acceptable carrier material, excipient, lubricant, buffer, antibacterial, bulking agent (such as mannitol), antioxidants (ascorbic acid or sodium bisulfite) or the like. Oral dosage forms are preferred, although parenteral forms are quite satisfactory as well.

The dose administered must be carefully adjusted according to the age, weight, and condition of the patient, as well as the route of administration, dosage form and regimen, and the desired result. In general, the dosage forms described above may be administered in amounts of from about 5 to about 500 mg per day in single or divided doses of one to four times daily.

The following Examples represent preferred embodiments of the invention. All temperatures are in °C. unless indicated otherwise.

EXAMPLE 1

9-[4-[3-[(2-Phenoxybenzoyl)amino]-1-pyrrolidinyl]-butyl]-N-(2,2,2-trifluoroethyl)-9H-fluorene-9-carboxamide monohydrochloride

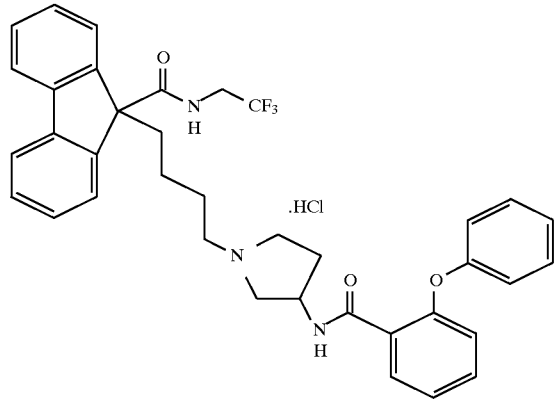

A.

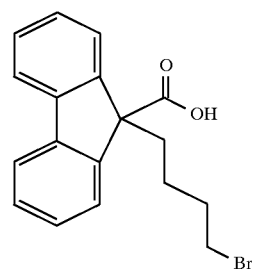

To a solution of 9-fluorenecarboxylic acid (50 g, 240 mmol) in THF (1200 mL) at 0° C. was added dropwise a solution of n-butyllithium (2.5M, 211 mL, 530 mmol) in THF. The yellow reaction was stirred at 0° C. for 1 h, then 1,4-dibromobutane (31.3 mL, 260 mmol) was added dropwise over 30 min. The reaction was stirred at 0° C. for 30 min, then the reaction was warmed to RT for 30 h. The reaction was extracted with water (3×750 mL). The combined aqueous layers were extracted with ethyl ether (800 mL). The aqueous layer was made acidic with HCl solution (1N, 500 mL), then extracted with dichloromethane (3×750 mL). The combined organic layers were dried over MgSO$_4$. Evaporation gave title compound (71 g, 85%) as a white solid.

B.

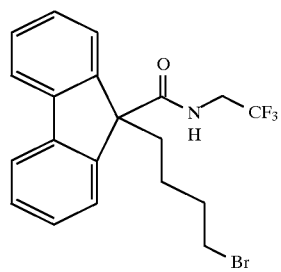

To a solution of Part A acid (60 g, 173 mmol) and DMF (100 μL) in CH₂Cl₂ (600 mL) under argon at 0° C. was added oxalyl chloride (104 mL, 2.0M in CH₂Cl₂, 208 mmol) dropwise. The reaction was stirred at 0° C. for 10 min, then warmed to RT and stirred for 1.5 h. The reaction was concentrated in vacuo to give the crude acid chloride as a yellow oil. To a suspension of 2,2,2-trifluoroethylamine hydrochloride (25.9 g, 191 mmol) in CH₂Cl₂ (500 mL) at 0° C. under argon was added triethylamine (73 mL, 521 mmol) followed by dropwise addition of a solution of the crude acid chloride in CH₂Cl₂ (15 mL). The reaction was stirred at 0° C. for 1 h, diluted with CH₂Cl₂ (500 mL), and washed with water (2×300 mL), 1N HCl (2×300 mL), saturated NaHCO₃ (2×300 mL), and brine (2×300 mL), then dried over MgSO₄. Evaporation gave 80 g of a oil which was purified by flash chromatography on silica gel (2.5 kg). The crude product was loaded in a mixture of CH₂Cl₂ and hexane, and eluted with a step gradient of 10% EtOAc/hexane (4L) to 15% EtOAc/hexane (2L) to 20% EtOAc/hexane (4L). Pure fractions were combined and evaporated to give title compound (52.5 g, 71%) as a white solid (mp 88°–92° C.).

C.

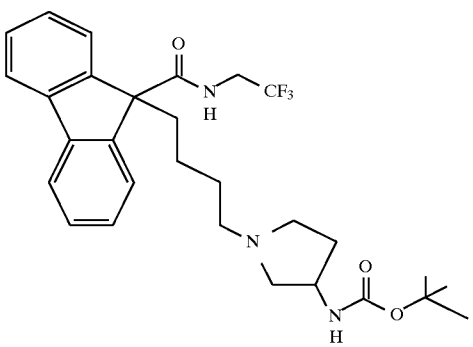

A mixture of Part B compound (732 mg, 1.72 mmol), 3-(tert-butoxycarbonylamino)-pyrrolidine (383 mg, 2.06 mmol), and anhydrous potassium carbonate (356 mg, 2.58 mmol) in DMF (5 mL) was heated at 50° C. under argon overnight (18 h), cooled to RT, and the solvent removed under high vacuum. The residue was partitioned between CH₂Cl₂ (20 mL) and water (5 mL). The organic layer was washed with water (5 mL), dried over Na₂SO₄, and evaporated to give 1.2 g of an orange solid. The crude product was purified by flash chromatography on silica gel (70 g) eluting with 5% MeOH/CH₂Cl₂ to provide title compound (673 mg, 74%) as a white foam.

D.

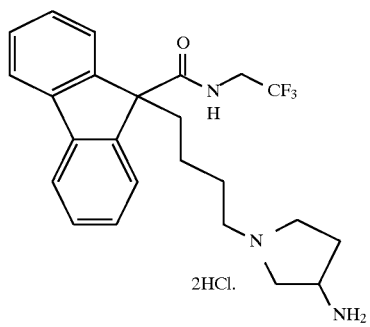

To a solution of Part C compound (625 mg, 1.18 mmol) in dioxane (2 mL) was added 4N HCl in dioxane (2 mL, 8 mmol). The clear solution was stirred at RT for 3 h, concentrated in vacuo, and pumped under high vacuum overnight to give title compound (646 mg, >100%) as a white foamy solid.

E. 2-Phenoxybenzoic acid chloride

To a solution of 2-phenoxybenzoic acid (Aldrich) (500 mg, 2.33 mmol) and DMF (1 drop) in dichloromethane (10 mL) at RT was added dropwise a solution of oxalyl chloride in dichloromethane (2.0M, 1.28 mL, 2.56 mmol). Bubbling of escaping gasses continued for 10 min after addition. The reaction was stirred at RT for 60 min, then concentrated in vacuo to give title compound as an oil.

F. 9-[4-[3-[(2-Phenoxybenzoyl)amino]-1-pyrrolidinyl]-butyl]-N-(2,2,2-trifluoroethyl)-9H-fluorene-9-carboxamide, monohydrochloride A solution of Part D compound (350 mg, 0.696 mmol) in CH₂Cl₂ (2 mL) was cooled to 0° C. under argon. Triethylamine (385 μL, 2.78 mmol) was added, which gave a cloudy mixture. A solution of Part E acid chloride in CH₂Cl₂ (1.5 mL) was added and the reaction mixture was stirred at 0° C. for 10 min, diluted with CH₂Cl₂ (2 mL), washed with water (2 mL) and saturated NaHCO₃ (2 mL), dried over Na₂SO₄, and then evaporated to give 450 mg of a gold-colored gum. The crude product was purified by flash chromatography on silica gel (50 g) eluting with 4% MeOH/CH₂Cl₂ to provide 360 mg of the free amine as a white foam.

To a solution of the free amine in THF (3 mL) was added 1.1N HCl in Et₂O (1.0 mL, 1.1 mmol). The reaction mixture was concentrated in vacuo, and the residue was triturated with Et₂O. The resulting foam was dried in a vacuum oven (50° C., 0.2 torr) overnight to provide title compound (380 mg, 82%) as a foamy tan solid.

MS (ES, +ions) m/z 628 (M+H) Anal. Calc'd for $C_{37}H_{37}F_3N_3O_3 + 0.6$ H₂O: C, 65.84; H, 5.70; N, 6.23; F, 8.44 Found: C, 66.20; H, 5.60; N, 6.13; F, 8.04.

EXAMPLE 2

9-[4-[3-(Benzoylamino)-1-pyrrolidinyl]butyl]-N-(2,2,2-trifluoroethyl)-9H-fluorene-9-carboxamide, monohydrochloride To a mixture of Example 1 compound (273 mg, 0.543 mmol) and triethylamine (300 μL, 2.17 mmol) in CH₂Cl₂ (2 mL) at 0° C. under argon was added benzoyl chloride (70 μL, 0.597 mmol). The reaction mixture was stirred at 0° C. for 15 min, diluted with CH₂Cl₂ (3 mL), washed with water (1 mL) and saturated NaHCO₃ (2 mL), and then dried over Na₂SO₄. Evaporation of the filtrate gave a brown foam, which was purified by flash chromatography on silica gel (60 g) eluting with 3% MeOH/CH₂Cl₂ to provide 196 mg of product as the free amine.

A portion of the desired product (176 mg) was dissolved in MeOH (2 mL) and a solution of 1.1N HCl/Et₂O (0.6 mL, 0.66 mmol) was added. The solution was concentrated in vacuo and the residue was triturated with Et₂O to give a foamy solid, which was pumped under high vacuum overnight to afford title compound (175 mg, 62%) as a foamy white solid.

MS (ES, +ions) m/z 536 (M+H) Anal. Calc'd for $C_{31}H_{33}Cl_3N_3O_2 + 0.4$ H₂O: C, 64.28; H, 5.88; N, 7.25; Cl, 6.12; F, 9.84 Found: C, 64.27; H, 5.93; N, 7.29; Cl, 5.71; F, 9.73.

EXAMPLE 3

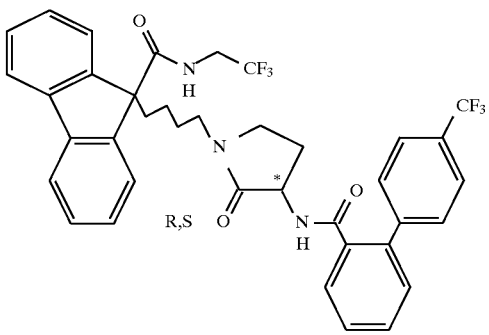

9-[4-[2-Oxo-3-[[[4'-(trifluoromethyl)[1,1'-biphenyl]-2-yl]carbonyl]-amino]-1-pyrrolidinyl]butyl]-N-(2,2,2-trifluroethyl)-9H-fluorene-9-carboxamide

A.

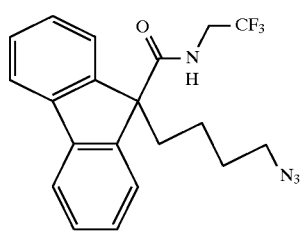

A slurry of Example 1 Part B bromide (3.037 g, 7.12 mmol) and NaN$_3$ (2.26 g, 34.7 mmol) in DMF (15 mL) was heated at 50° C. for 3 hours and then at 95° C. for 2 hours. The mixture was cooled to room temperature and partitioned between EtOAc and H$_2$O. The organic layer was washed successively with H$_2$O, 1N HCl, H$_2$O, and brine, then dried (Na$_2$SO$_4$), filtered and stripped to give a yellow oil which slowly solidified. Recrystallization from hexane afforded title azide compound (2.198 g) as a white solid. An additional 212 mg of material was obtained from the mother liquor to give a total of 2.41 g (87%) of title azide.

mp: 84°–86° C.

B.

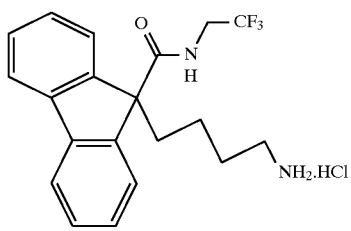

A solution of Part A azide (2.253 g, 5.8 mmol) in MeOH (40 mL) was hydrogenated (balloon) over palladium (10% Pd on carbon, 250 mg) at room temperature for 1 hour. The mixture was filtered through Celite and the filtrate was stripped, redissolved in MeOH, and treated with 4N HCl in dioxane. Trituration with Et$_2$O followed by collection of the precipitate and drying in vacuo afforded title compound (2.090 g, 90%) as a grayish white solid.

mp: 200°–202° C.

C.

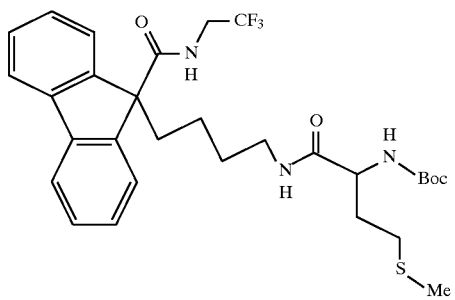

A solid mixture of Part B compound (2.048 g, 5.1 mmol), N-Boc-D,L-methionine (1.280 g, 5.1 mmol), and HOBT.xH$_2$O (693 mg) was slurried in CH$_2$Cl$_2$ and subsequently treated with N-methylmorpholine (0.9 mL, 828 mg, 8.2 mmol) followed by ethyl-3-(3-dimethylamino)propyl carbodiimide .HCl salt (EDAC) (1.083 g, 5.6 mmol). After stirring at room temperature for 18 hours, the homogeneous mixture was partitioned between EtOAc/Et$_2$O and 1N HCl. The organic layer was washed with H$_2$O, 50% saturated NaHCO$_3$, and brine, then dried (Na$_2$SO$_4$), filtered and stripped to give racemic title compound (2.972 g, 98%) as a foam.

TLC: R$_f$ 0.44 (6/4-EtOAc/hexanes).

D.

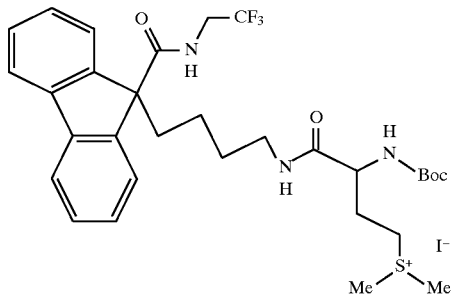

Part C compound (2.902 g, 4.88 mmol) was dissolved in CH$_3$I (35 mL) and stirred at room temperature for 2 days. The solvent was stripped, then triturated and stripped from hexane twice to give crude title compound (3.74 g, 104% of theory) as a pale yellow solid which was used directly in the next reaction without further purification.

E.

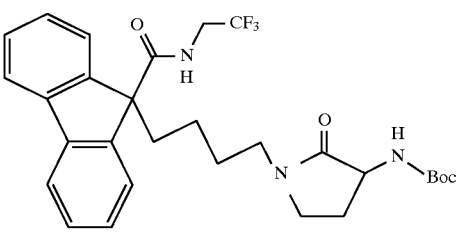

A solution of Part D sulfonium salt (3.069 g, 4.17 mmol) in DMF (20 mL) and CH$_2$Cl$_2$ (22 mL) at 0° C. was treated all at once with solid NaH (60% in mineral oil, 400 mg, 240 mg pure, 10.0 mmol). After stirring at 0° C. for 1.5 hours and at room temperature for 1.5 hours, the mixture was quenched with 0.5N HCl and extracted with EtOAc. The EtOAc extract was washed twice with H₂O, once with saturated NaHCO₃, and once with brine, then dried (Na₂SO₄), filtered and stripped. Flash chromatography (Merck SiO₂, 7/3-EtOAc/hexanes) afforded title compound (1.774 g, 78%) as a white foam.

TLC: $R_f$ 0.21 (6/4-EtOAc/hexane).

F.

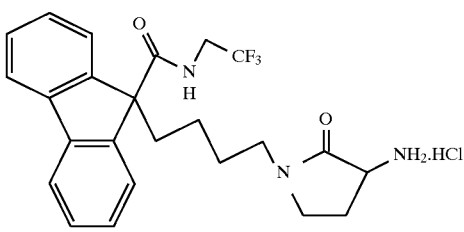

A solution of Part E compound (1.752 g, 3.2 mmol) in 1,4-dioxane (8 mL) was treated with 4N HCl in 1,4-dioxane (5 mL). After 5 hours, the solvent was stripped and the residue was azeotroped twice from CH₂Cl₂/Et₂O and triturated from Et₂O/hexane. The solid was collected by filtration and dried in vacuo to give title compound (1.576 g, 102% of theory) as a white solid.

G.

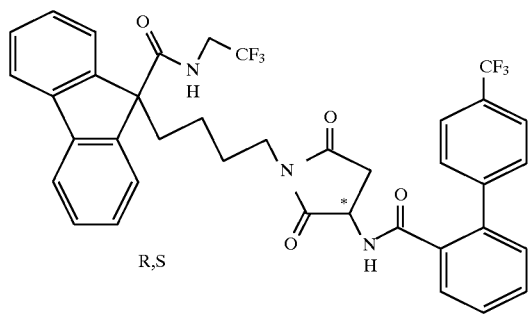

A solid mixture of Part F compound (250 mg, 0.52 mmol), 4'-(trifluoromethyl)-2-biphenylcarboxylic acid (145 mg, 0.54 mmol), and HOBT.xH₂O (70 mg) was slurried in CH₂Cl₂ (5 mL) and subsequently treated with N-methyl morpholine (86 μL, 79 mg, 0.78 mmol) followed by EDAC (111 mg, 0.58 mmol). After stirring at room temperature for 18 hours, the mixture was partitioned between EtOAc and 1N HCl. The EtOAc extract was washed successively with H₂O, saturated NaHCO₃ and brine, then dried (Na₂SO₄), filtered and stripped. Flash chromatography (Merck SiO₂, 8/2-EtOAc/hexanes) afforded title compound (310 mg, 86%) as a white foam.

TLC: $R_f$ 0.21 (8/2-EtOAc/hexanes) MS: (M+H)⁺ @694; (M−H)⁻ 692; (M+NH₄)⁺ 711 HPLC: YMC S3 ODS column (6.0×150 mm); Eluted with 0% to 100% B, 30 minute gradient, (A=90% H₂O-10% MeOH-0.2% H₃PO₄ and B=10% H₂O-90% MeOH-0.2% H₃PO₄) flow rate at 1.5 ml/min detecting at 220 nm; $t_R$=30.98 min (98.1%). Microanalysis Calc'd for C₃₈H₃₃F₆N₃O₃+0.13 CH₂Cl₂: C, 64.96; H, 4.76; N, 5.96; F, 16.17; Cl, 1.35 Found: C, 64.86; H, 4.80; N, 5.89; F, 16.22; Cl 1.34.

EXAMPLE 4

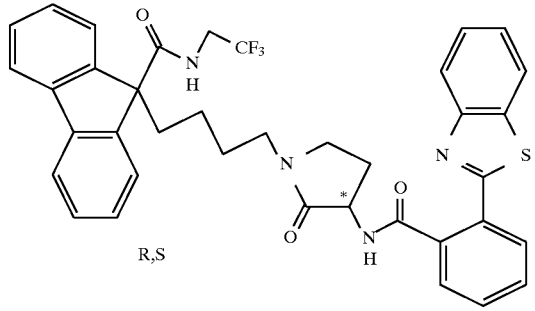

9-[4-[3-[[2-(2-Benzothiazolyl)benzoyl]amino]-2-oxo-1-pyrrolidinyl]butyl]-N-(2,2,2-trifluoroethyl)-9H-fluorene-9-carboxamide A slurry of Example 3 Part F amine hydrochloride (200 mg, 0.415 mmol),

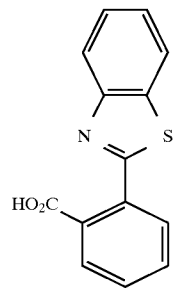

(98 mg, 0.38 mmol), and HOBT.xH₂O (56 mg) in CH₂Cl₂ (5 mL) was treated successively with N-methyl morpholine (70 μL, 65 mg, 0.65 mmol) and EDAC (89 mg, 0.46 mmol) at room temperature. After 18 hours, the mixture was partitioned between EtOAc and saturated NaHCO₃. The EtOAC extract was washed successively with H₂O, 1N HCl, and brine, then dried (Na₂SO₄), filtered, and stripped repeatedly from CH₂Cl₂ to give title compound (249 mg, 95%) as a white foam.

TLC: $R_f$ 0.19 (EtOAc) MS: (M+H)⁺ @683; (M−H)⁻ 681 HPLC: YMC S3 ODS column (6.0×150 mm); Eluted with 40% to 100% B, 20 minute gradient, (A=90% H₂O-10% MeOH-0.2% H₃PO₄ and B=10% H₂O-90% MeOH-0.2% H₃PO₄) flow rate at 1.5 ml/min detecting at 254 nm; $t_R$=18.9 min (96.6%). Microanalysis Calc'd for C₃₈H₃₃F₃N₄O₃S+ 0.09 CH₂Cl₂: C, 66.27; H, 4.84; N, 8.12; F, 8.26; S, 4.64; Cl, 0.92 Found: C, 65.92; H, 3.92; N, 7.81; F, 7.98; S, 4.56; Cl, 0.70.

EXAMPLE 5

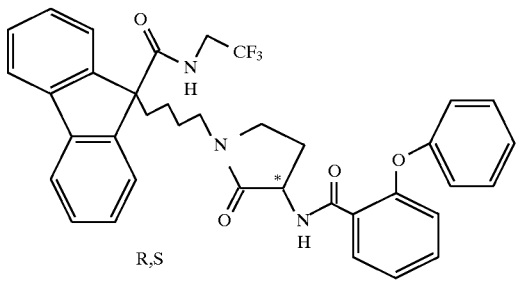

9-[4-[2-Oxo-3-[(2-phenoxybenzoyl)amino]-1-pyrrolidinyl]butyl]-N-(2,2,2-trifluoroethyl)-9H-fluorene-9-carboxamide A slurry of Example 3 Part F amine hydrochloride (200 mg, 0.415 mmol),

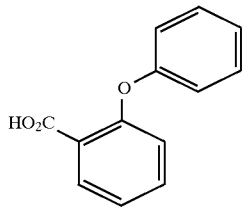

(85 mg, 0.40 mmol), and HOBT.xH$_2$O (56 mg) in CH$_2$Cl$_2$ (7 mL) was treated successively with N-methyl morpholine (70 μL, 65 mg, 0.65 mmol) and EDAC (89 mg, 0.46 mmol) at room temperature. After 22 hours, the mixture was partitioned between EtOAc and saturated NaHCO$_3$. The EtOAC extract was washed successively with H$_2$O, 1N HCl, and brine, then dried (Na$_2$SO$_4$), filtered, and stripped repeatedly from CH$_2$Cl$_2$ to give title compound (224 mg, 87%) as a white foam.

TLC: R$_f$ 0.46 (EtOAc) MS: (M+H)$^+$ @642; (M−H)$^-$ 640 HPLC: YMC S3 ODS column (6.0×150 mm); Eluted with 40% to 100% B, 20 minute gradient, (A=90% H$_2$O-10% MeOH-0.2% H$_3$PO$_4$ and B=10% H$_2$O-90% MeOH-0.2% H$_3$PO$_4$) flow rate at 1.5 ml/min detecting at 254 nm; t$_R$=19.7 min (100%). Microanalysis Calc'd for C$_{37}$H$_{34}$F$_3$N$_3$O$_4$: C, 69.26; H, 5.34; N, 6.55; F, 8.88 Found: C, 68.92; H, 5.25; N, 6.42; F, 8.70.

EXAMPLE 6

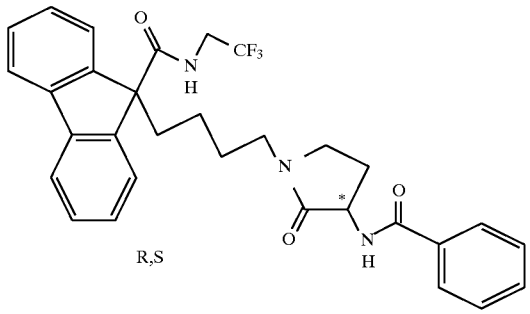

9-[4-[3-(Benzoylamino)-2-oxo-1-pyrrolidinyl]butyl]-
N-(2,2,2-trifluoroethyl)-9H-fluoroene-9-carboxamide A solution of Example 3 Part F amine hydrochloride (200 mg, 0.415 mmol) and triethylamine (TEA) (200 μL, 145 mg, 1.43 mmol) in CH$_2$Cl$_2$ (4 mL) at 0° C. was treated with benzoyl chloride (48 μL, 58 mg, 0.41 mmol). After 45 minutes, the mixture was quenched with saturated NaHCO$_3$ and extracted with EtOAc. The EtOAc extract was washed successively with H$_2$O, 1N HCl, H$_2$O, and brine, then dried (Na$_2$SO$_4$), filtered and stripped to give title compound (231 mg, 98%) as a white foam.

TLC: R$_f$ 0.35 (EtOAc) MS: (M+H)$^+$ @550; (M−H)$^-$ 548 HPLC: YMC S3 ODS column (6.0×150 mm); Eluted with 40% to 100% B, 20 minute gradient, (A=90% H$_2$O-10% MeOH-0.2% H$_3$PO$_4$ and B=10% H$_2$O-90% MeOH-0.2% H$_3$PO$_4$) flow rate at 1.5 ml/min detecting at 254 nm; t$_R$=16.2 min (96.7%). Microanalysis Calc'd for C$_{31}$H$_{30}$F$_3$N$_3$O$_3$+0.2 EtOAc: C, 67.34; H, 5.62; N, 7.41; F, 9.59 Found: C, 67.15; H, 5.55; N, 7.13; F, 9.73.

EXAMPLE 7

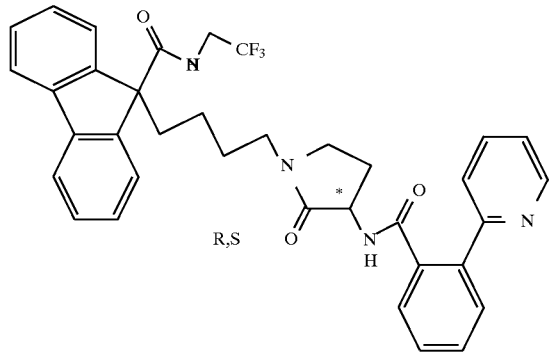

9-[4-[2-Oxo-3-[[2-(2-pyridinyl)benzoyl]amino]-1-pyrrolidinyl]butyl]-
N-(2,2,2-trifluoroethyl)-9H-fluorene-9-carboxamide A slurry of Example 3 Part F amine hydrochloride (202 mg, 0.419 mmol),

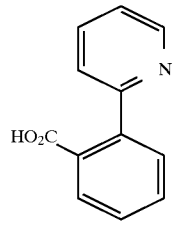

(88 mg, 0.44 mmol), and 1-hydroxy-7-azabenzotriazole (HOAT) (55 mg) in CH$_2$Cl$_2$ (3 mL) was treated successively with N-methyl morpholine (56 μL, 52 mg, 0.51 mmol) and EDAC (87.5 mg, 0.46 mmol) at room temperature. After 18 hours, the mixture was partitioned between EtOAc and saturated NaHCO$_3$. The EtOAc extract was washed successively with H$_2$O and brine, then dried (Na$_2$SO$_4$), filtered, and stripped. The residue was flash chromatographed (Merck SiO2, 5/95-MeOH/CH$_2$Cl$_2$ as eluant) to give title compound (259 mg, 94%) as a white foam.

TLC: R$_f$ 0.47 (1/9-MeOH/CH$_2$Cl$_2$) MS: (M+H)$^+$ @627 HPLC: YMC S3 ODS column (6.0×150 mm); Eluted with 40% to 100% B, 20 minute gradient, (A=90% H$_2$O-10% MeOH-0.2% H$_3$PO$_4$ and B=10% H$_2$O-90% MeOH-0.2% H$_3$PO$_4$) flow rate at 1.5 ml/min detecting at 254 nm; t$_R$=11.6 min (98.9%). Microanalysis Calc'd for C$_{36}$H$_{33}$F$_3$N$_4$O$_3$+0.35 CH$_2$Cl$_2$: C, 66.51; H, 5.18; N, 8.54; F, 8.68 Found: C, 66.88; H, 5.07; N, 8.36; F, 7.91.

EXAMPLE 8

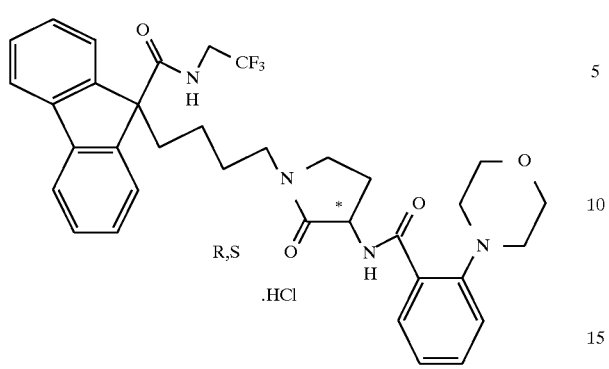

9-[4-[3-[[2-(4-Morpholinyl)benzoyl]amino]-2-oxo-1-pyrrolidinyl]butyl]-
N-(2,2,2-trifluoroethyl)-9H-fluorene-9-carboxamide, monohydrochloride A slurry of Example 3 Part F amine hydrochloride (200 mg, 0.415 mmol),

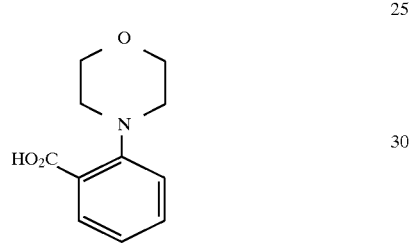

(111 mg, 0.53 mmol), and HOAT (53 mg) in CH$_2$Cl$_2$ (5 mL) was treated successively with N-methyl morpholine (100 μL, 93 mg, 0.91 mmol) and EDAC (90 mg, 0.47 mmol) at room temperature. After 20 hours, the mixture was partitioned between EtOAc and saturated NaHCO$_3$. The EtOAC extract was washed successively with H$_2$O and brine, then dried (Na$_2$SO$_4$), filtered, and stripped to give an oil. The residue was flash chromatographed (Merck SiO$_2$, 5/95-MeOH/CH$_2$Cl$_2$ as eluant) to give the free base of title compound (141 mg, 53%) as pale yellow oil. The oil was dissolved in 1,4-dioxane (2 mL), treated with 4N HCl in 1,4-dioxane (150 μL) and added via cannula to rapidly swirling Et$_2$O (30 mL). The precipitate was collected by filtration and dried in vacuo to give title compound (101 mg, 35% from Example 3 Part F compound) as a pink solid.

TLC: R$_f$ 0.64 (1/9-MeOH/CH$_2$Cl$_2$) MS: (M+H)$^+$ @635 HPLC: YMC S3 ODS column (6.0×150 mm); Eluted with 40% to 100% B, 20 minute gradient, (A=90% H$_2$O-10% MeOH-0.2% H$_3$PO$_4$ and B=10% H$_2$O-90% MeOH-0.2% H$_3$PO$_4$) flow rate at 1.5 ml/min detecting at 254 nm; t$_R$=16.9 min (98.7%).

The following Examples represent preferred embodiments of the invention and may be prepared employing procedures described herein.

EXAMPLE 8A

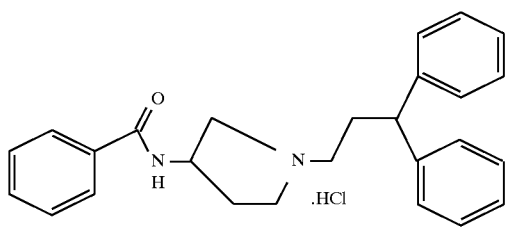

EXAMPLE 8B

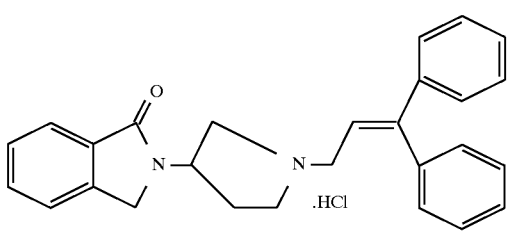

EXAMPLE 8C

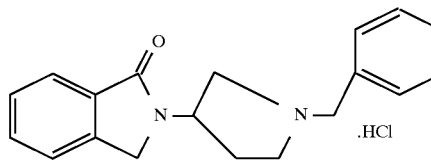

EXAMPLE 8D

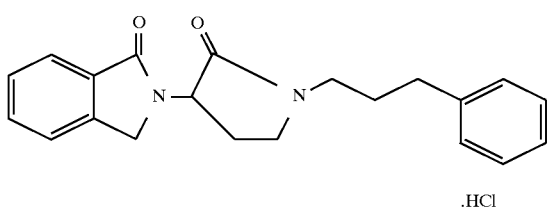

EXAMPLE 8E

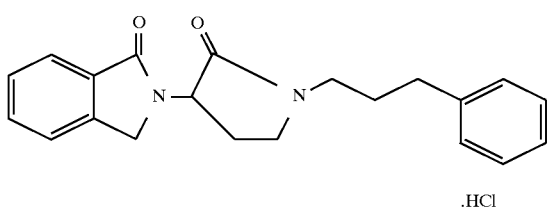

73
EXAMPLE 8F
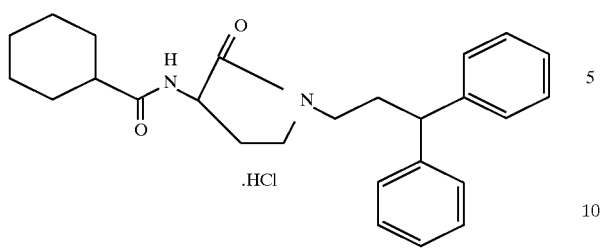
.HCl
EXAMPLE 9
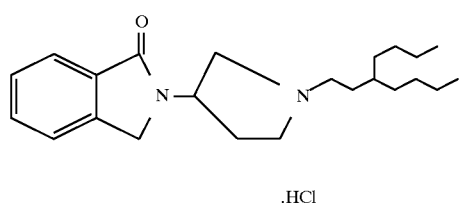
.HCl
EXAMPLE 10
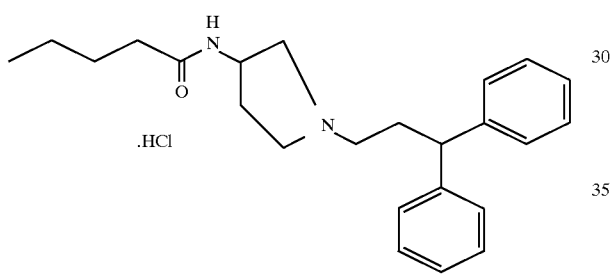
.HCl
EXAMPLE 11
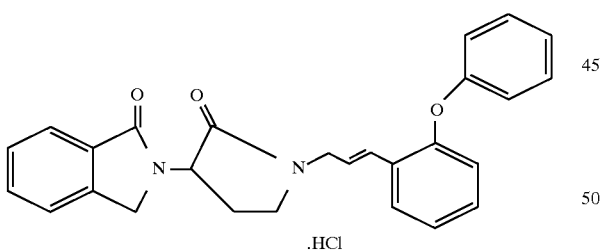
.HCl
EXAMPLE 12
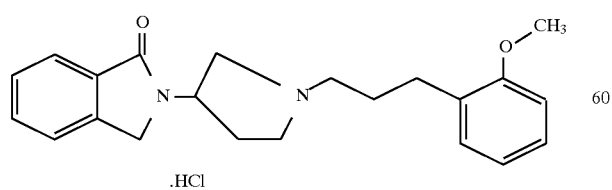
.HCl
74
EXAMPLE 13
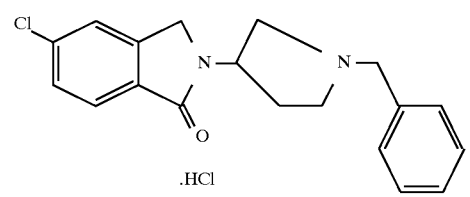
.HCl
EXAMPLE 14
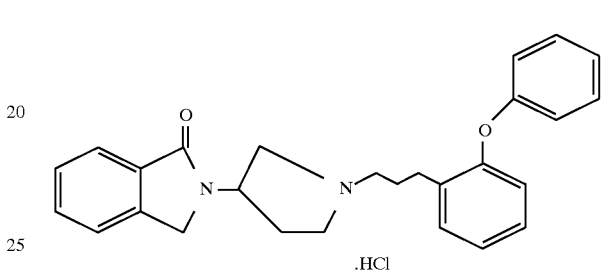
.HCl
EXAMPLE 15
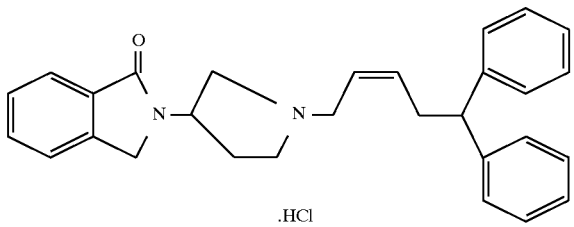
.HCl
EXAMPLE 16
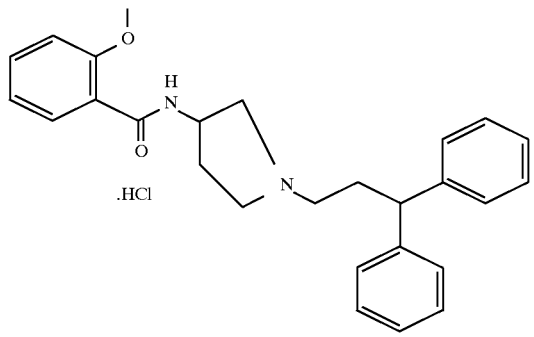
.HCl

EXAMPLE 17
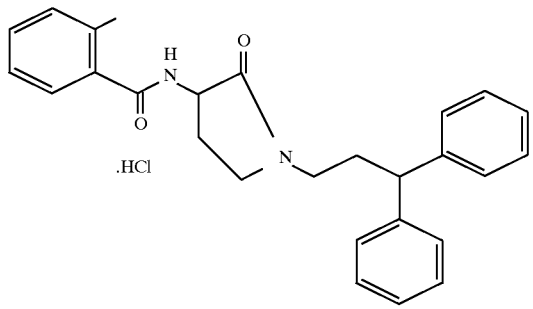
EXAMPLE 19
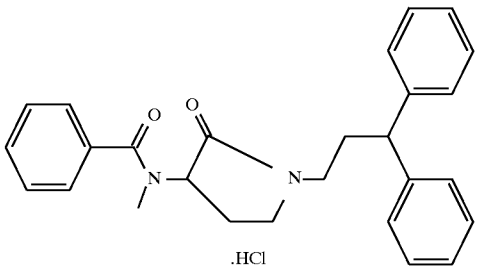
EXAMPLE 18
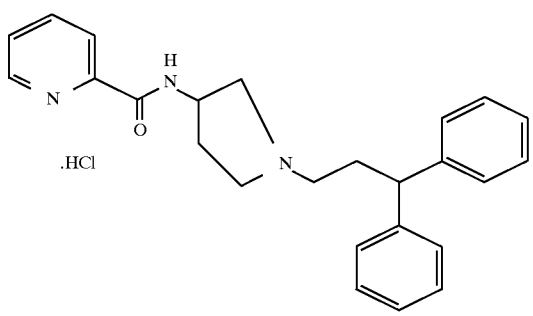
EXAMPLES 20 TO 202
TABLE A
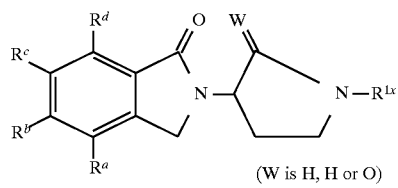
(W is H, H or O)
wherw $R^{1x}$ is
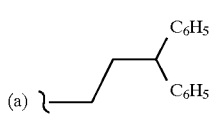 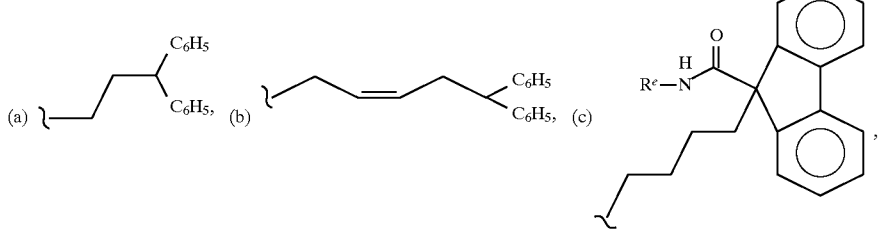
($R^e$ = $C_3H_7$ or $CF_3CH_2$)
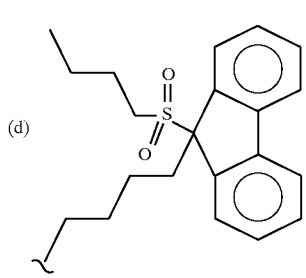 or 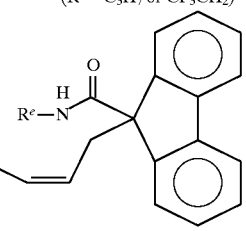

| $R^a$ | $R^b$ | $R^c$ | $R^d$ |
|---|---|---|---|
| H | H | H | F |
| H | H | H | 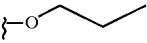 |
| H | H | F | Cl |
| H | H | CF$_3$ | H |
| H | OCH$_3$ | H | H |
| H | H | H | 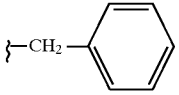 |
| 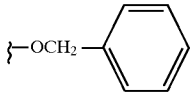 | H | H | H |
| H | H | 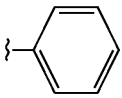 | H |
| F | Cl | H | H |
| H | H | H | 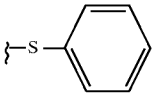 |
| H | H | H | 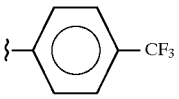 |
|  | H | H | H |
| H | H | Cl | H |
| H | H | H | 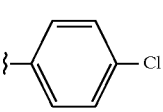 |
| H | H | H | H |
| H | H | H | Cl |
| H | H | CH$_3$ | H |
| H | CH3 | H |  |
| SCH$_3$ | H | H | H |
| H | H | OCH$_3$ | H |
| H | H | H | SCH$_3$ |
| H | H | H | H |
| H | H | H | 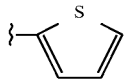 |
| H | 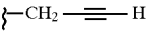 | H | H |
| H | H | H |  |

EXAMPLE 203
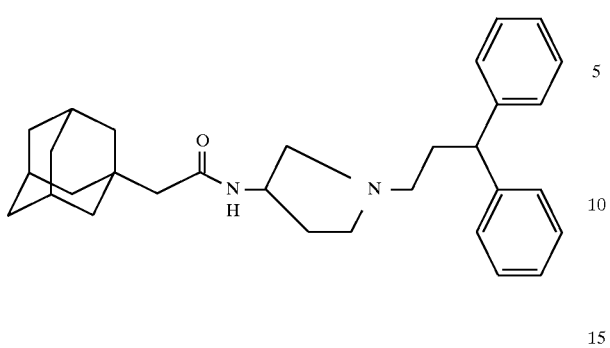
EXAMPLE 204
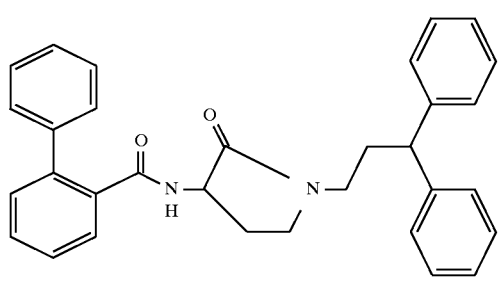
EXAMPLE 205
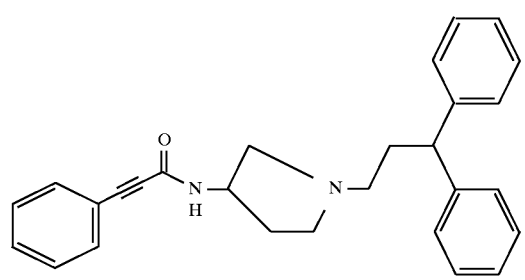
EXAMPLE 206
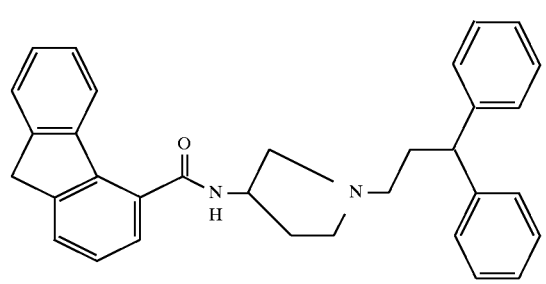
EXAMPLE 207
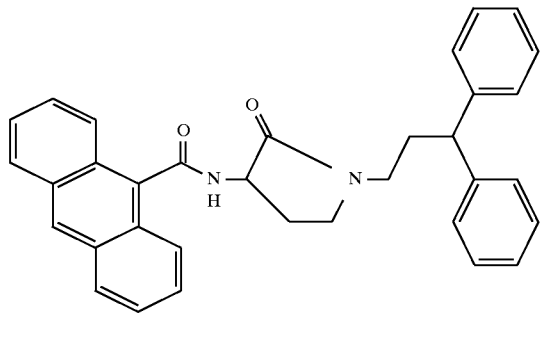
EXAMPLE 208
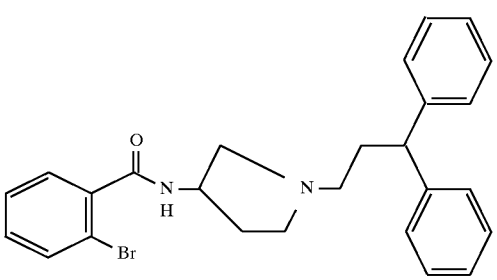
EXAMPLE 209
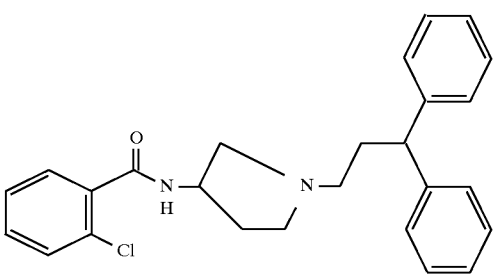
EXAMPLE 210
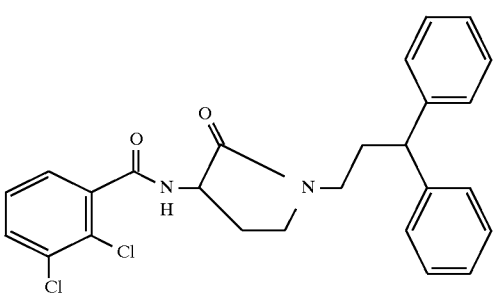

EXAMPLE 211
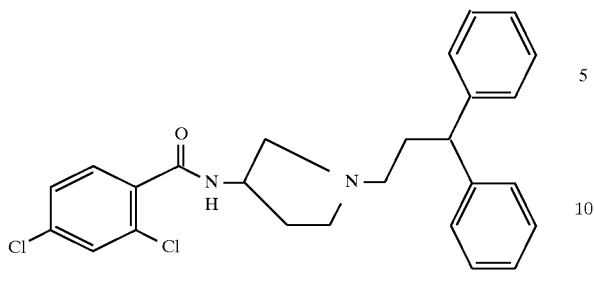
EXAMPLE 212
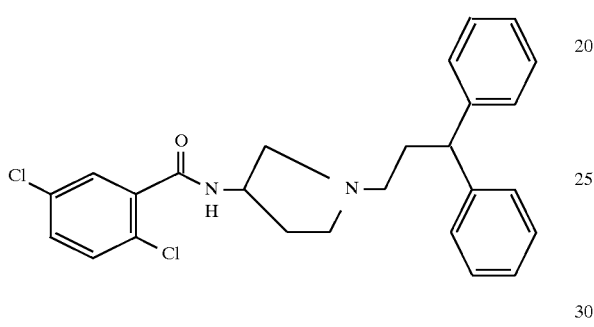
EXAMPLE 213
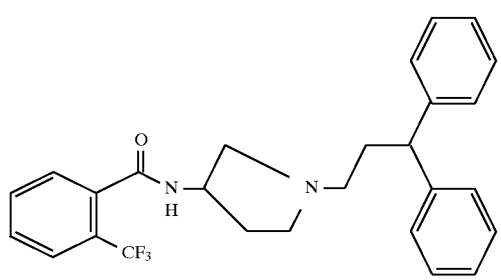
EXAMPLE 214
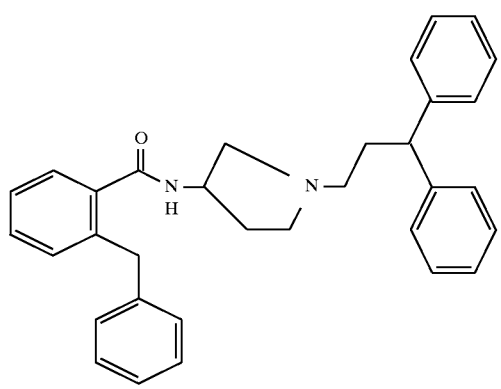
EXAMPLE 215
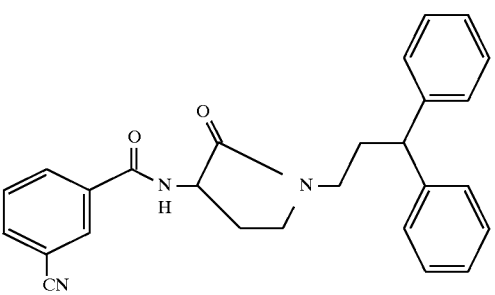
EXAMPLE 216
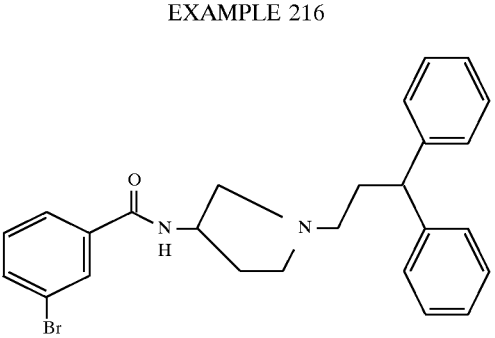
EXAMPLE 217
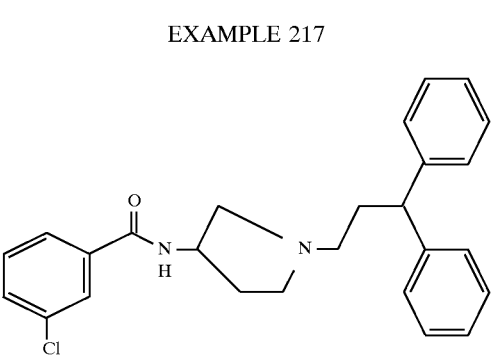
EXAMPLE 218
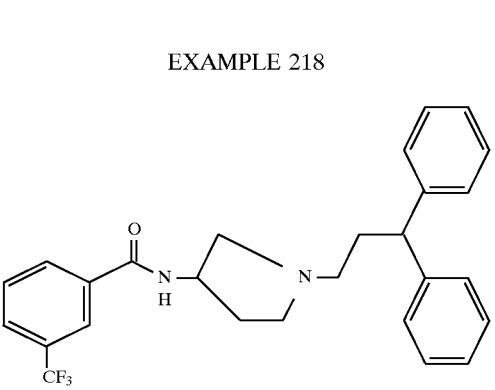

EXAMPLE 219
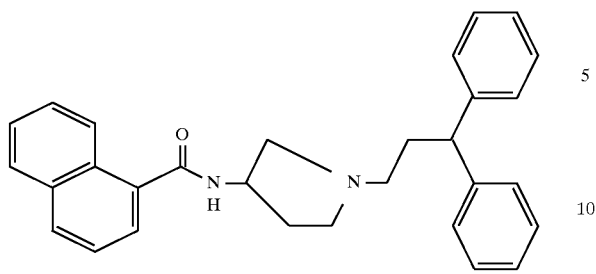
EXAMPLE 220
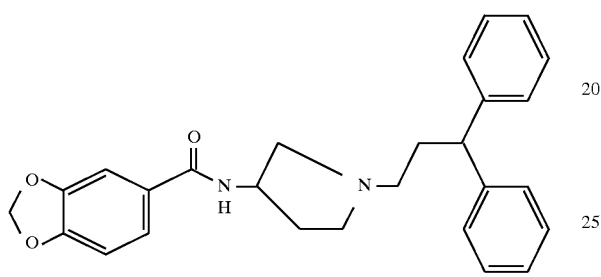
EXAMPLE 221
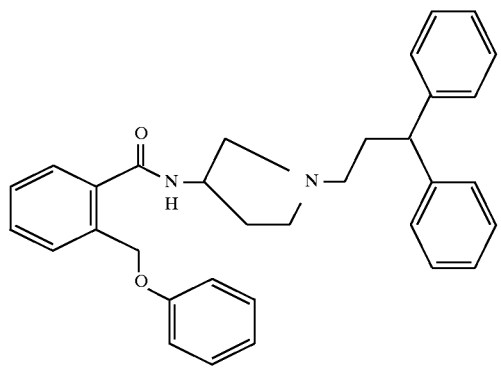
EXAMPLE 222
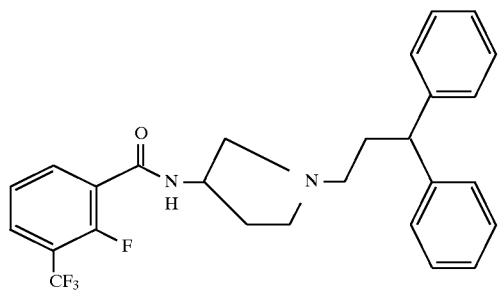
EXAMPLE 223
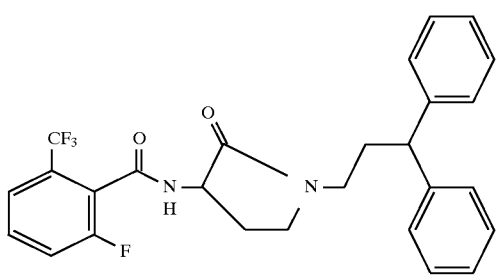
EXAMPLE 224
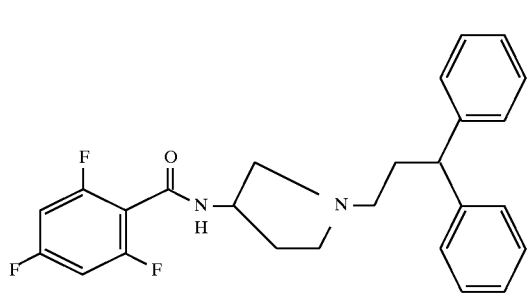
EXAMPLE 225
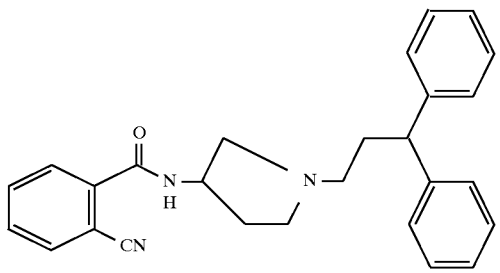
EXAMPLE 226
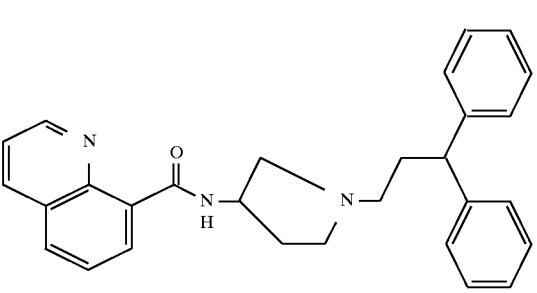

EXAMPLE 227
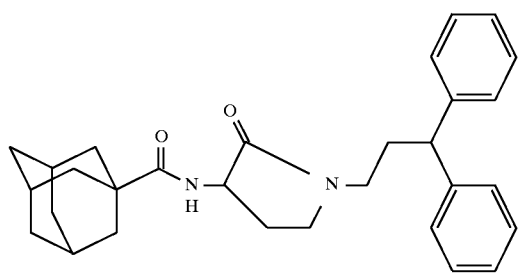
EXAMPLE 228
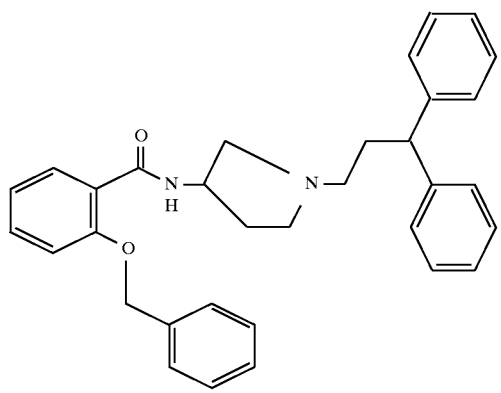
EXAMPLE 229
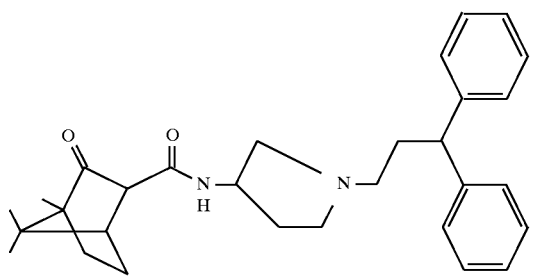
EXAMPLE 230
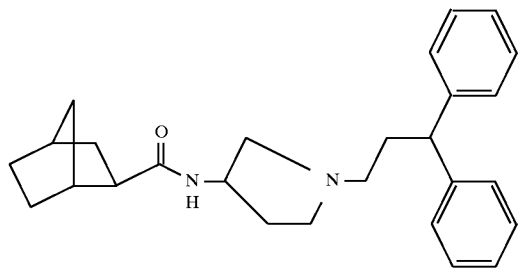
EXAMPLE 231
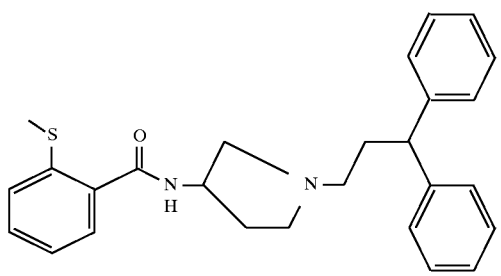
EXAMPLE 232
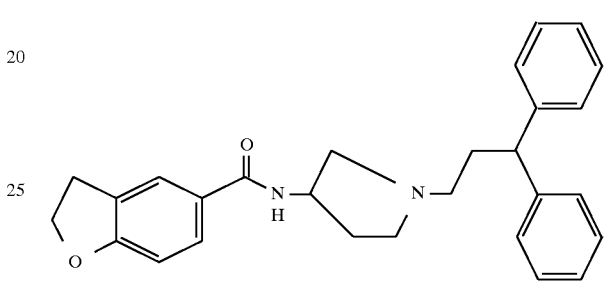
EXAMPLE 233
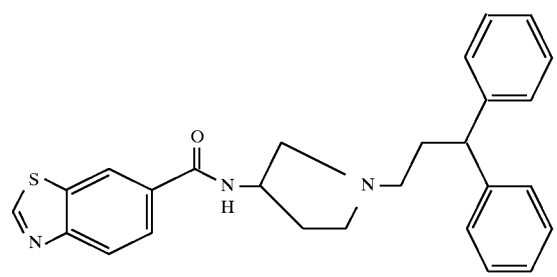
EXAMPLE 234
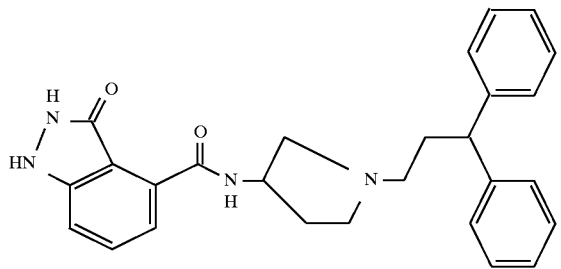

EXAMPLE 235
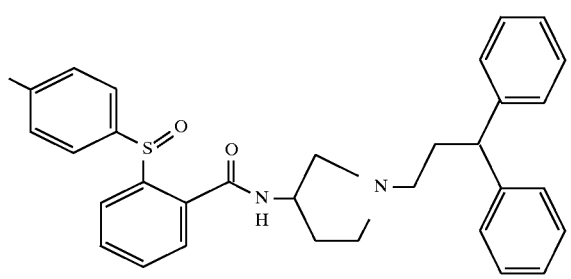
EXAMPLE 239
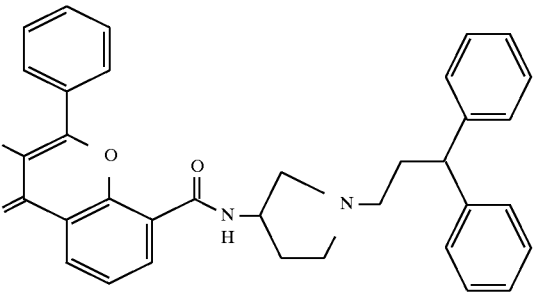
EXAMPLE 236
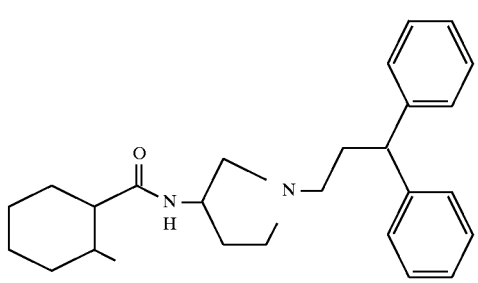
EXAMPLE 240
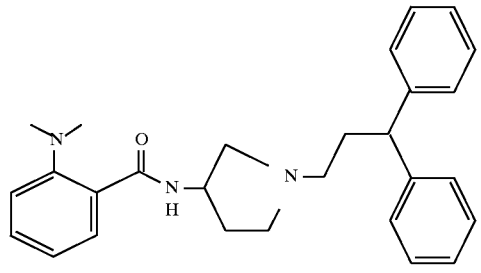
EXAMPLE 237
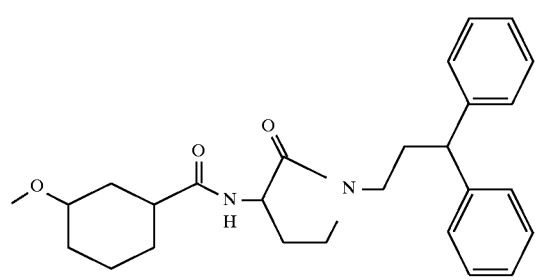
EXAMPLE 241
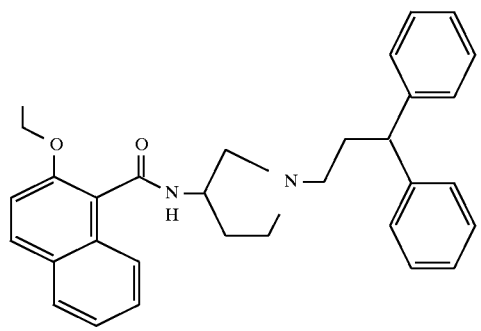
EXAMPLE 238
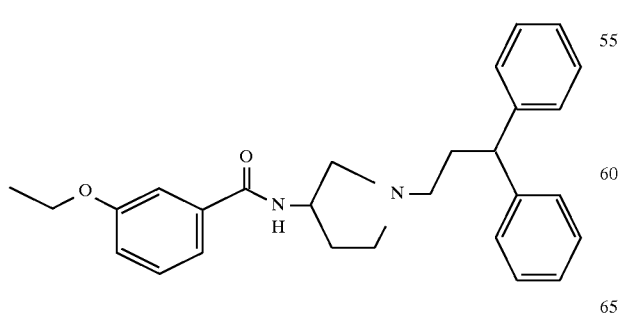
EXAMPLE 242
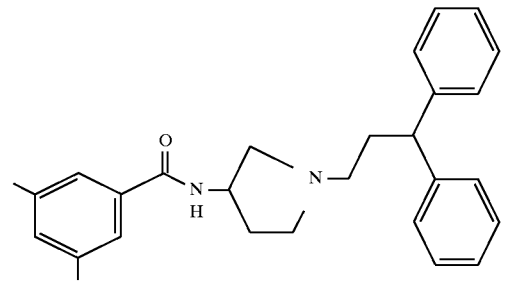

EXAMPLE 243
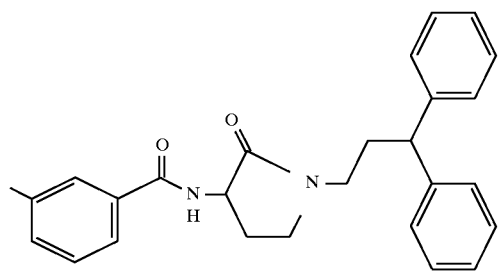
EXAMPLE 244
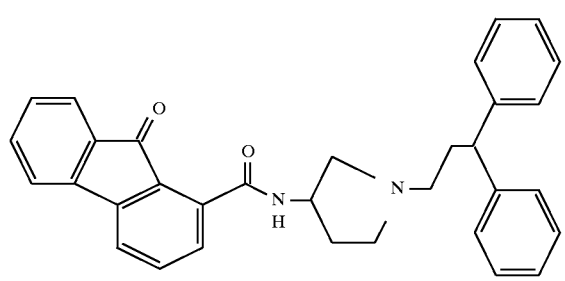
EXAMPLE 245
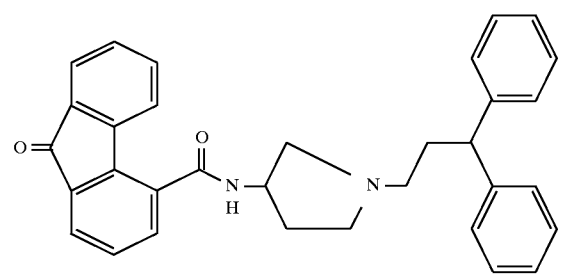
EXAMPLE 246
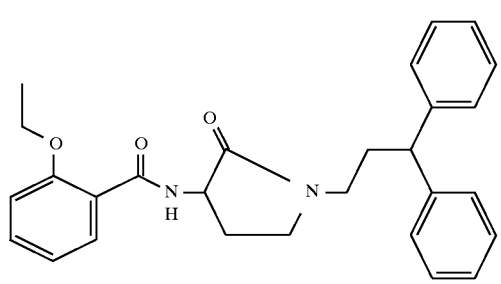
EXAMPLE 247
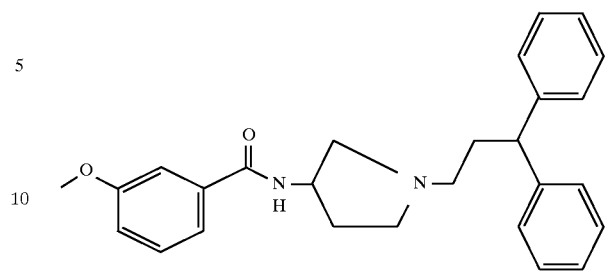
EXAMPLE 248
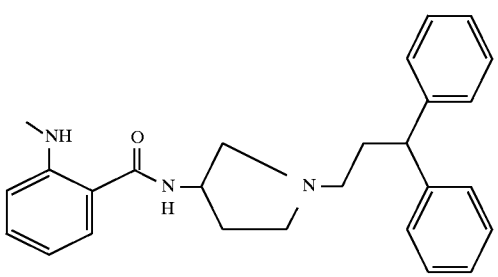
EXAMPLE 249
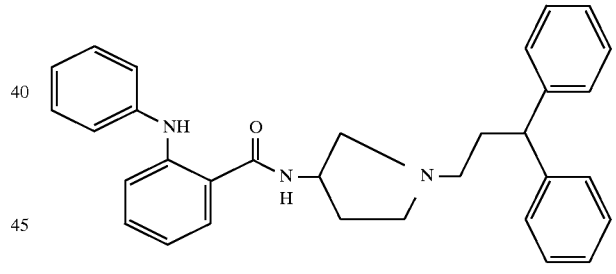
EXAMPLE 250
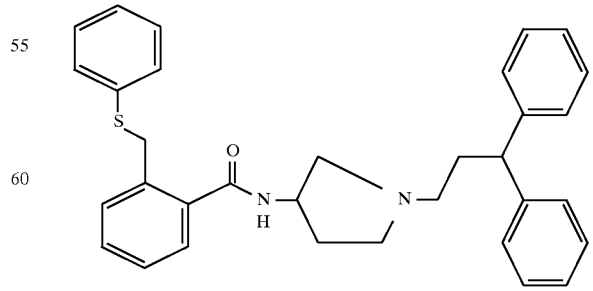

EXAMPLE 251
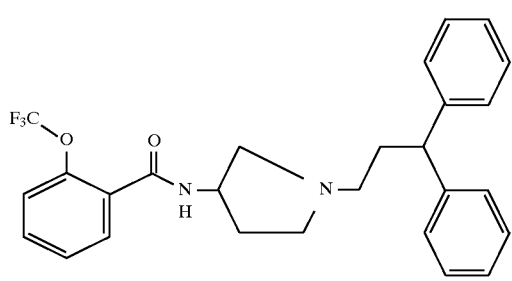
EXAMPLE 252
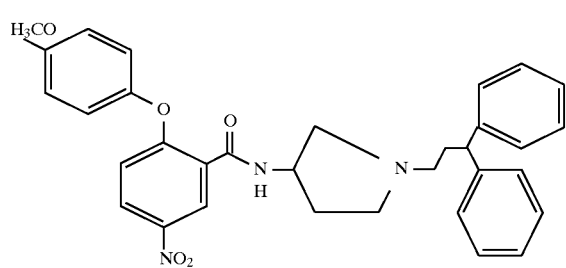
EXAMPLE 253
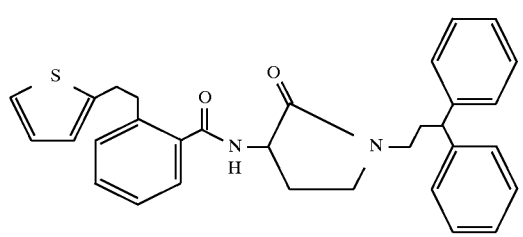
EXAMPLE 254
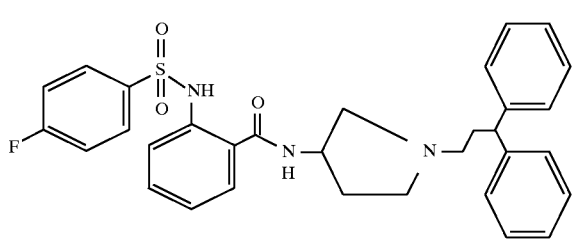
EXAMPLE 255
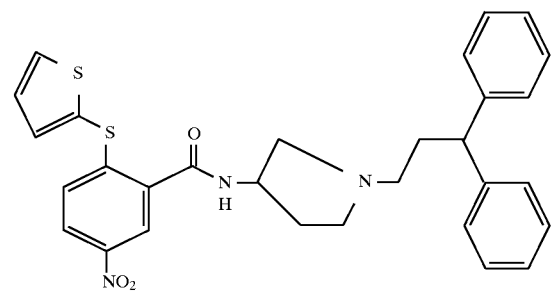
EXAMPLE 256
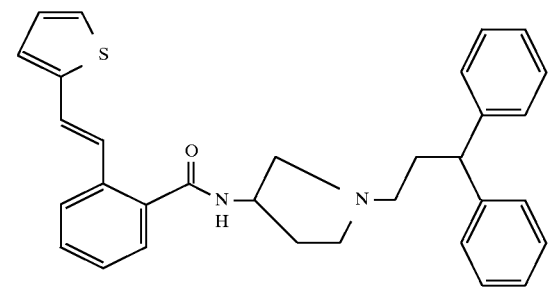
EXAMPLE 257
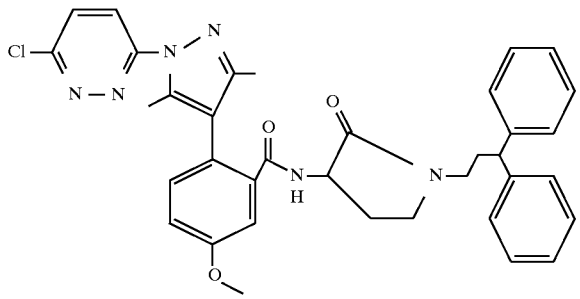
EXAMPLE 258
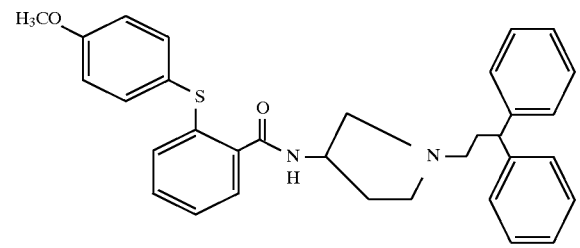

EXAMPLE 259
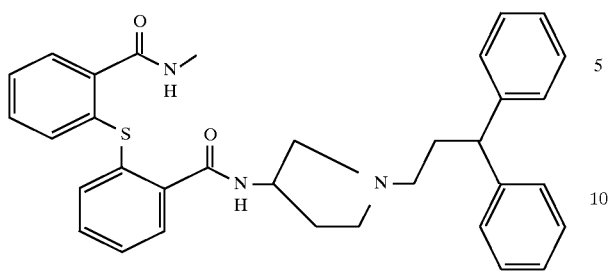
EXAMPLE 263
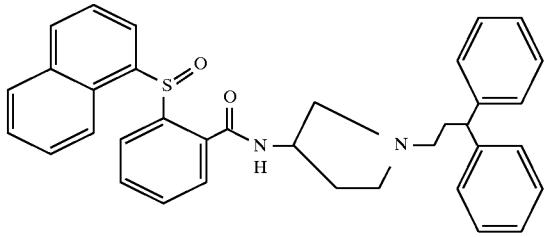
EXAMPLE 264
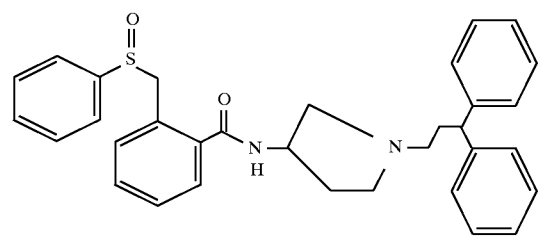
EXAMPLE 260
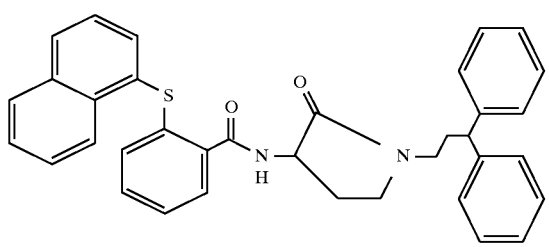
EXAMPLE 265
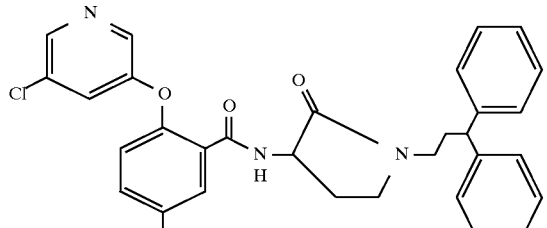
EXAMPLE 261
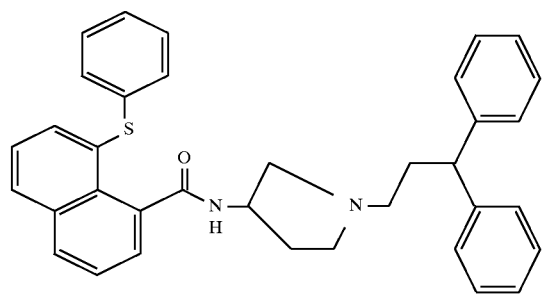
EXAMPLE 266
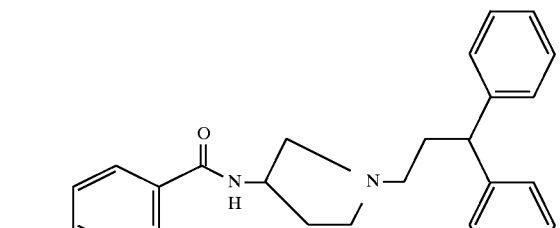
EXAMPLE 262
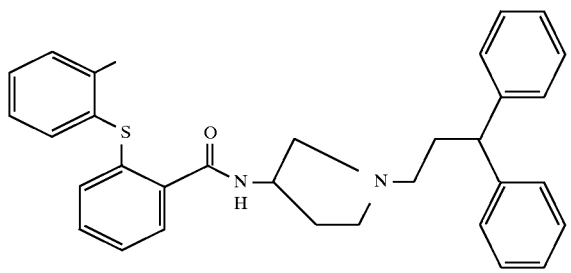

EXAMPLE 267
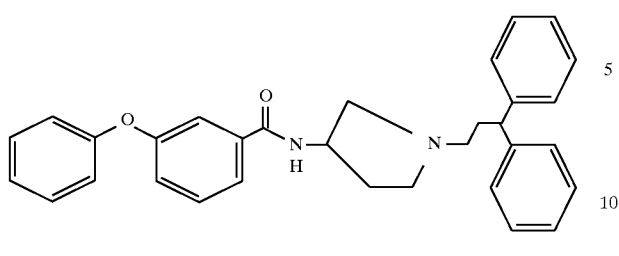
EXAMPLE 268
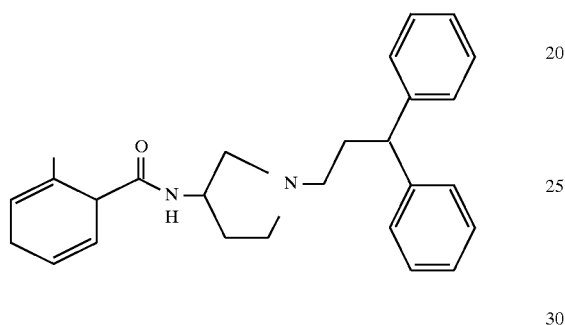
EXAMPLE 269
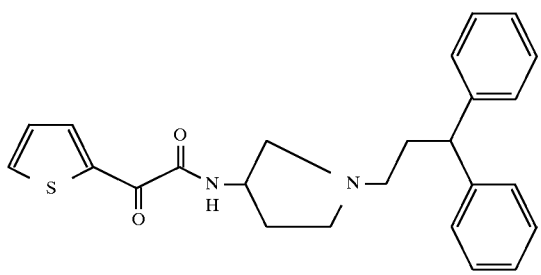
EXAMPLE 270
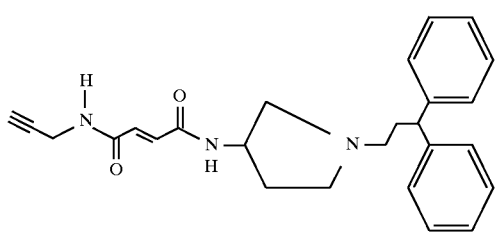
EXAMPLE 271
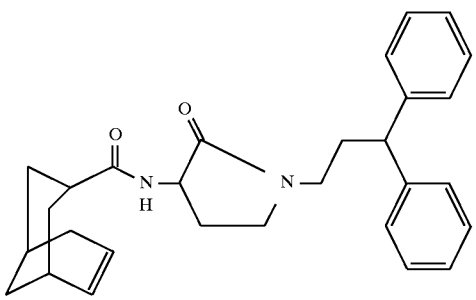
EXAMPLE 272
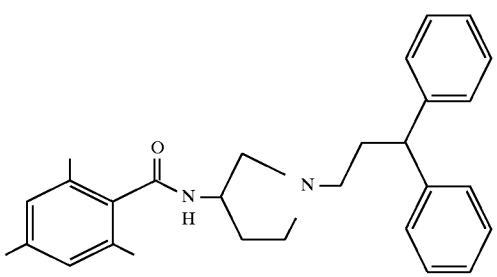
EXAMPLE 273
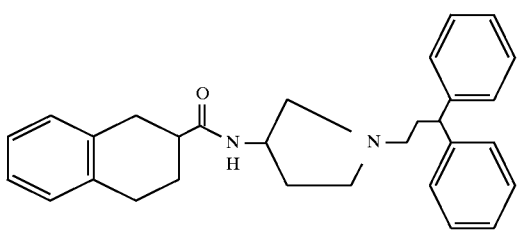
EXAMPLE 274
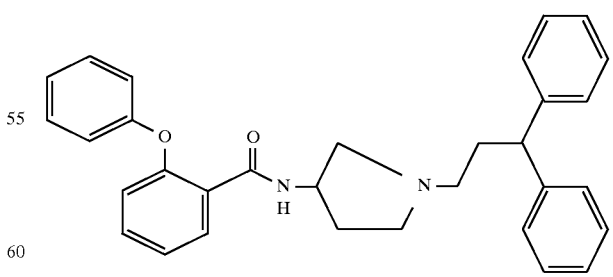

EXAMPLE 275
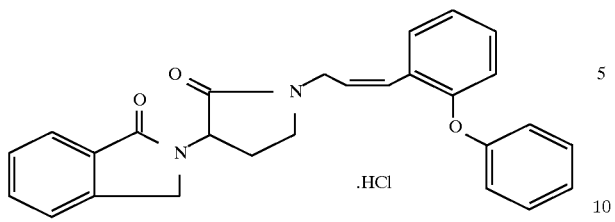
.HCl
EXAMPLE 276
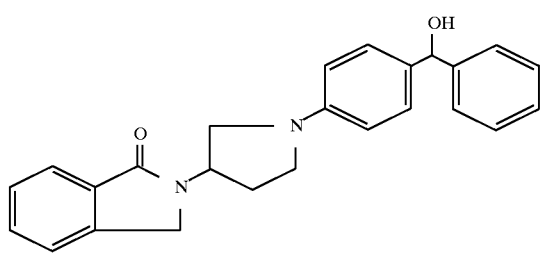
EXAMPLE 277
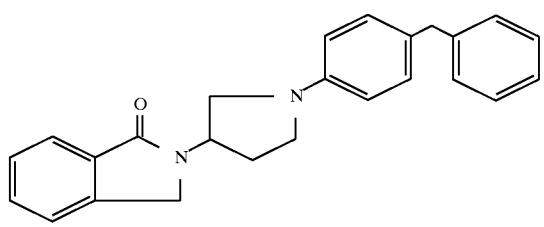
EXAMPLE 278
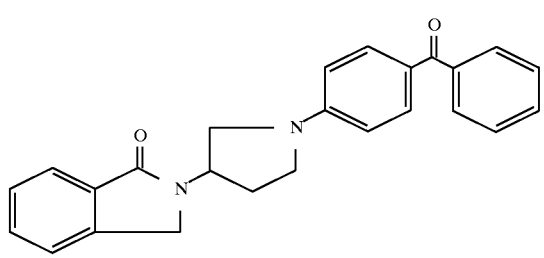
EXAMPLE 279
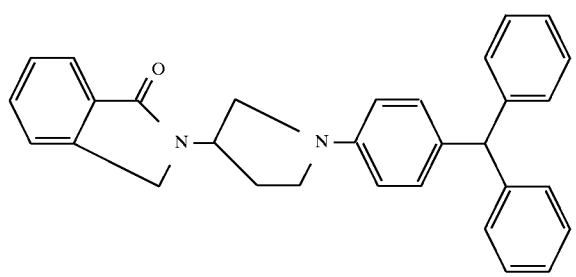
EXAMPLE 280
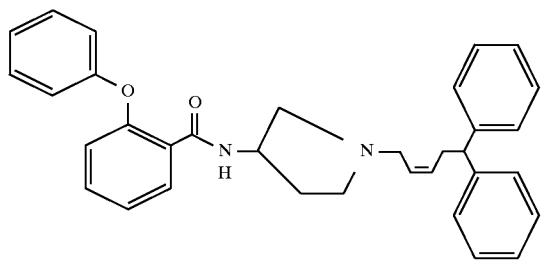
EXAMPLE 281
(Z)-N-[1-(5,5-Diphenyl-2-pentenyl)-3-pyrrolidinyl]-
2-phenoxybenzamide
EXAMPLE 282
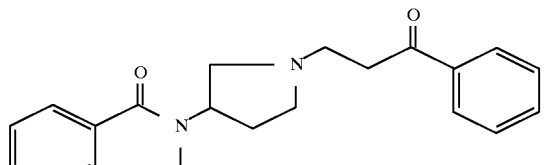
EXAMPLE 283
2,3-Dihydro-2-[1-[3-phenyl-3-(4-propylphenyl)
propyl]-3-pyrrolidinyl]-1H-isoindol-1-one,
monohydrochloride
EXAMPLE 284
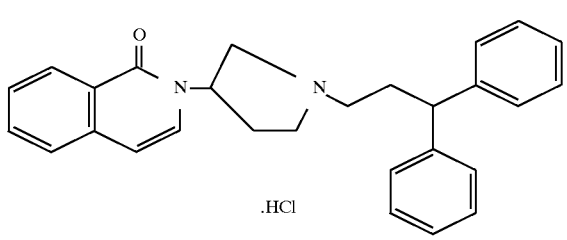
.HCl
EXAMPLE 285
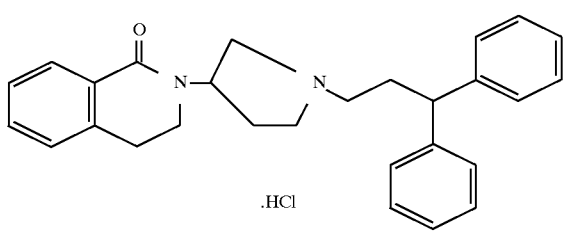
.HCl EXAMPLE 286
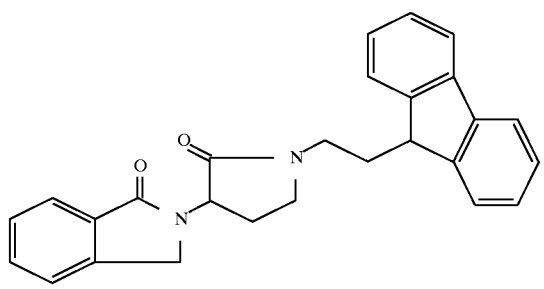
EXAMPLE 290
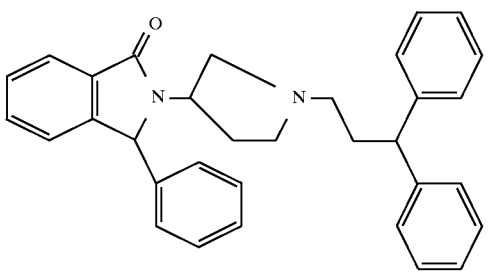
EXAMPLE 287
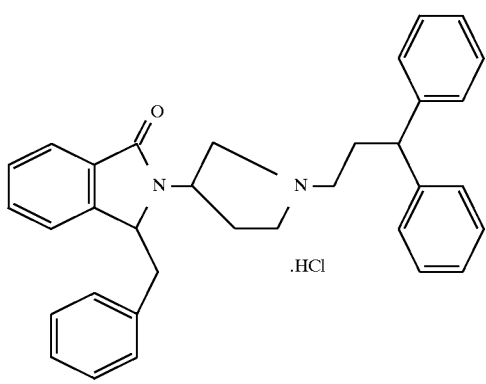
EXAMPLE 291
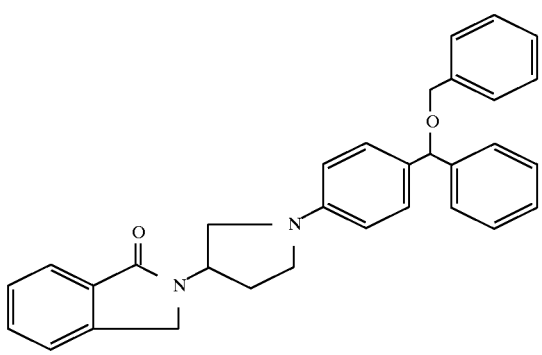
EXAMPLE 288
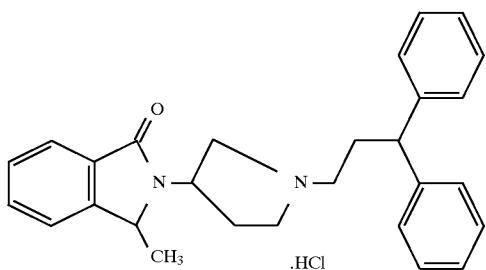
EXAMPLE 292
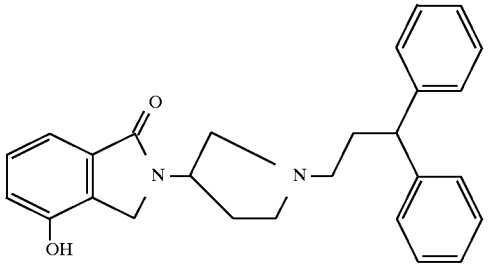
EXAMPLE 289
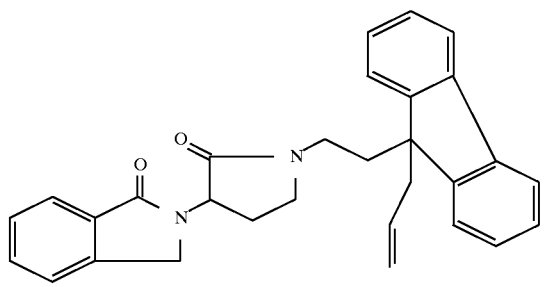
EXAMPLE 293
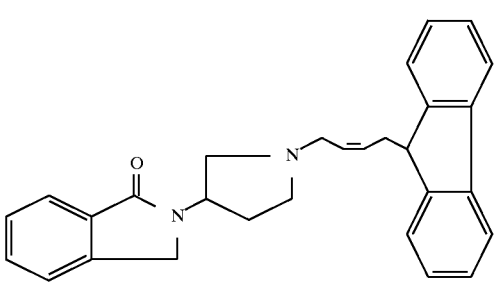

EXAMPLE 294
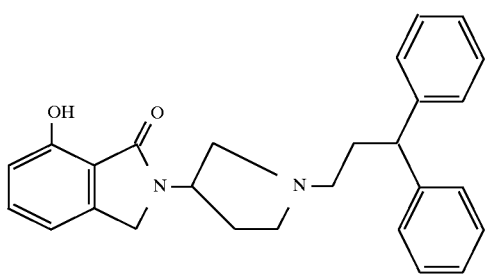
EXAMPLE 295
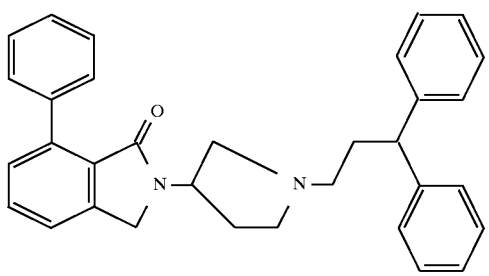
EXAMPLE 296
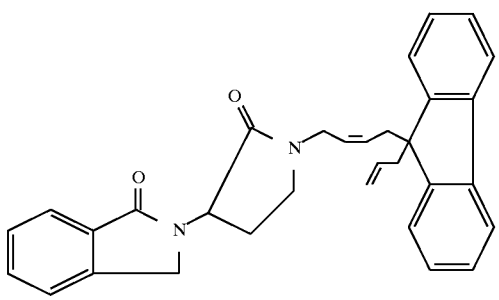
EXAMPLE 297
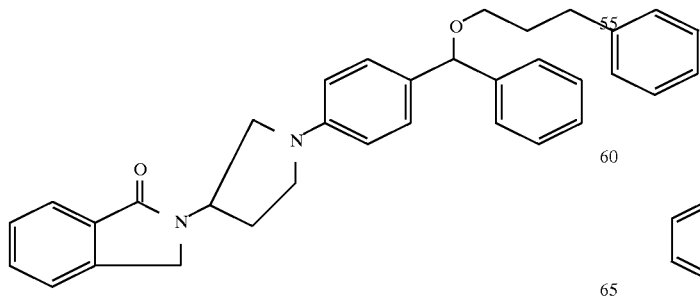
EXAMPLE 298
$CHR^8$,  $-\underset{\underset{O}{\|}}{C}-$,  $-\underset{\underset{R^9}{|}}{CH}-\underset{\underset{R^{10}}{|}}{CH}-$  or  $-\underset{\underset{R^9}{|}}{C}=\underset{\underset{R^{10}}{|}}{C}-$;
EXAMPLE 299
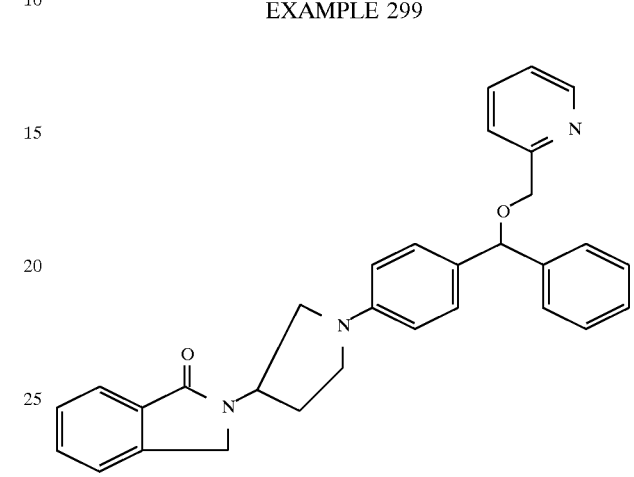
EXAMPLE 300
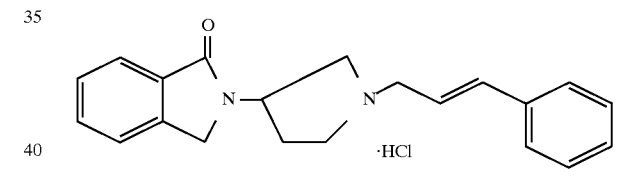
EXAMPLE 301
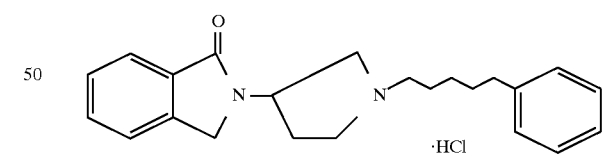
EXAMPLE 302
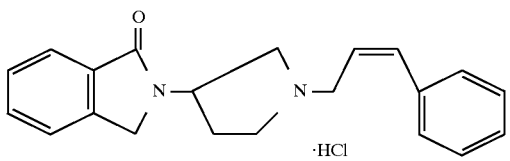

EXAMPLE 303
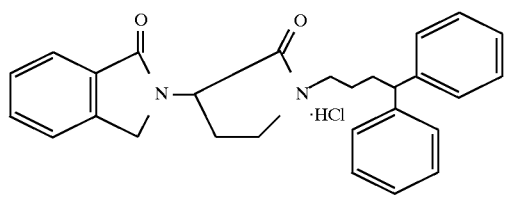
EXAMPLE 307
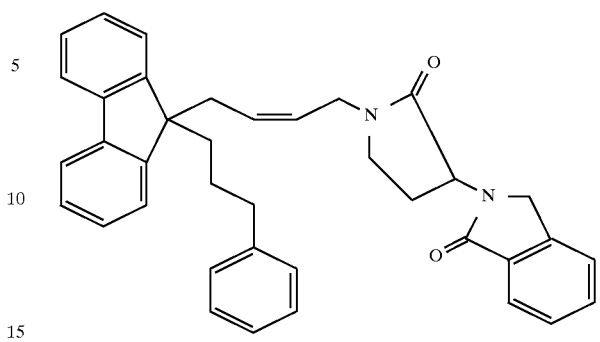
EXAMPLE 304
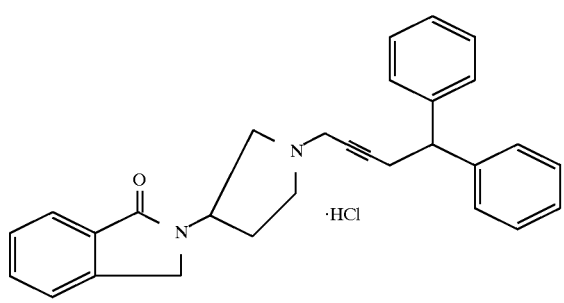
EXAMPLE 308
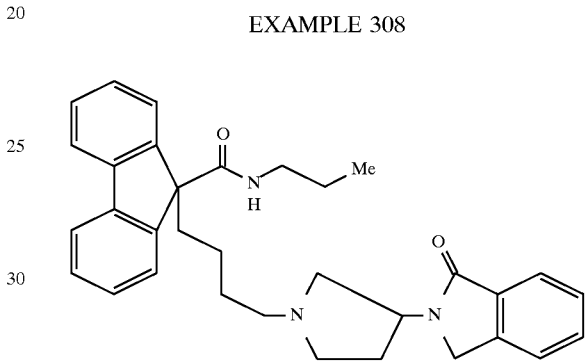
EXAMPLE 305
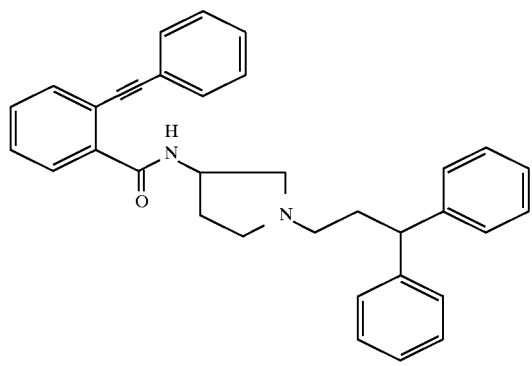
EXAMPLE 309
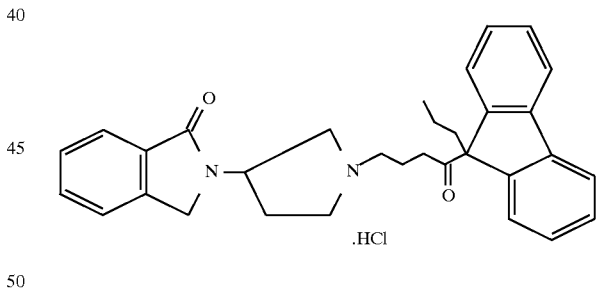
EXAMPLE 306
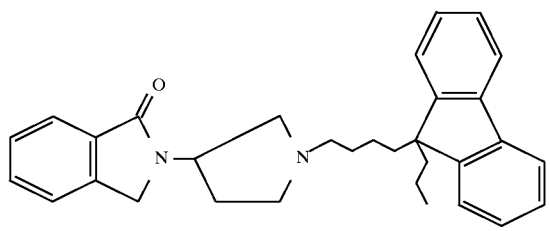
EXAMPLE 310
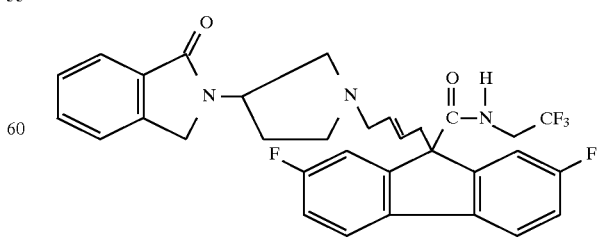

EXAMPLE 311
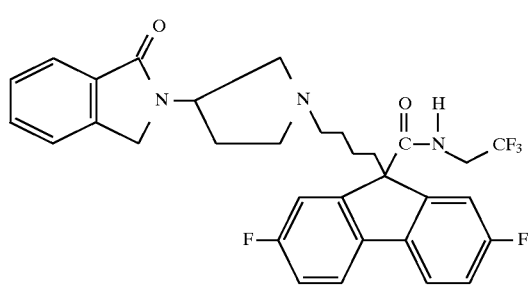
EXAMPLE 312
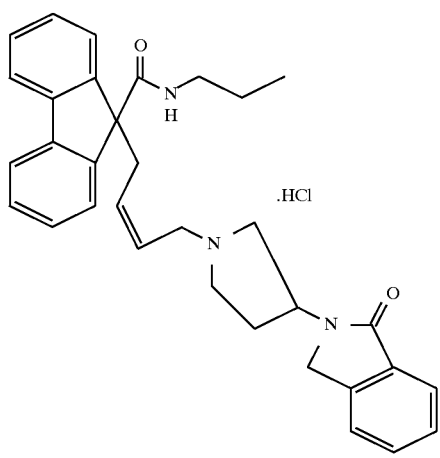
EXAMPLE 313
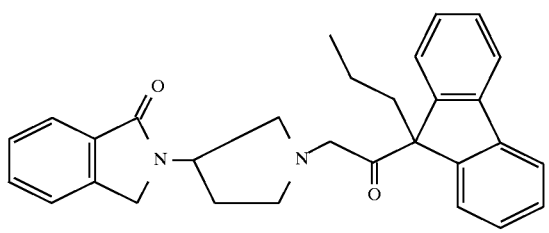
EXAMPLE 314
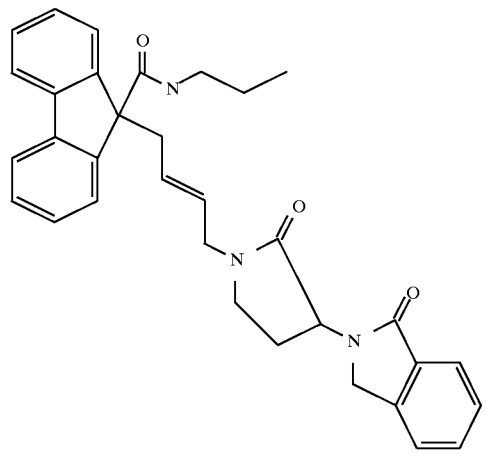
EXAMPLE 315
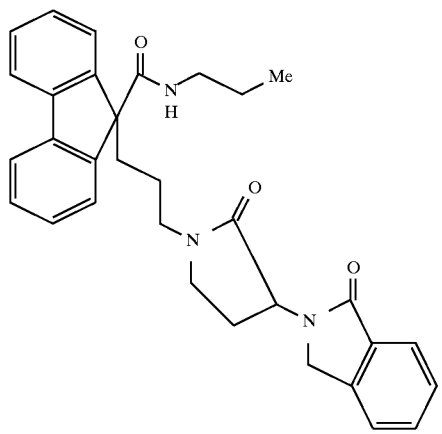
EXAMPLE 316
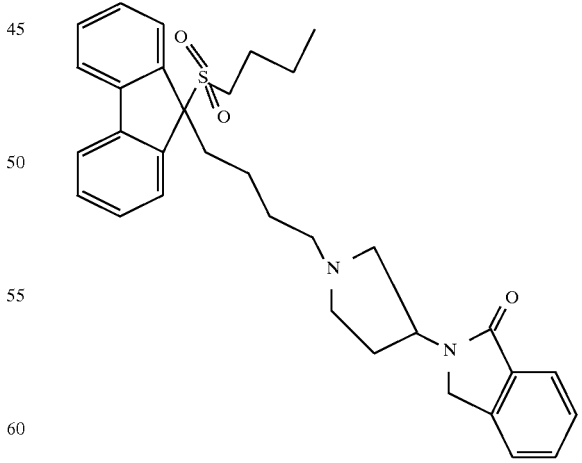

107
EXAMPLE 317
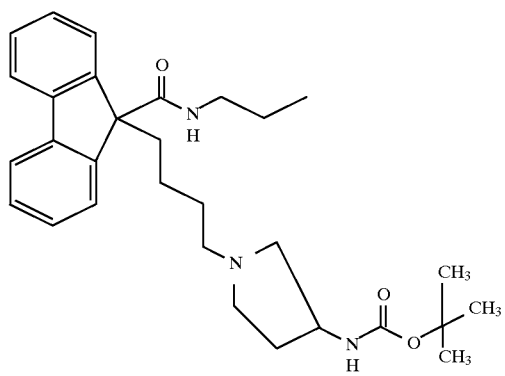
EXAMPLE 318
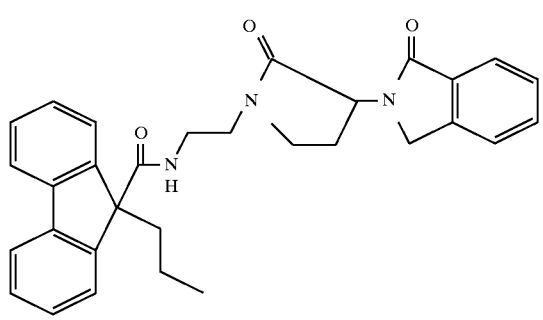
EXAMPLE 319
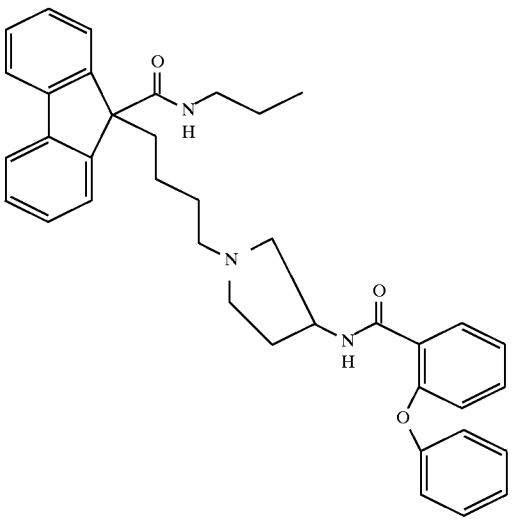
108
EXAMPLE 320
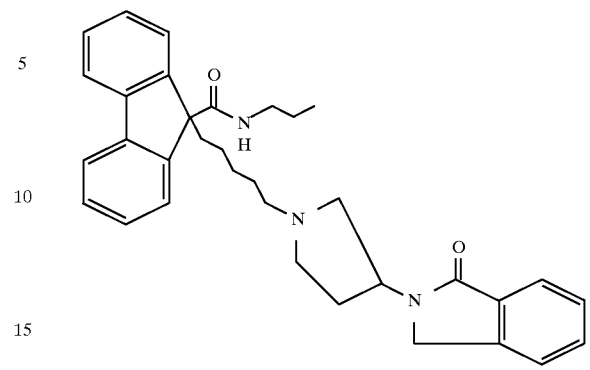
EXAMPLE 321
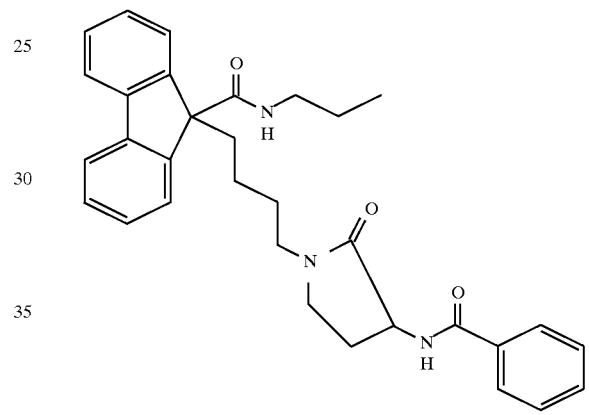
EXAMPLE 322
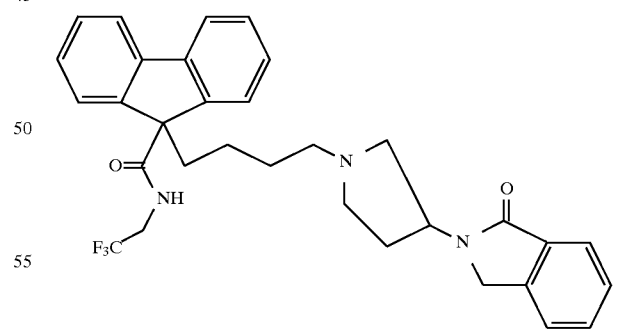

EXAMPLE 323
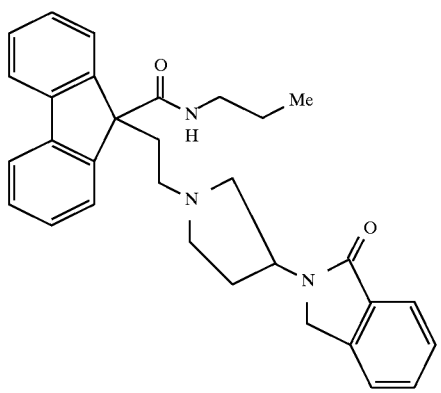
EXAMPLE 324
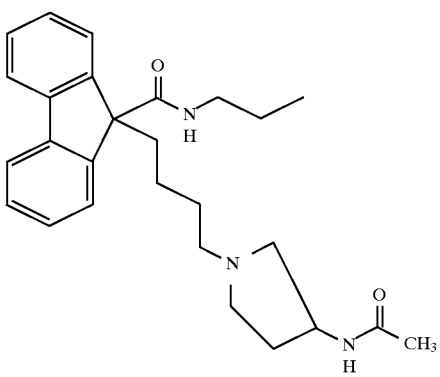
EXAMPLE 325
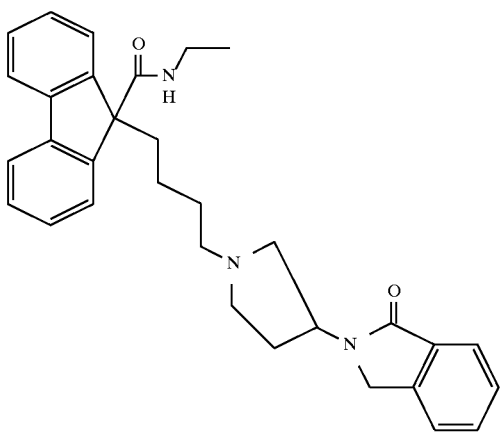
EXAMPLE 326
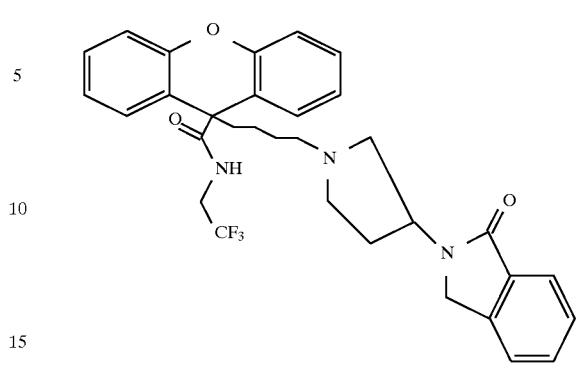
EXAMPLE 327
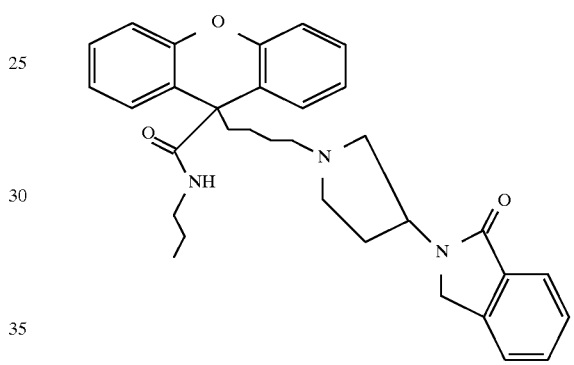
EXAMPLE 328
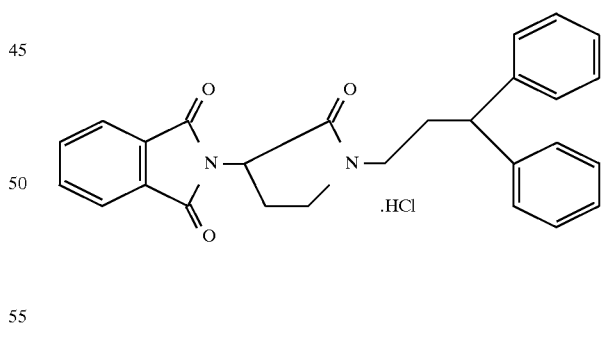

111
EXAMPLE 329
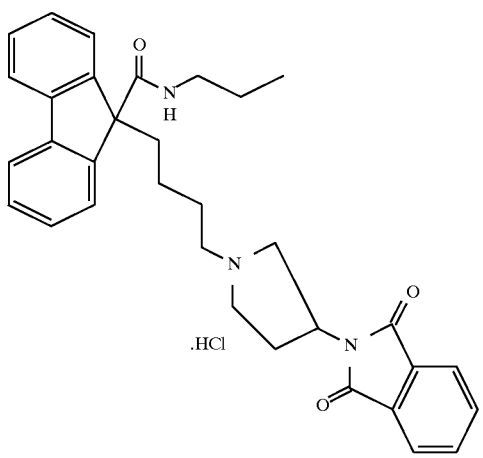
.HCl
EXAMPLE 330
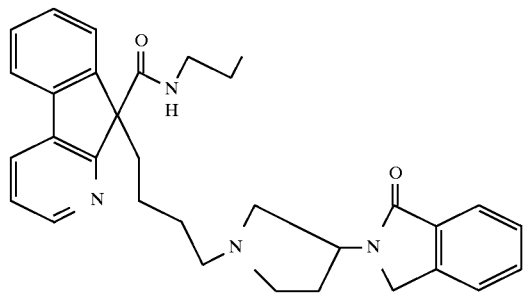
EXAMPLE 331
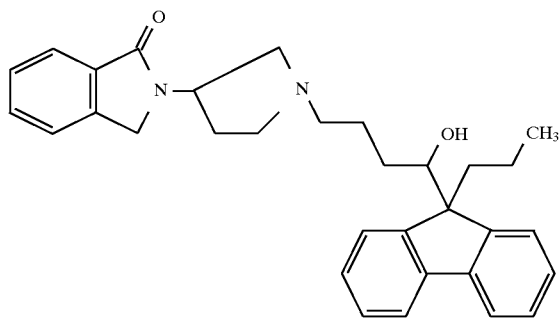
EXAMPLE 332
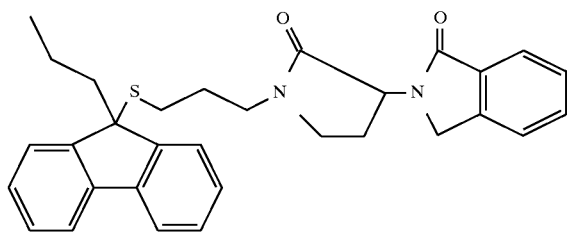
112
EXAMPLE 333
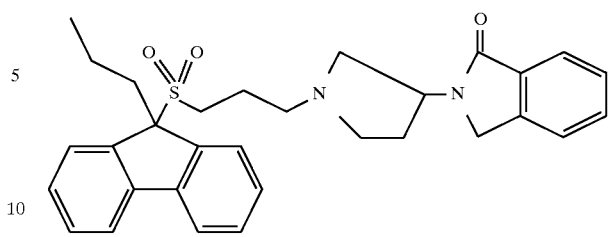
EXAMPLE 334
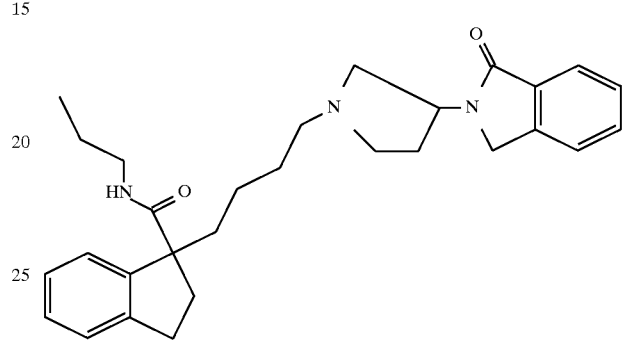
EXAMPLE 335
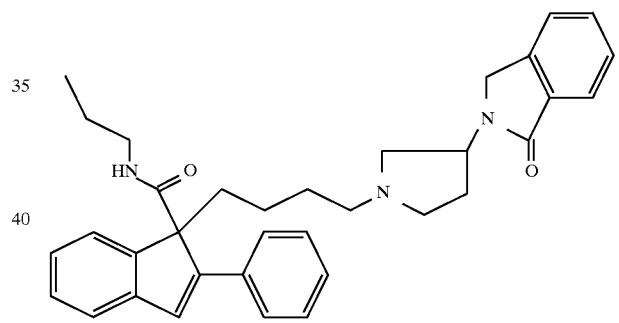
EXAMPLE 336
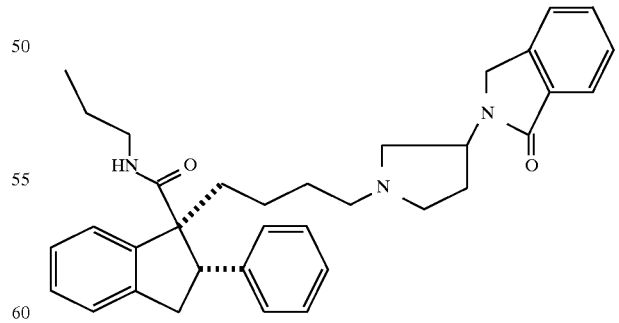
Additional compounds falling within the scope of the present invention are described by the following structures. Substituents for each example are identified in the table following each structure.

TABLE B
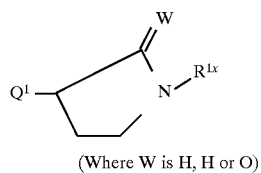
(Where W is H, H or O)
where $R^{1x}$ is (a), (b), (c), (d) or (e) as in Table A
Examples of $Q^1$
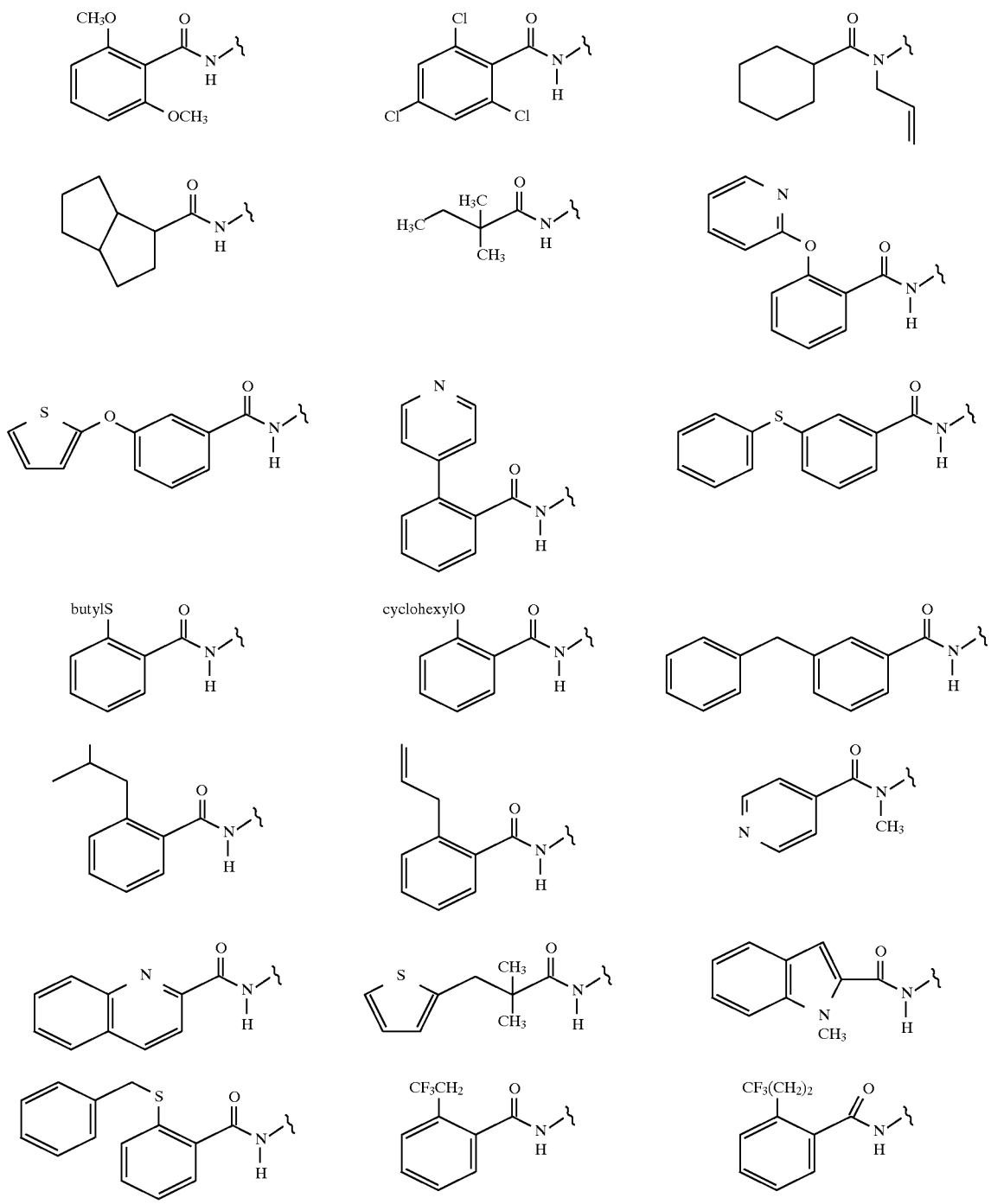

TABLE B-continued
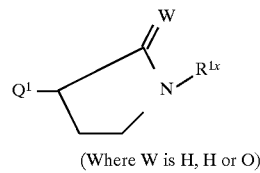
(Where W is H, H or O)
where $R^{1x}$ is (a), (b), (c), (d) or (e) as in Table A
Examples of $Q^1$
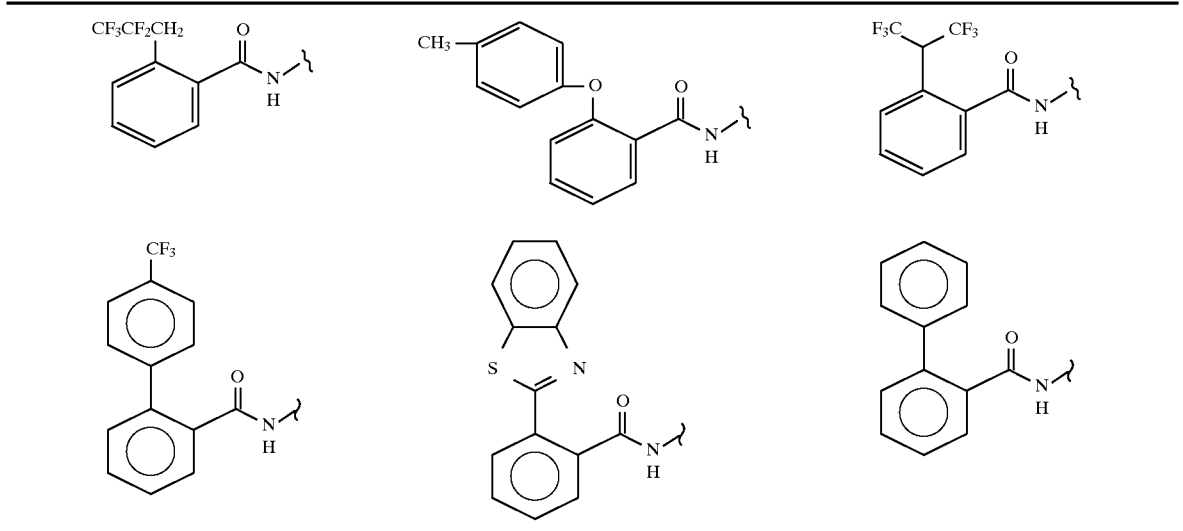
TABLE C
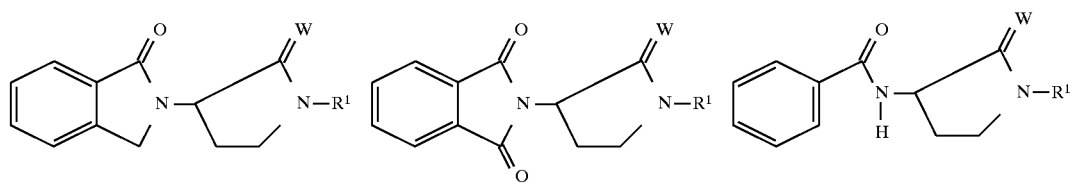
(Where W is H, H or O)
Examples of $R^1$
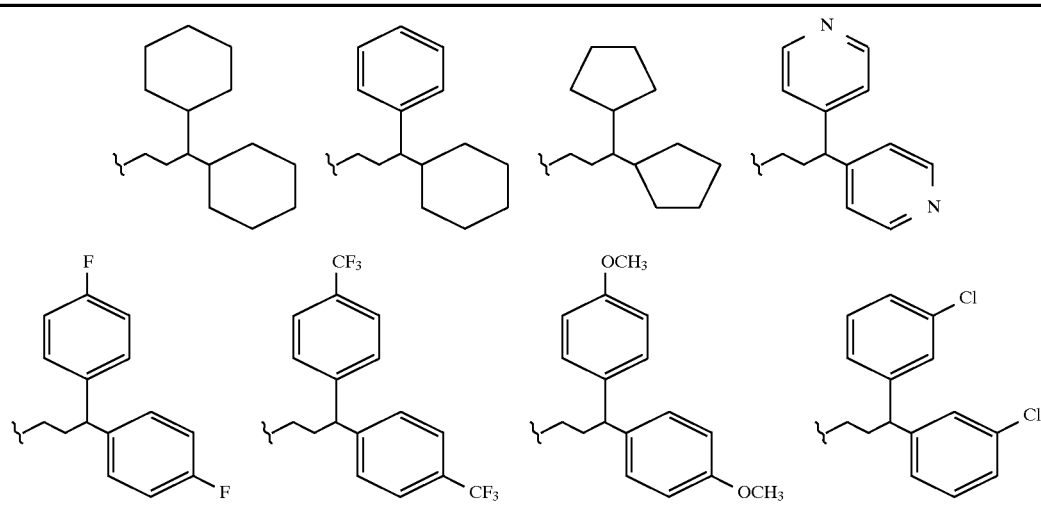

TABLE C-continued
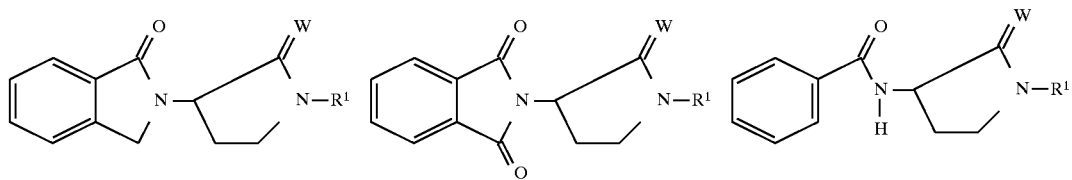
(Where W is H, H or O)
Examples of R[1]
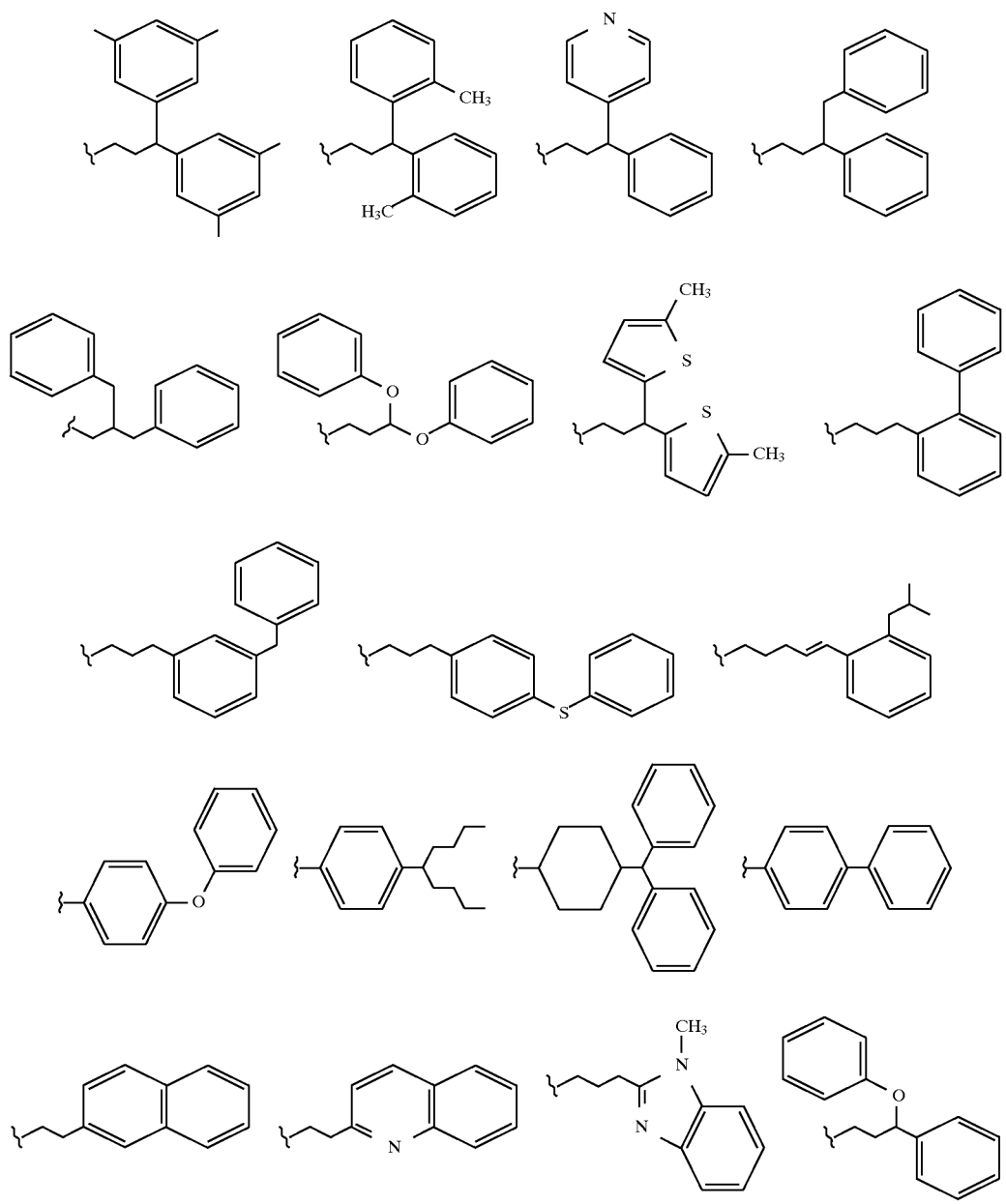

TABLE C-continued
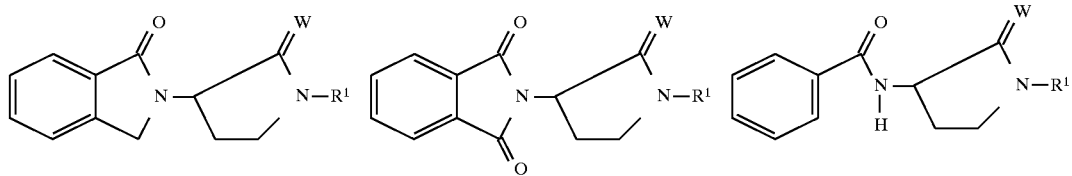
(Where W is H, H or O)
Examples of R¹
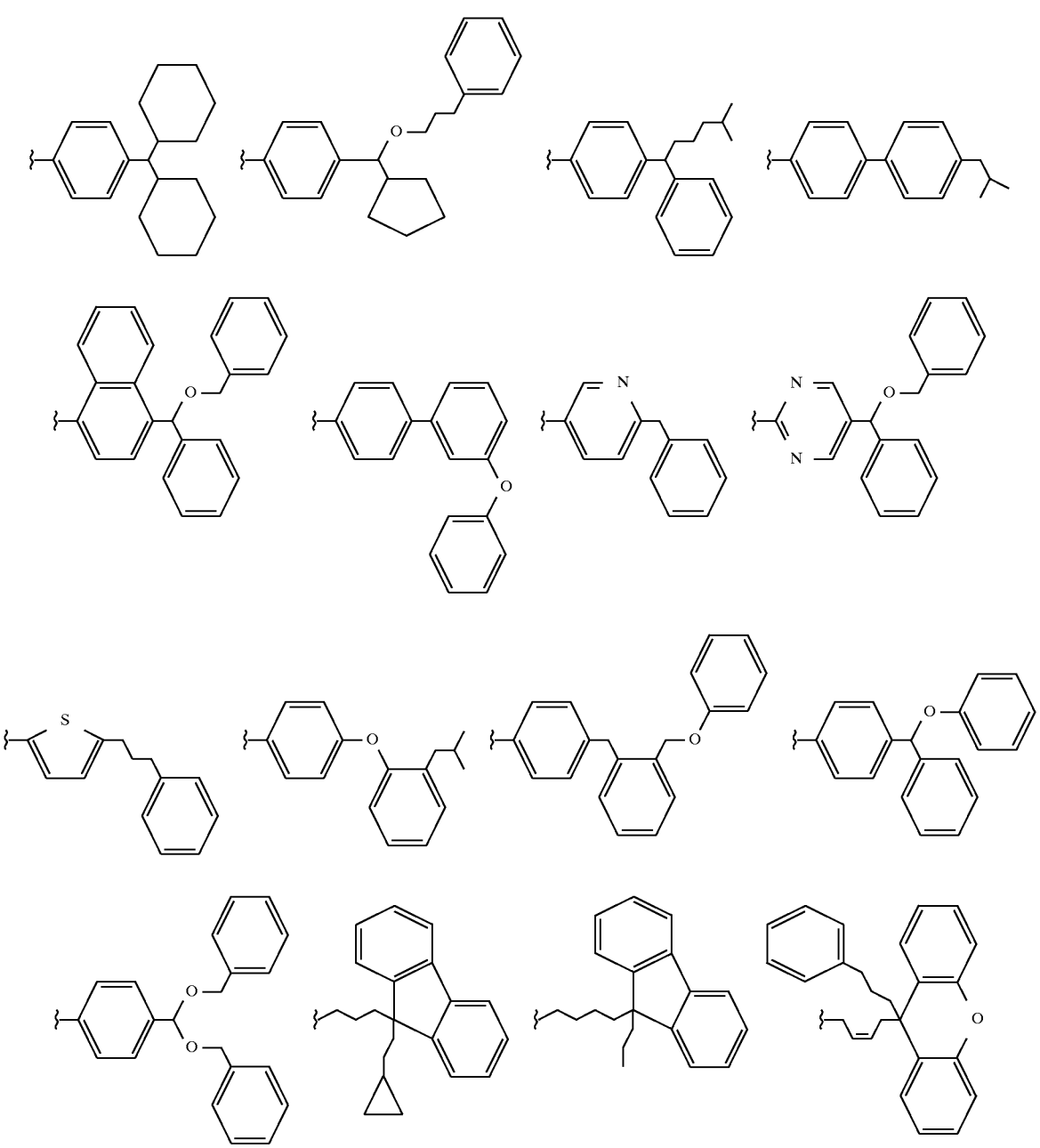

TABLE C-continued
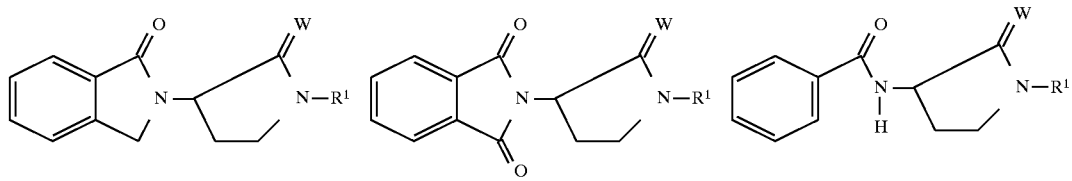
(Where W is H, H or O)
Examples of $R^1$
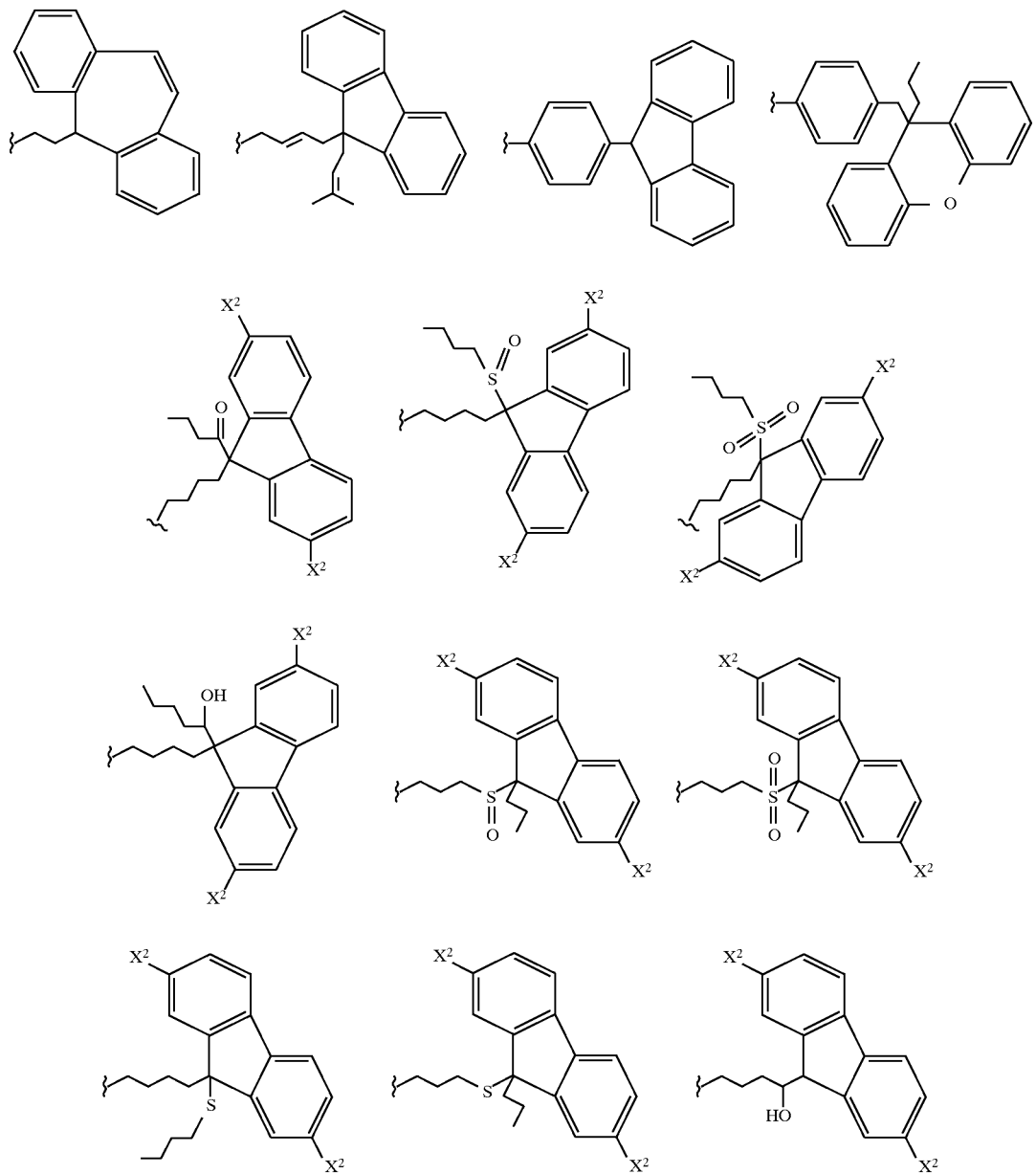

TABLE C-continued
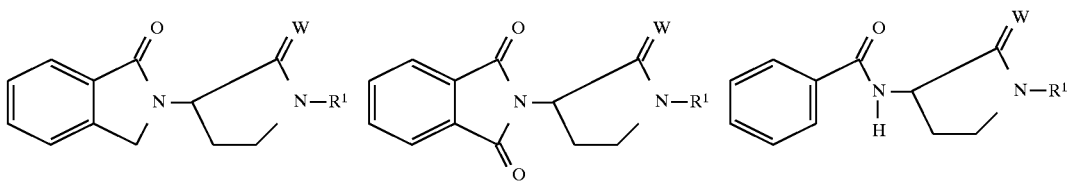
(Where W is H, H or O)
Examples of $R^1$
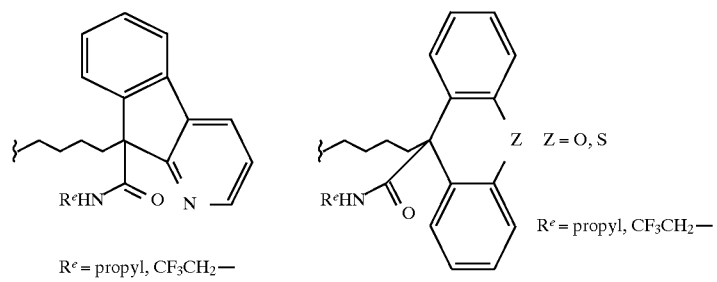
$X^2$ for Table C = H or F
TABLE D
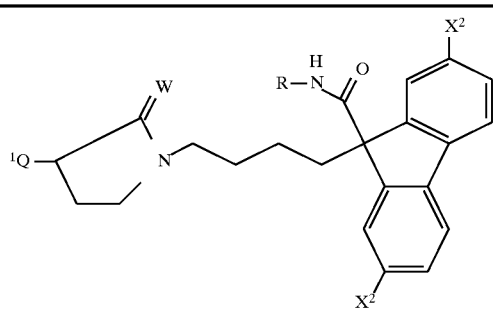
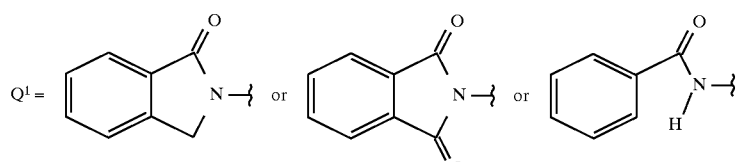
$X^2$ = H or F, W = H, H or O
Example of R
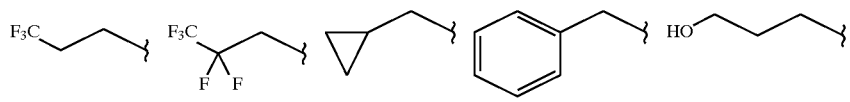
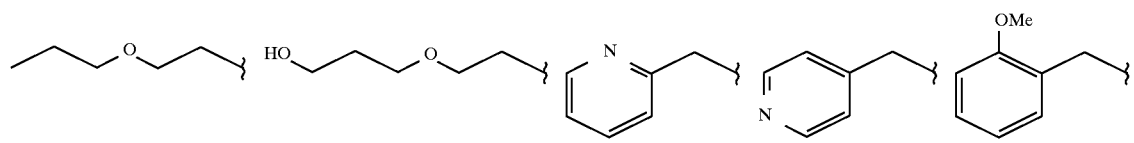
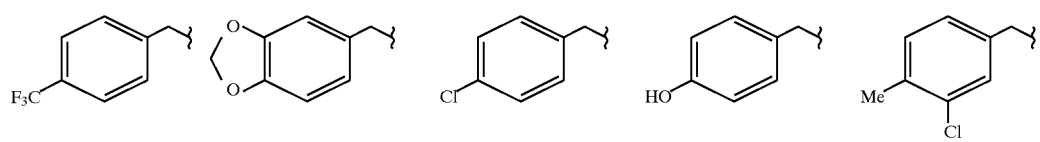

TABLE D-continued
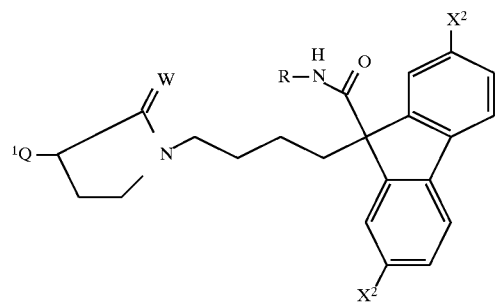
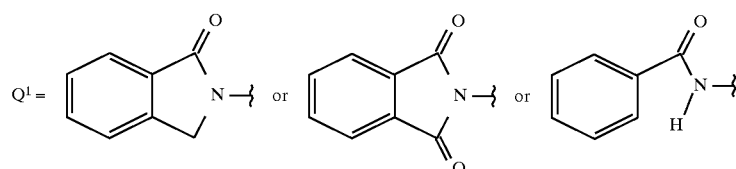
$X^2 = H$ or $F$, $W = H$, $H$ or $O$
Example of R
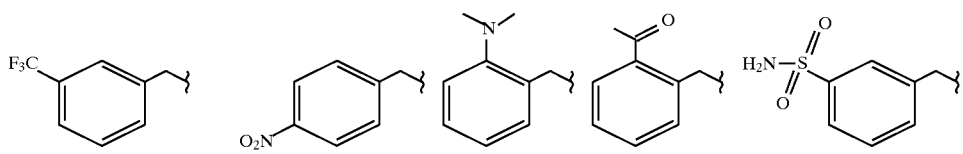
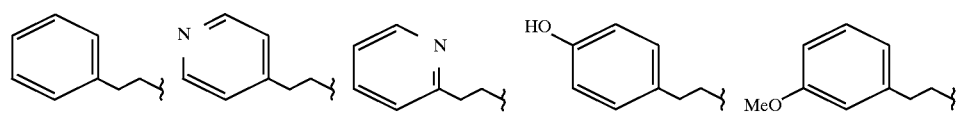
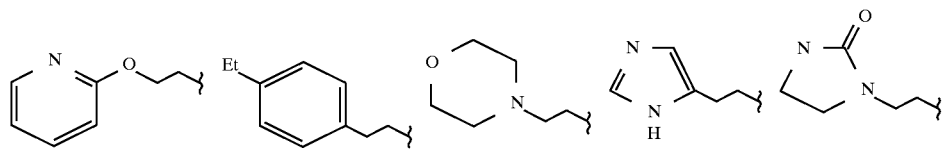
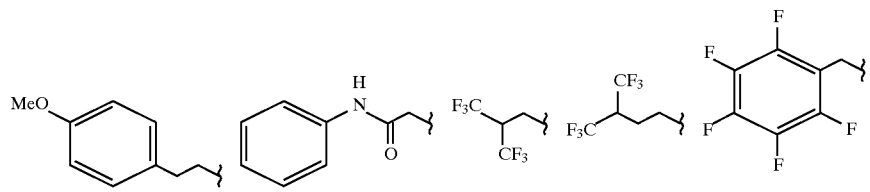

TABLE E
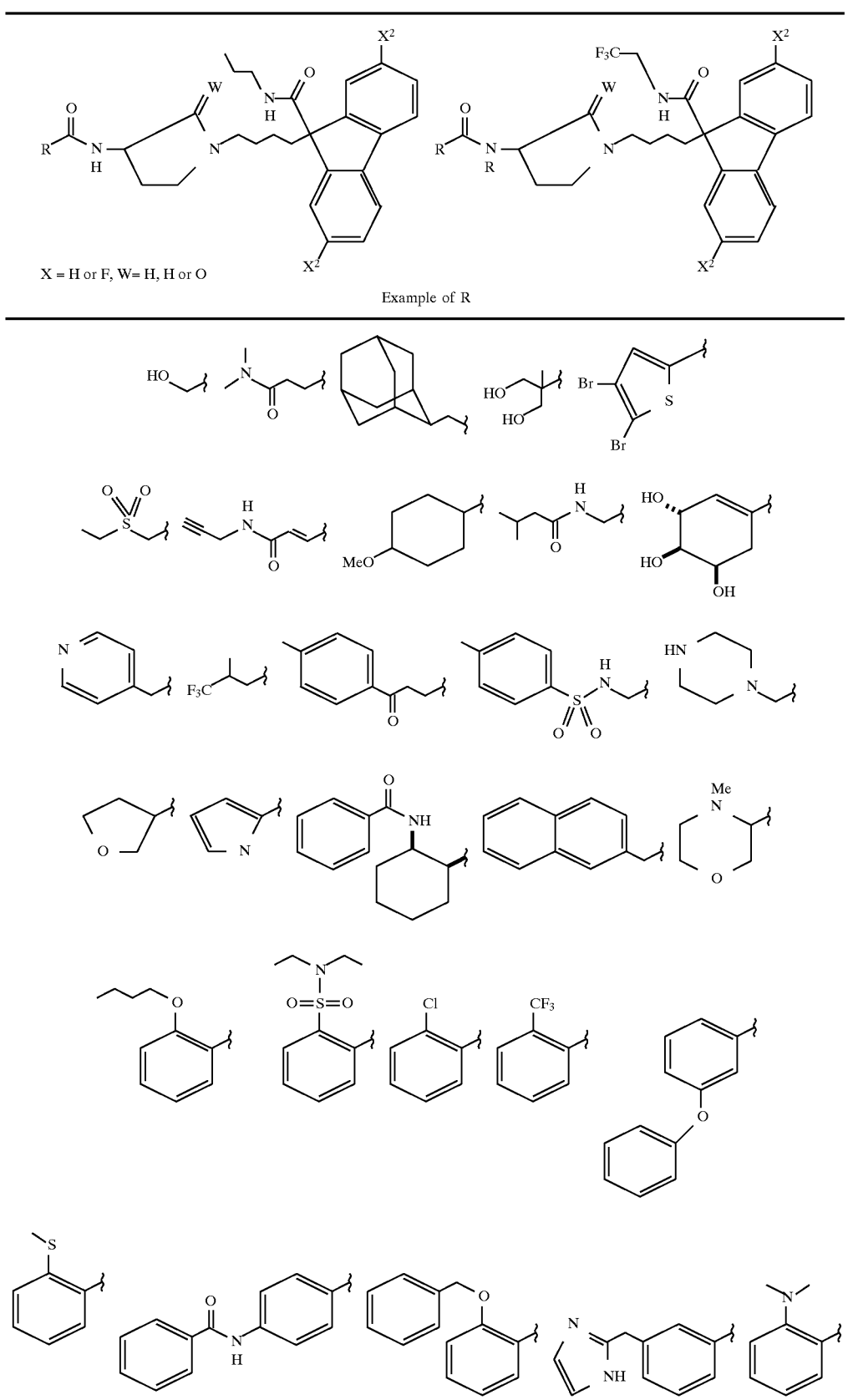
X = H or F, W = H, H or O
Example of R

TABLE E-continued
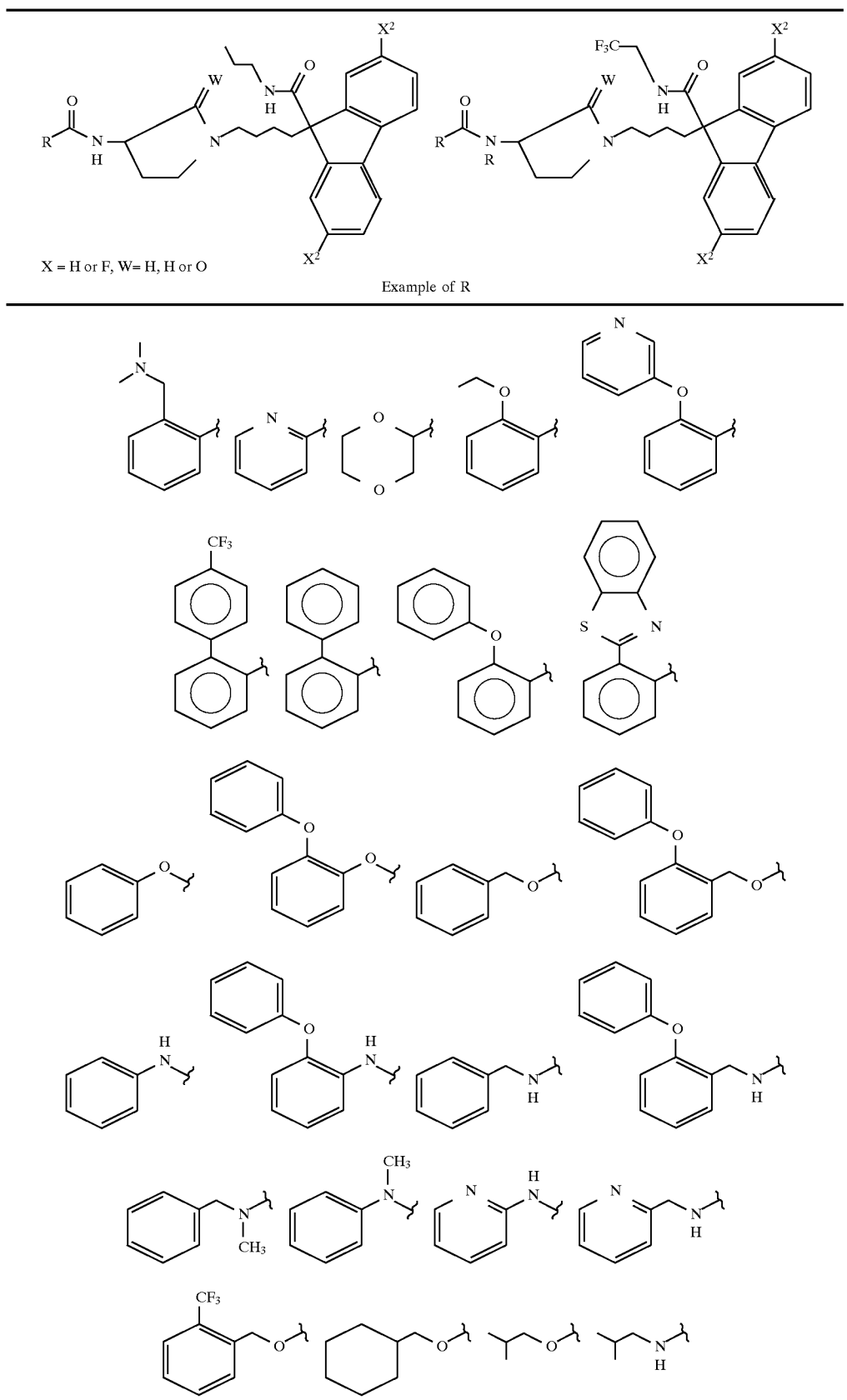
X = H or F, W = H, H or O
Example of R

TABLE E-continued
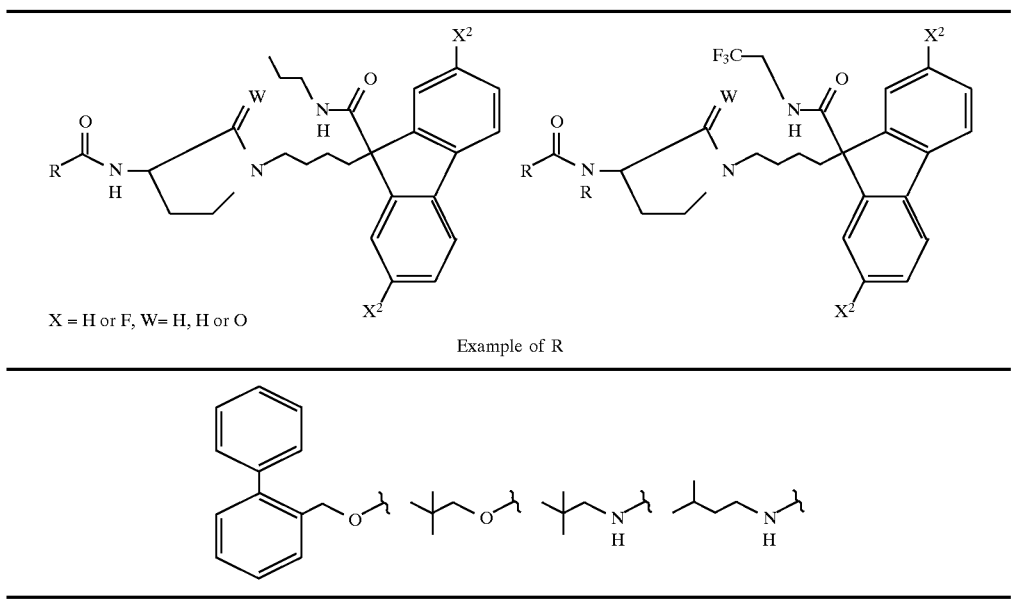
X = H or F, W= H, H or O
Example of R
TABLE F
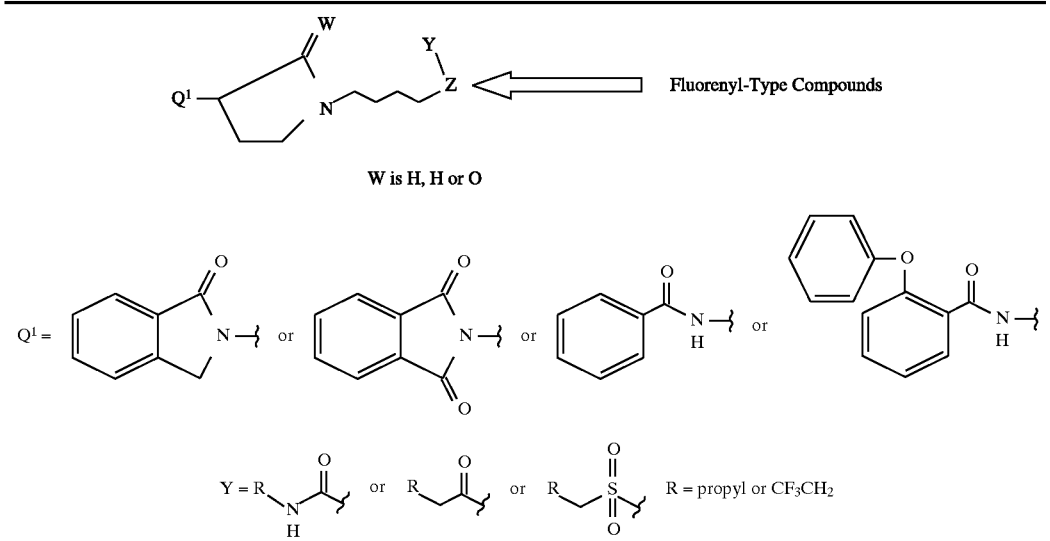
⇐ Fluorenyl-Type Compounds
W is H, H or O
R = propyl or CF$_3$CH$_2$
Fluorenyl-Type Rings: Z =
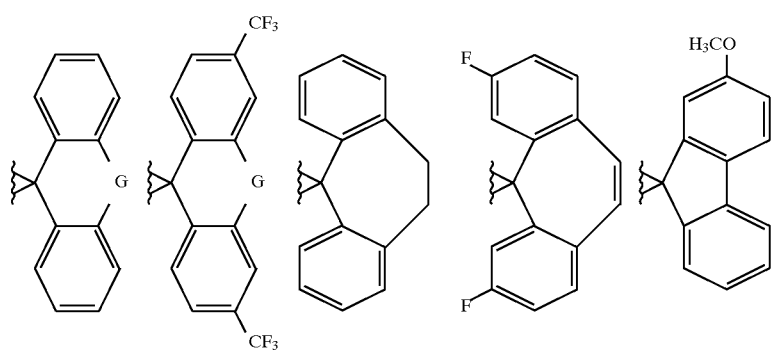
G = CH$_2$, O, S, SO, SO$_2$

TABLE F-continued
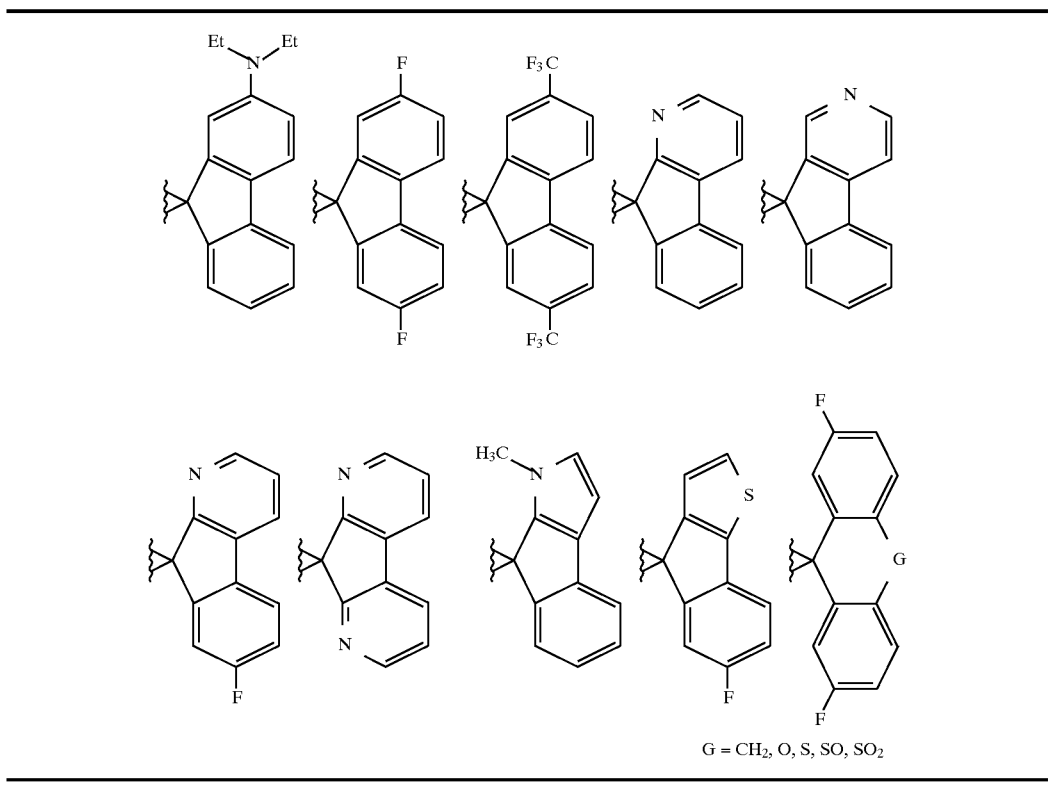
G = CH$_2$, O, S, SO, SO$_2$
TABLE G
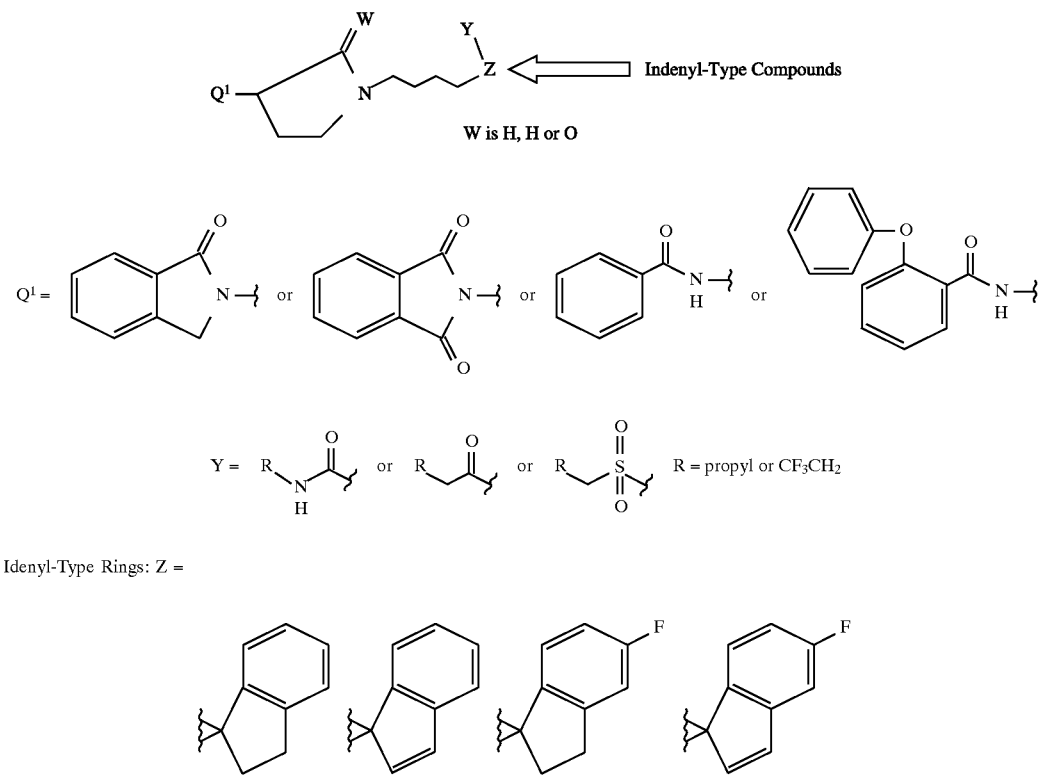

TABLE G-continued
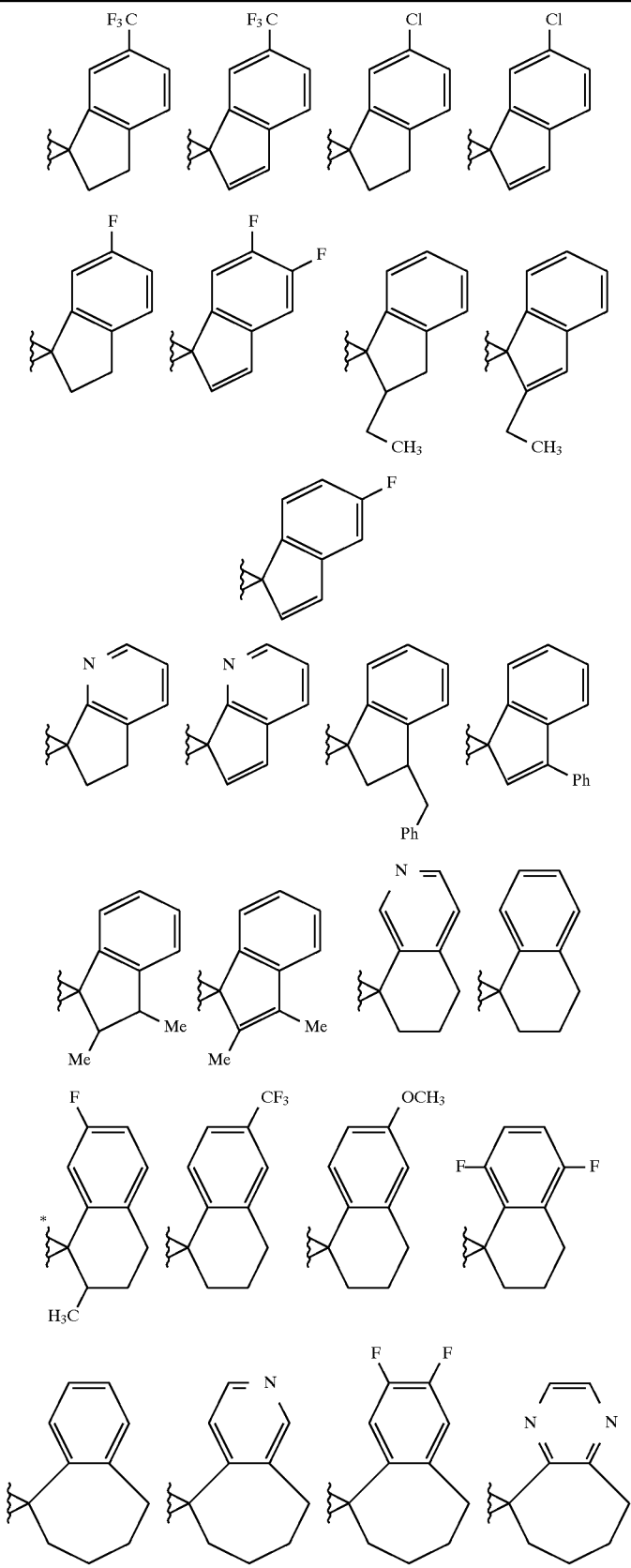

TABLE G-continued
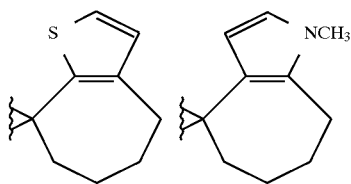
TABLE H
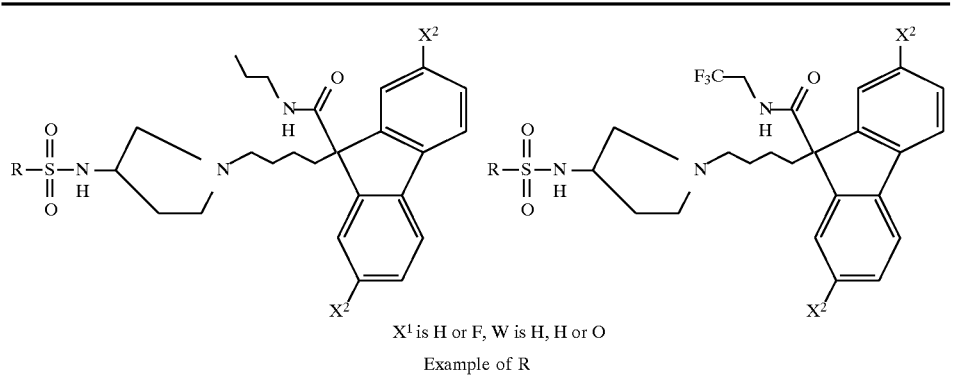
$X^1$ is H or F, W is H, H or O
Example of R
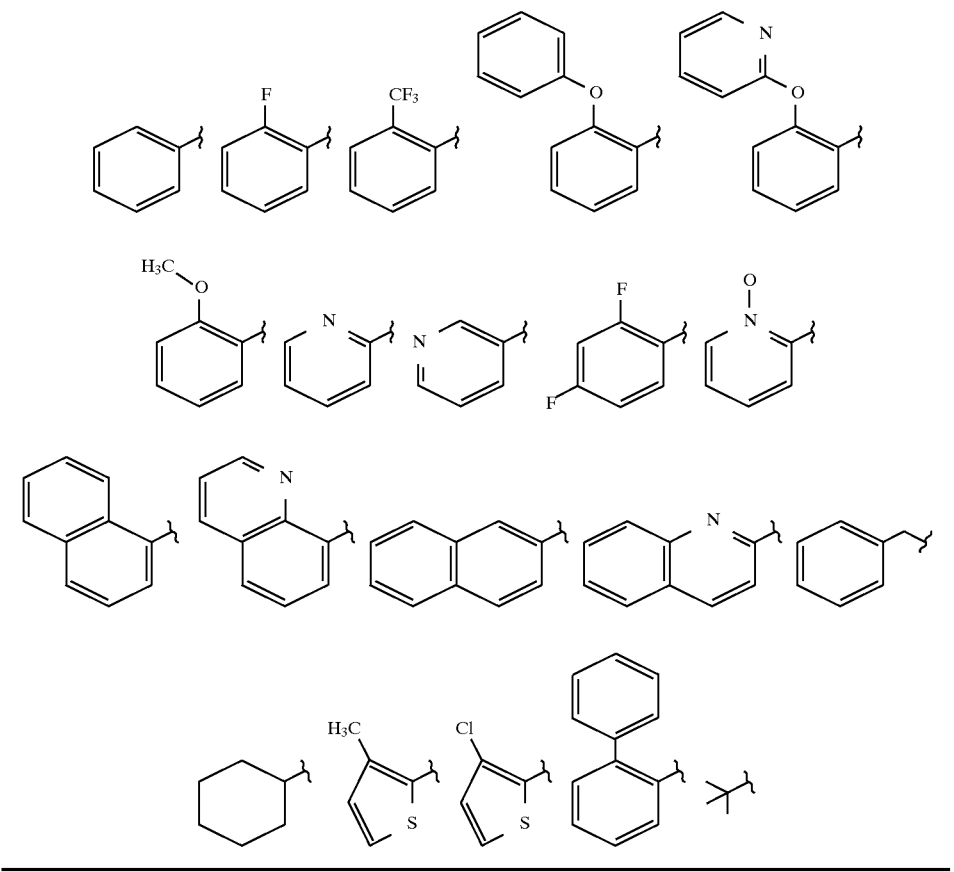

EXAMPLE 337 cis-9-[4-[3-(2,3-Dihydro-1H-isoindol-2-yl)-1-pyrrolidinyl]butyl]-N-propyl-9H-fluorene-9-carboxamide, N-oxide

EXAMPLE 338

2-[1-[4-[9-(Butylsulfonyl)-9H-fluoren-9-yl]butyl]-3-pyrrolidinyl]-2,3-dihydro-1H-isoindol-1-one

EXAMPLE 339

9-[4-[[3-[(1,1-Dimethylethoxy)carbonyl]amino]-1-pyrrolidinyl]butyl]-2,7-difluoro-N-(2,2,2-trifluoroethyl)-9H-fluorene-9-carboxamide

EXAMPLE 340

9-[4-[3-[(2-Phenoxybenzoyl)amino]-1-pyrrolidinyl]-butyl]-N-(2,2,2-trifluoroethyl)-9H-fluorene-9-carboxamide, monohydrochloride

EXAMPLE 341

9-[4-[[3-(Benzoylamino)-1-pyrrolidinyl]butyl]-2,7-difluoro-N-(2,2,2-trifluoroethyl)-9H-fluorene-9-carboxamide

EXAMPLE 342

9-[4-[[3-(1,3-Dihydro-1,3-dioxo-2H-isoindol-2-yl)-1-pyrrolidinyl]butyl]-2,7-difluoro-N-(2,2,2-trifluoroethyl)-9H-fluorene-9-carboxamide

EXAMPLE 343

2,7-Difluoro-9-[4-[[3-[(2-phenoxybenzoyl)amino]-1-pyrrolidinyl]butyl]-N-(2,2,2-trifluoroethyl)-9H-fluorene-9-carboxamide

EXAMPLE 344

9-[4-[3-(Benzoylamino)-1-pyrrolidinyl]butyl]-N-(2,2,2-trifluoroethyl)-9H-fluorene-9-carboxamide, monohydrochloride

EXAMPLE 345

2,3-Dihydro-2-[1-[4-[9-(1-oxopentyl)-9H-fluoren-9-yl]butyl]-3-pyrrolidinyl]-1H-isoindol-1-one, monohydrochloride

EXAMPLE 346

2,3-Dihydro-2-[1-(1-oxo-3,3-diphenylpropyl)-3-pyrrolidinyl]-1H-isoindol-1-one

EXAMPLE 347

[1-[4-[9-[(Propylamino)carbonyl]-9H-fluoren-9-yl]-butyl]-3-pyrrolidinyl]carbamic acid, phenylmethyl ester, monohydrochloride

EXAMPLE 348

9-[4-[3-(2,3-Dihydro-1-oxo-1H-isoindol-2-yl)-1-pyrrolidinyl]butyl]-N-(2,2,2-trifluoroethyl)-9H-fluorene-9-carboxamide, hydrochloride salt

EXAMPLE 349

9-[4-[3-(2,3-Dihydro-1-oxo-1H-isoindol-2-yl)-1-pyrrolidinyl]butyl]-N-(2,2,2-trifluoroethyl)-9H-fluorene-9-carboxamide, hydrochloride salt

EXAMPLE 350

9-[4-[3-(Benzoylamino)-1-pyrrolidinyl]butyl]-N-propyl-9H-fluorene-9-carboxamide

EXAMPLE 351

9-[4-[3-(1,3-Dihydro-1,3-dioxo-2H-isoindol-2-yl)-1-pyrrolidinyl]-butyl]-N-propyl-9H-fluorene-9-carboxamide

EXAMPLE 352

9-[4-[3-(2,3-Dihydro-1-oxo-1H-isoindol-2-yl)-1-pyrrolidinyl]butyl]-N-(2,2,3,3,4,4,4-heptafluorobutyl)-9H-fluorene-9-carboxamide, monohydrochloride

EXAMPLE 353

9-[4-[[3-[(1,1-Dimethylethoxy)carbonyl]amino]-1-pyrrolidinyl]butyl]-3,6-difluoro-N-(2,2,2-trifluoroethyl)-9H-fluorene-9-carboxamide

EXAMPLE 354

1-[4-[3-(1,3-Dihydro-1-oxo-2H-isoindol-2-yl)-1-pyrrolidinyl]butyl]-2-methyl-N-(2,2,2-trifluoroethyl)-1H-indene-1-carboxamide

EXAMPLE 355

9-[4-[3-(1,3-Dihydro-1-oxo-2H-isoindol-2-yl)-1-pyrrolidinyl]butyl]-N-(2,2,3,3,3-pentafluoropropyl)-9H-fluorene-9-carboxamide, monohydrochloride

EXAMPLE 356

1-[4-[3-(1,3-Dihydro-1-oxo-2H-isoindol-2-yl)-1-pyrrolidinyl]butyl]-N-(2,2,2-trifluoroethyl)-1H-indene-1-carboxamide

EXAMPLE 357

9-[4-[3-(Benzoylamino)-1-pyrrolidinyl]butyl]-3,6-difluoro-N-(2,2,2-trifluoroethyl)-9H-fluorene-9-carboxamide

EXAMPLE 358

3,6-Difluoro-9-[4-[3-[(2-phenoxybenzoyl)amino]-1-pyrrolidinyl]butyl]-N-(2,2,2-trifluoroethyl)-9H-fluorene-9-carboxamide Please note that in the Examples 359 to 477 for structures bearing only two single bonded substituents to nitrogen, the third substituent is always hydrogen, but it is not shown explicitly in the structures. Also, please note that in the Examples 359 to 475 for structures bearing oxygen and sulfurs with only one single bonded substituent, the second substituent is always hydrogen, but is not shown explicitly in the structures.

| Example No. | |
|---|---|
| 359 | 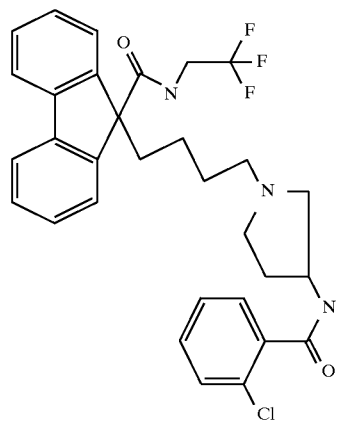 |
| 360 | 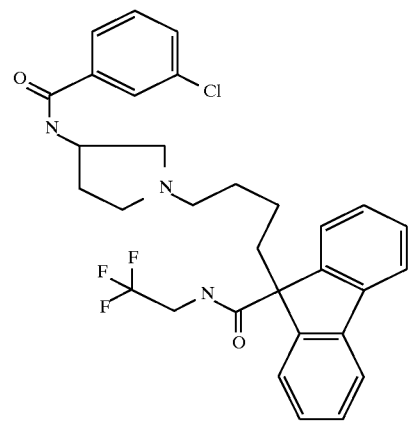 |

| Example No. | |
|---|---|
| 361 | 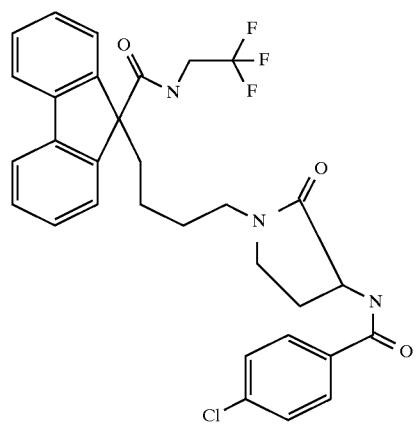 |
| 362 | 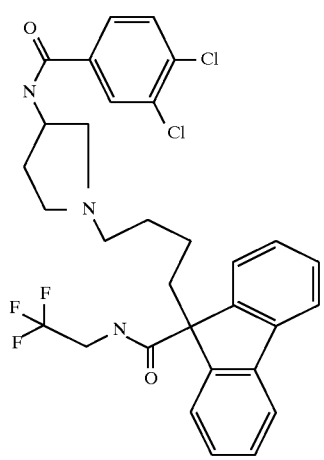 |
| 363 | 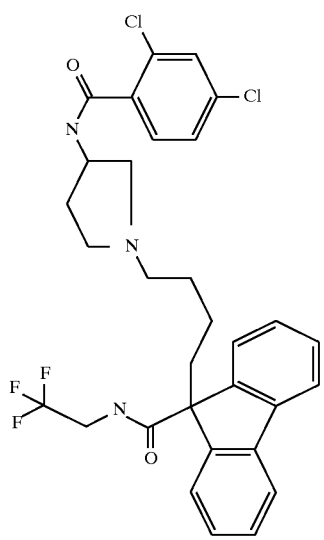 |

| Example No. | |
|---|---|
| 364 | 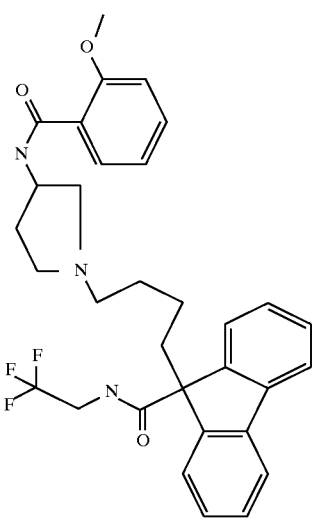 |
| 365 | 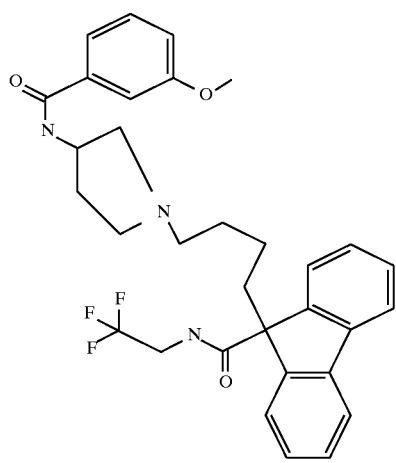 |
| 366 | 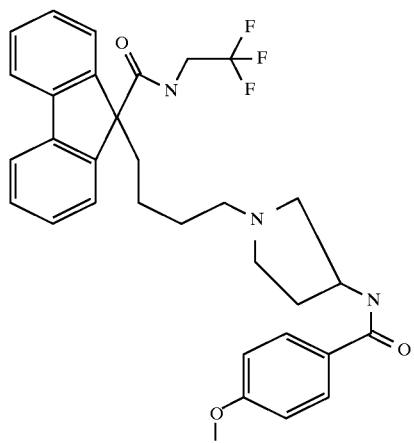 |

-continued
| Example No. | |
|---|---|
| 367 | 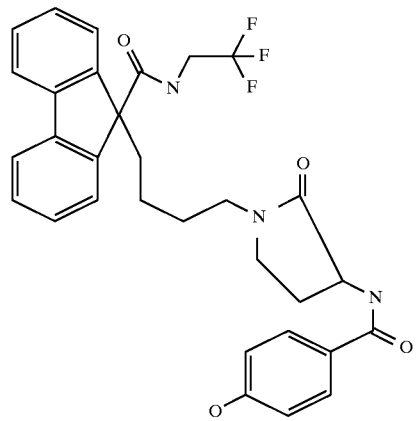 |
| 368 | 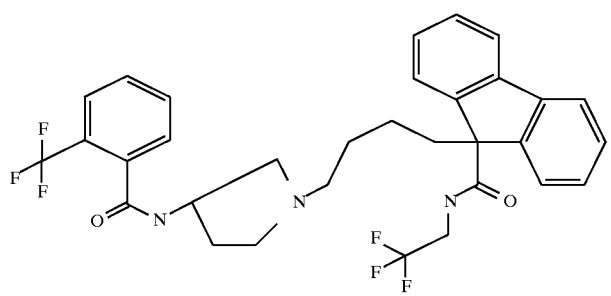 |
| 369 | 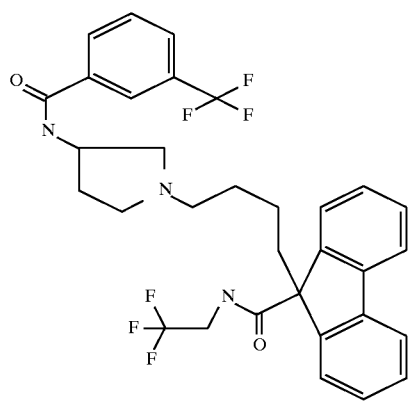 |
| 370 | 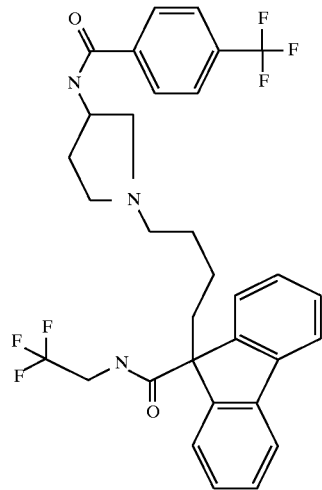 |

| Example No. |
|---|
| 371 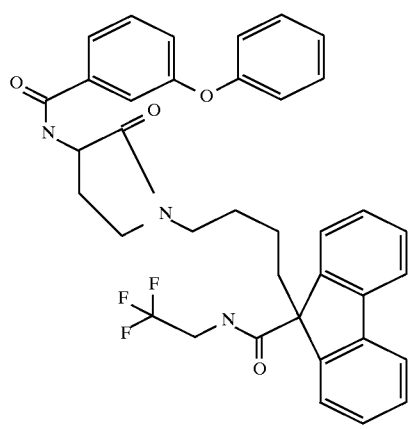 |
| 372 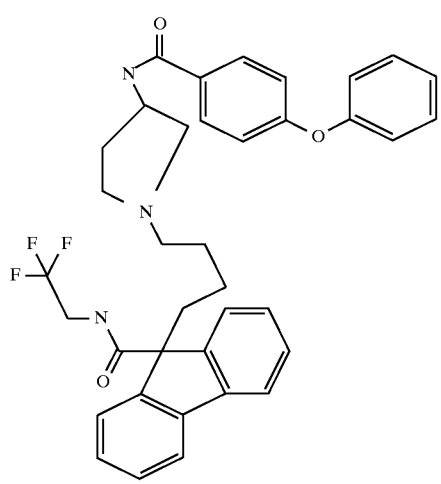 |
| 373 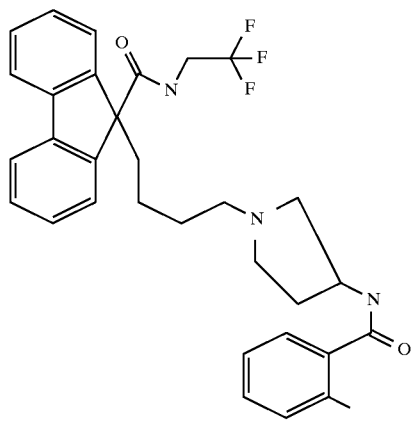 |

-continued
| Example No. | |
|---|---|
| 374 | 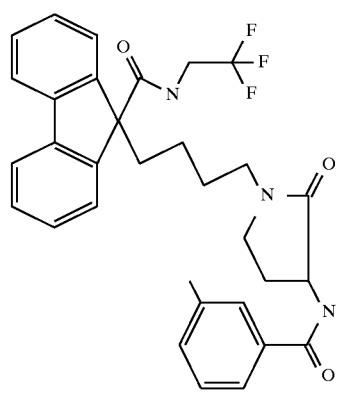 |
| 375 | 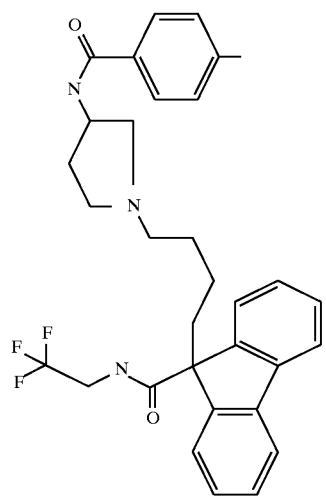 |
| 376 | 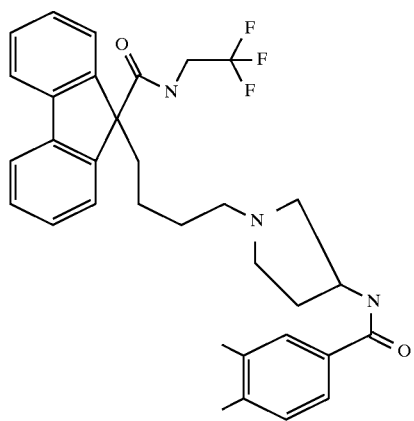 |

| Example No. | |
|---|---|
| 377 | 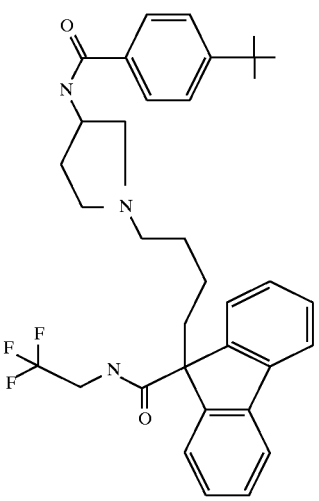 |
| 378 | 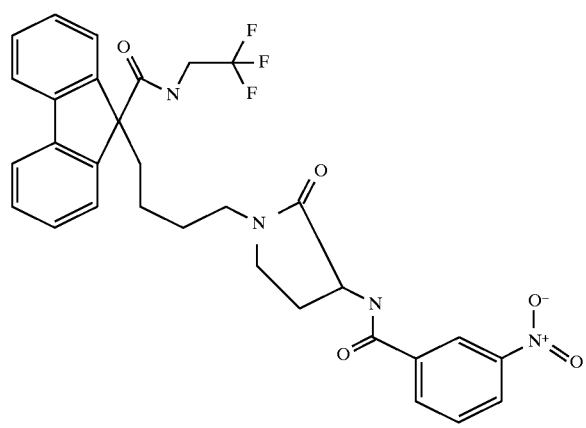 |
| 379 | 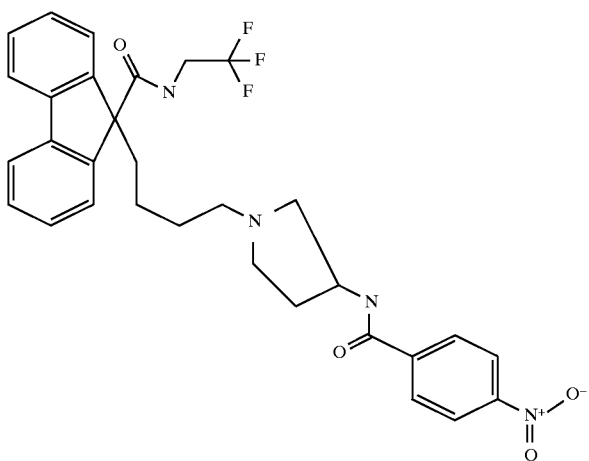 |

| Example No. | |
|---|---|
| 380 | 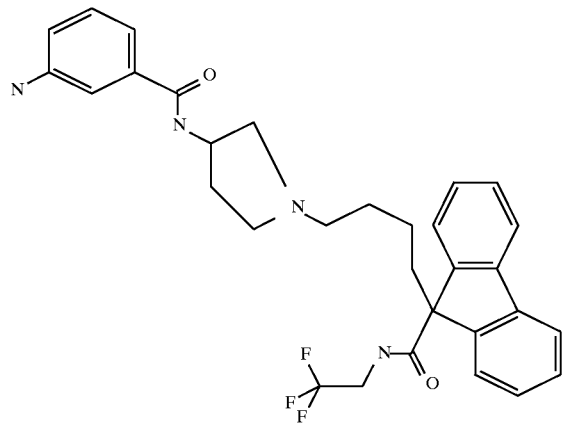 |
| 381 | 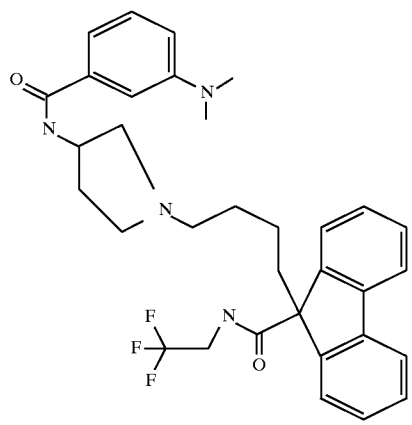 |
| 382 | 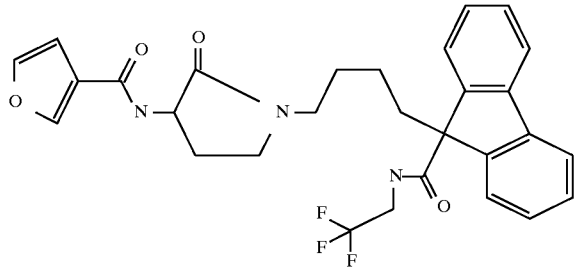 |
| 383 | 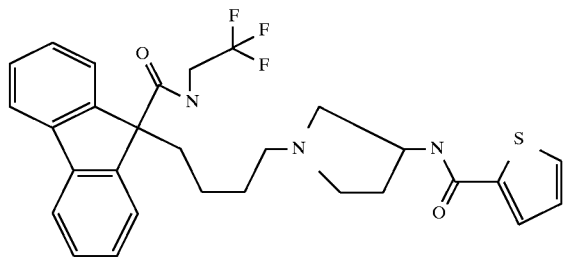 |

| Example No. | |
|---|---|
| 384 | 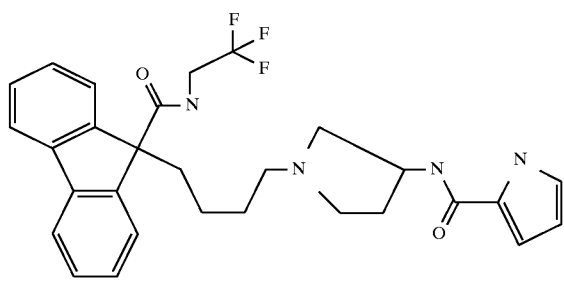 |
| 385 | 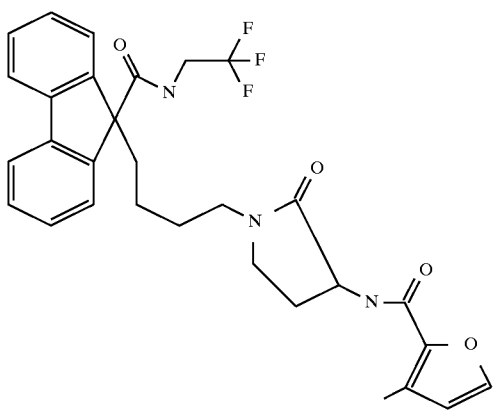 |
| 386 | 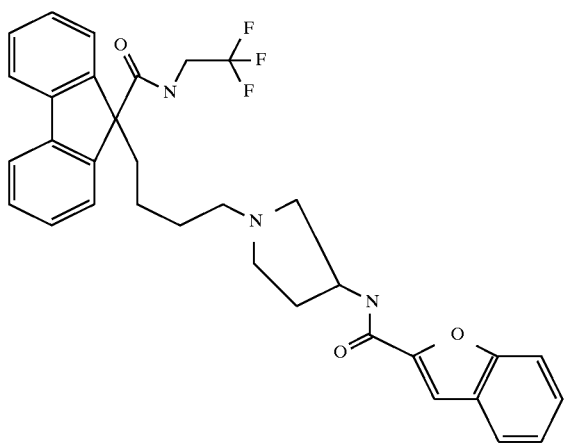 |
| 387 | 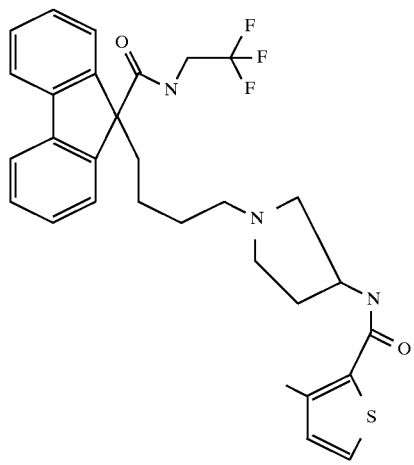 |

| Example No. | |
|---|---|
| 388 | 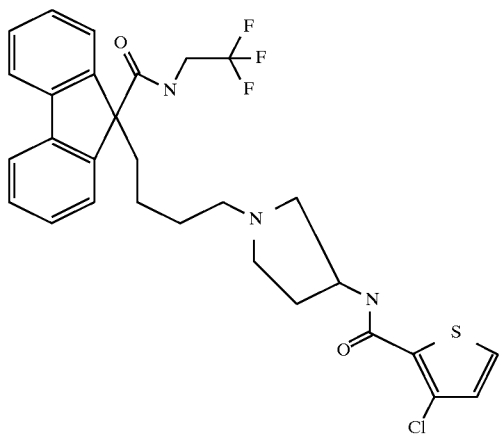 |
| 389 | 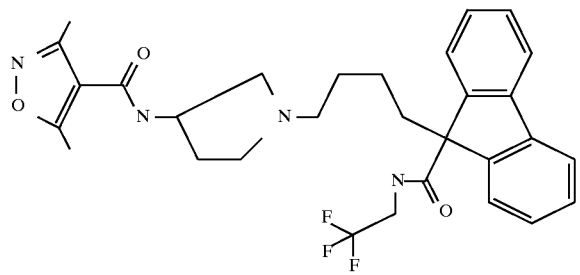 |
| 390 | 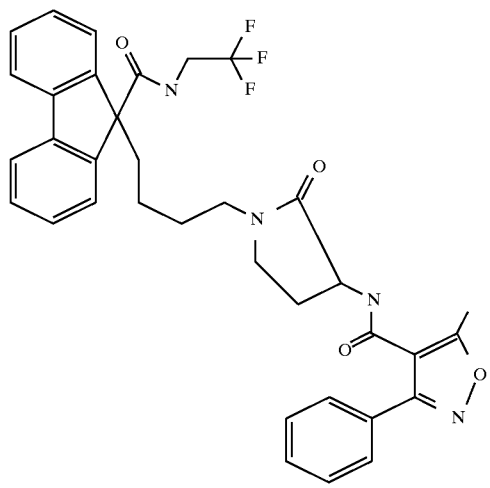 |
| 391 | 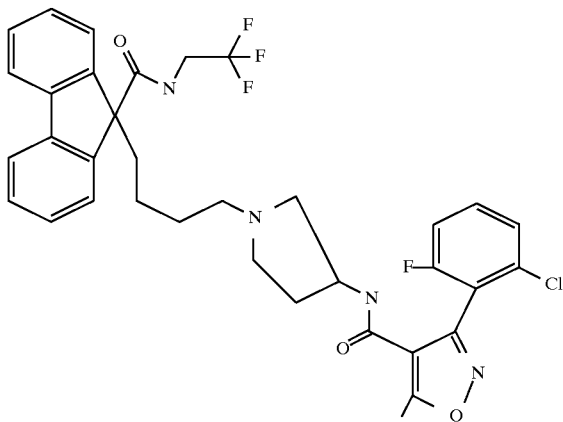 |

| Example No. | |
|---|---|
| 392 | 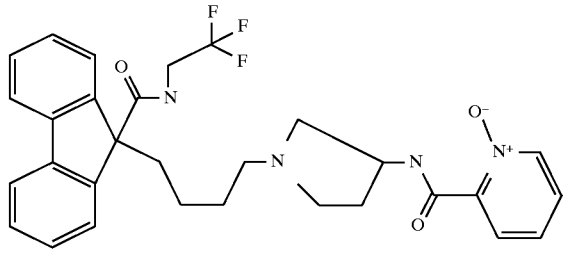 |
| 393 | 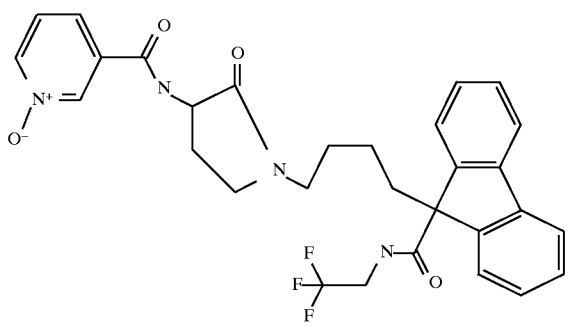 |
| 394 | 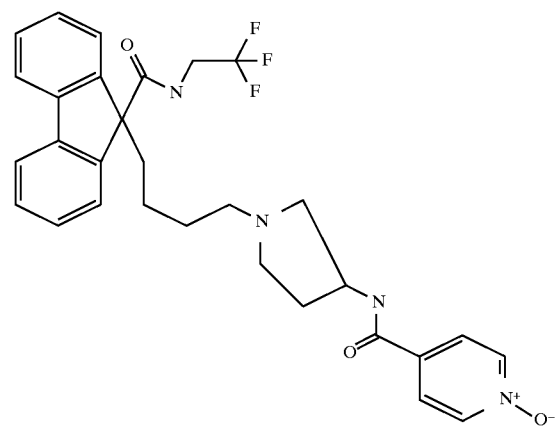 |
| 395 | 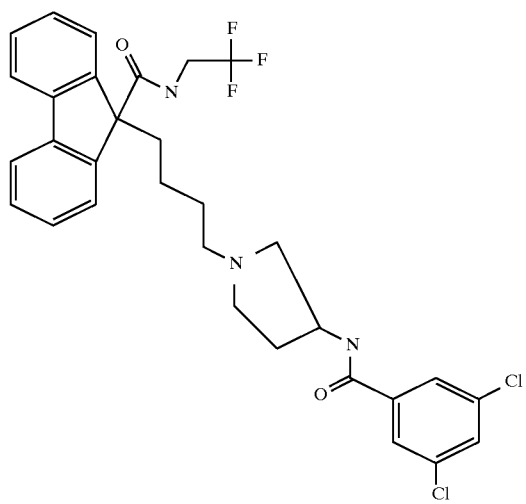 |

| Example No. | |
|---|---|
| 396 | 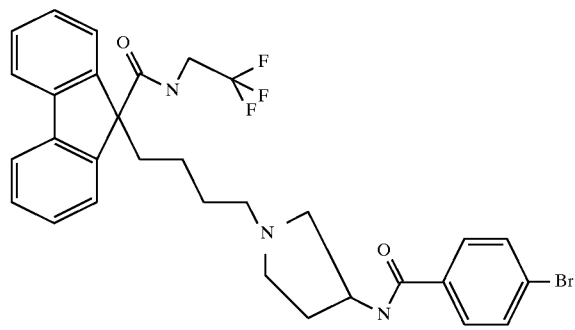 |
| 397 | 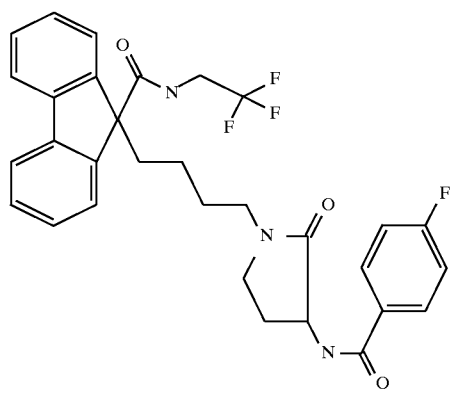 |
| 398 | 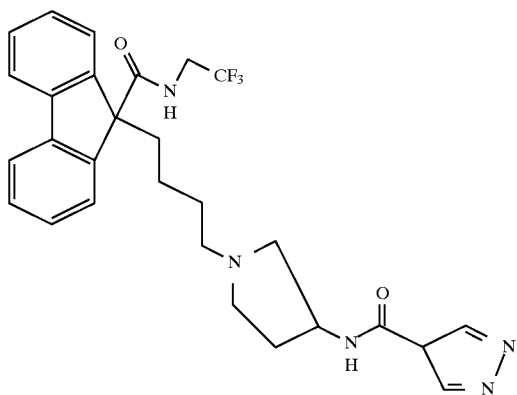 |
| 399 | 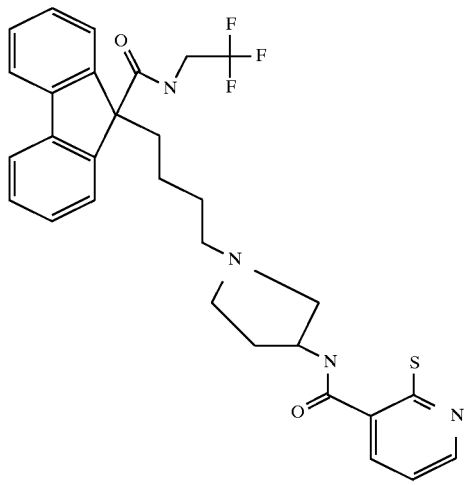 |

-continued
| Example No. | |
|---|---|
| 400 | 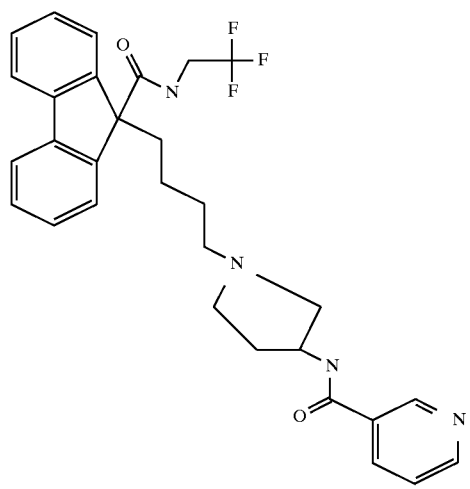 |
| 401 | 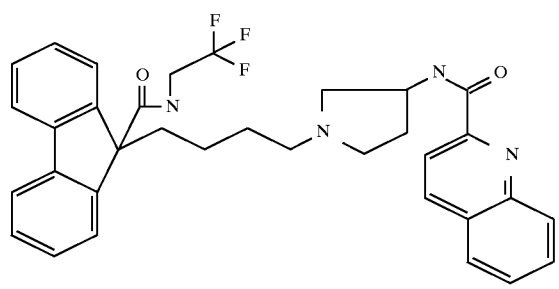 |
| 402 | 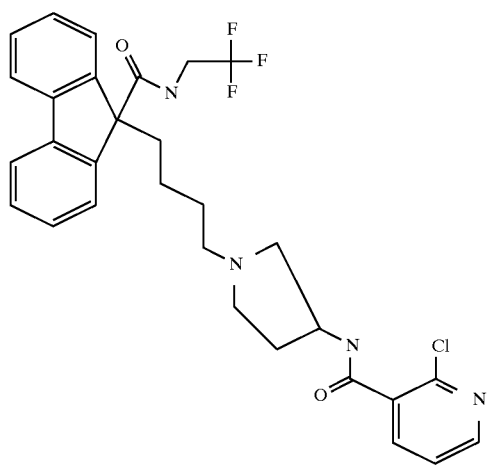 |
| 403 | 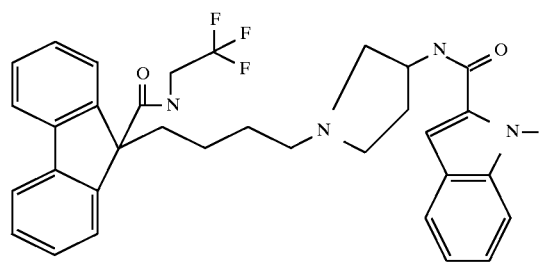 |

-continued
| Example No. | |
|---|---|
| 404 | 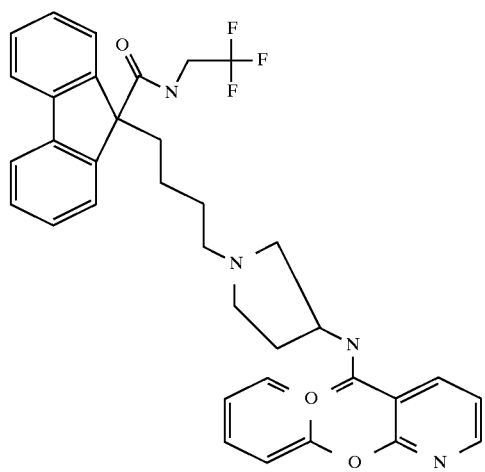 |
| 405 | 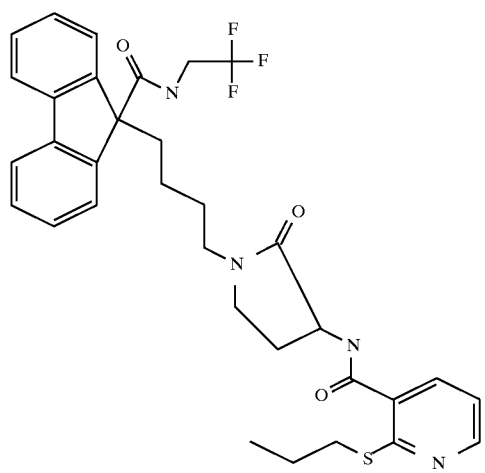 |
| 406 | 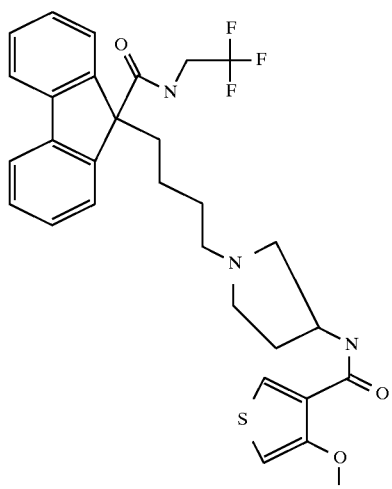 |

| Example No. | |
|---|---|
| 407 | 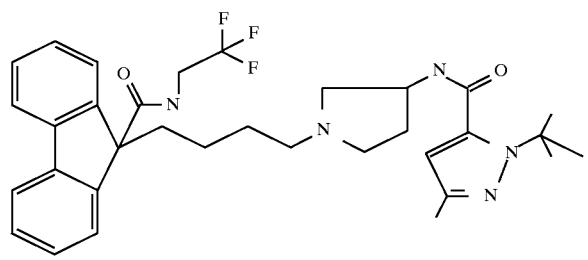 |
| 408 | 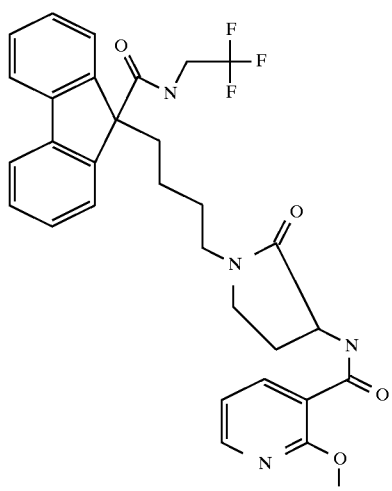 |
| 409 | 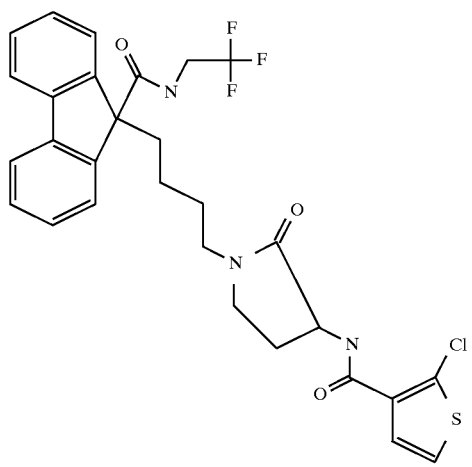 |
| 410 | 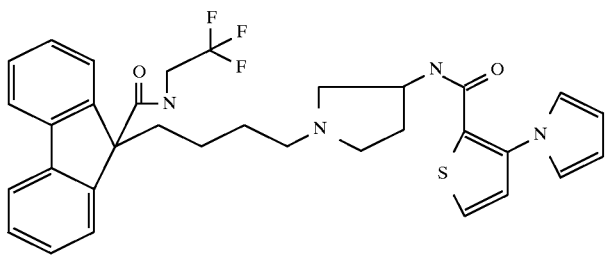 |

| Example No. | |
|---|---|
| 411 | 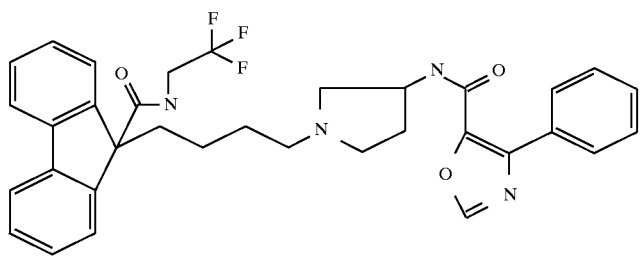 |
| 412 | 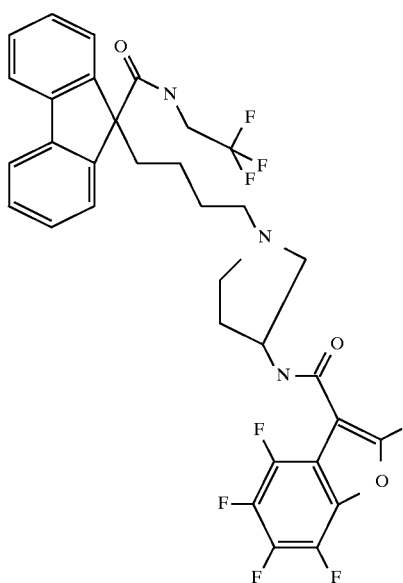 |
| 413 | 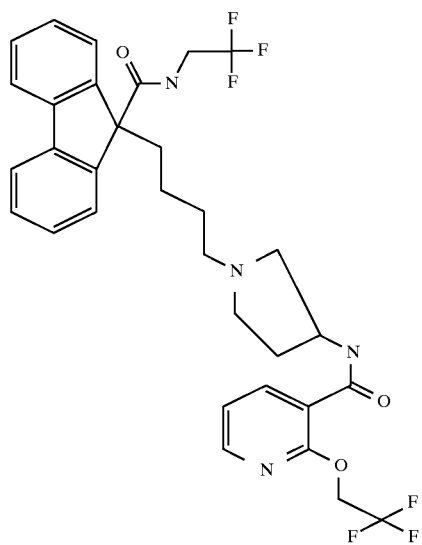 |

-continued
| Example No. |
|---|
| 414 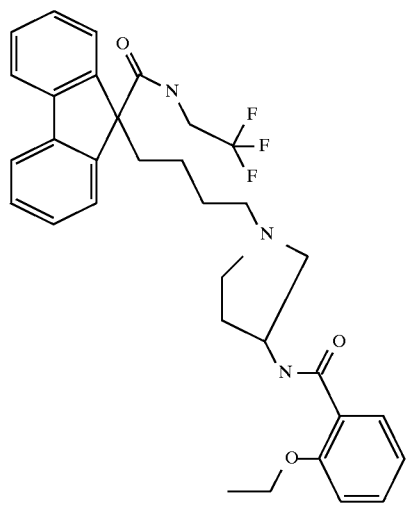 |
| 415 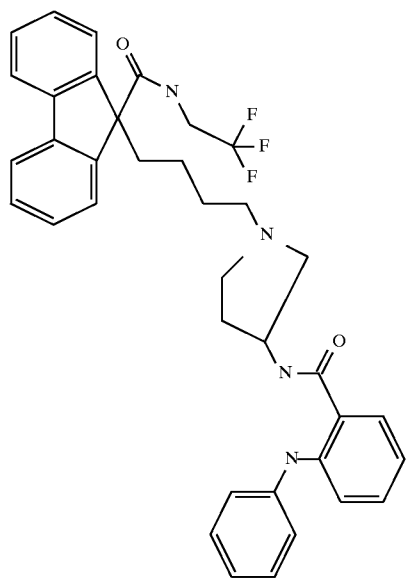 |
| 416 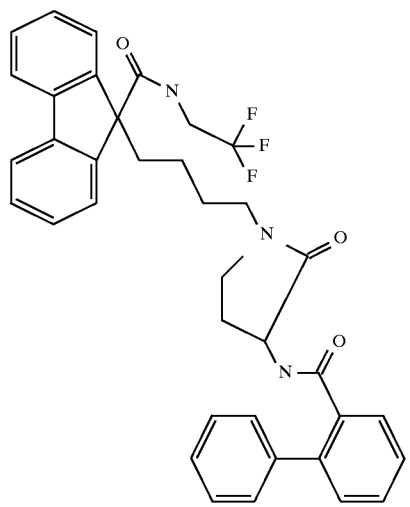 |

| Example No. | |
|---|---|
| 417 | 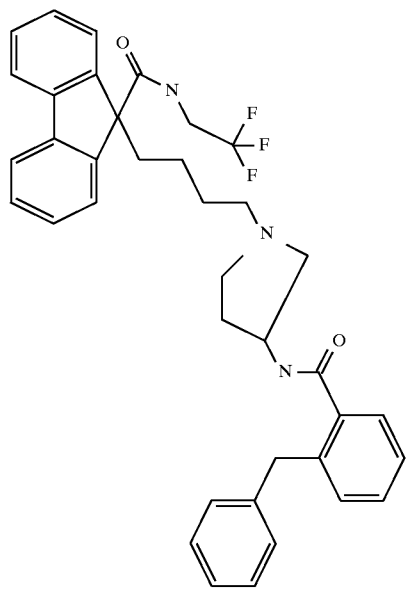 |
| 418 | 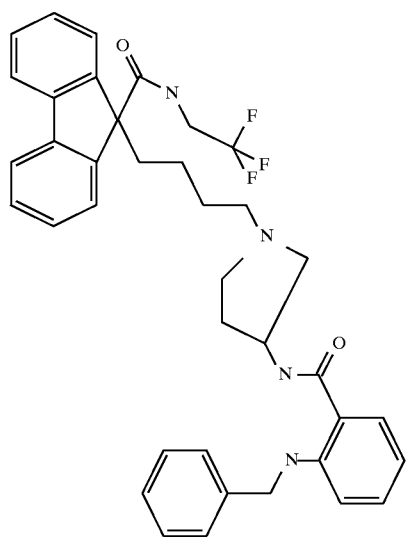 |

| Example No. | |
|---|---|
| 419 | 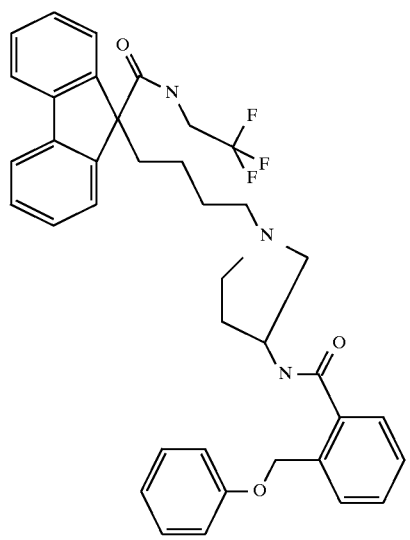 |
| 420 | 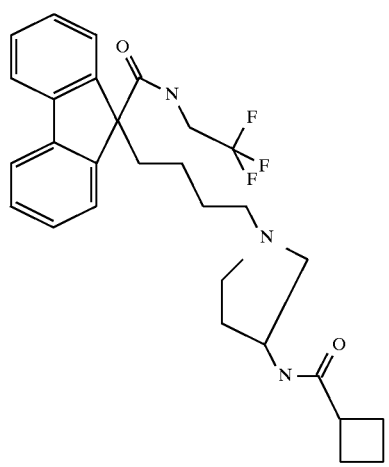 |
| 421 | 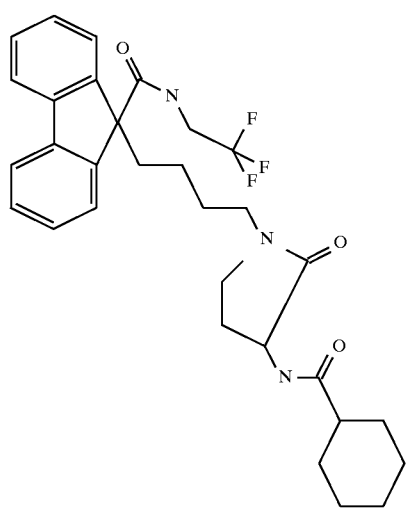 |

| Example No. | |
|---|---|
| 422 | 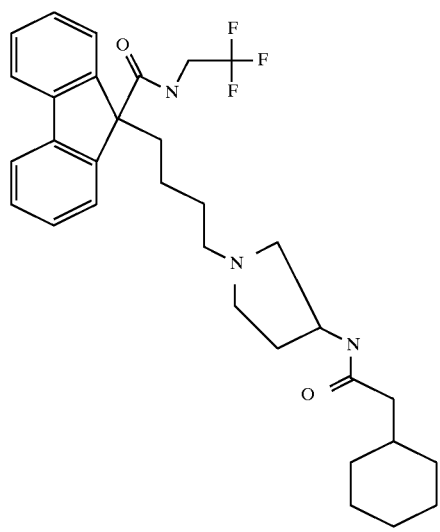 |
| 423 | 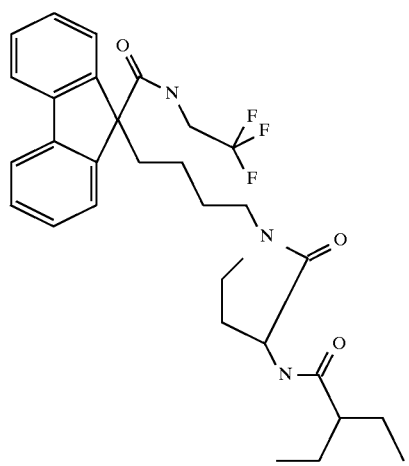 |
| 424 | 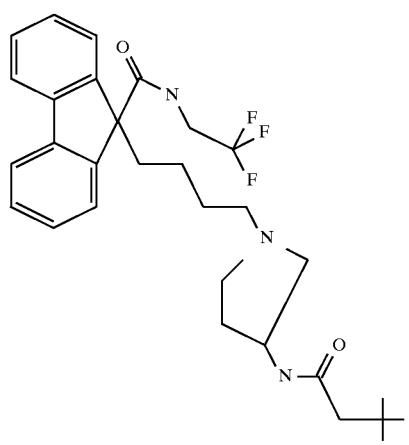 |

|  |
|---|
| Example No. |
425 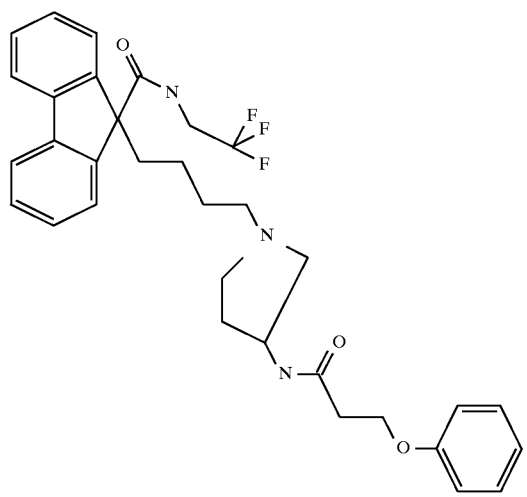
426 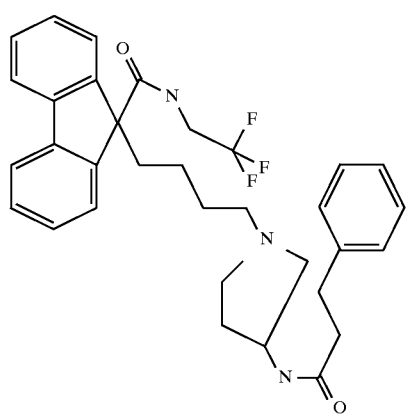
427 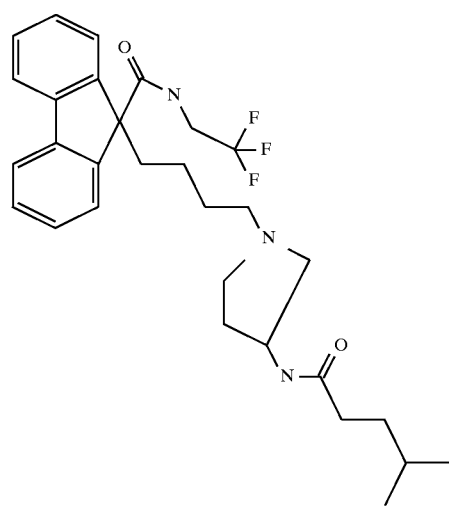

-continued
| Example No. | |
|---|---|
| 428 | 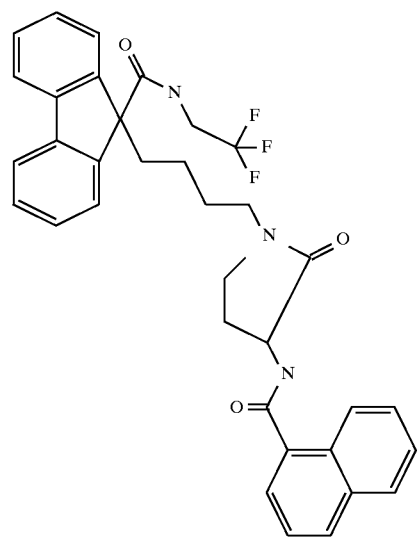 |
| 429 | 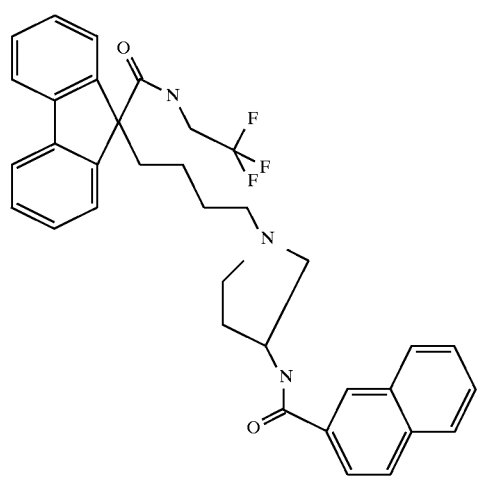 |
| 430 | 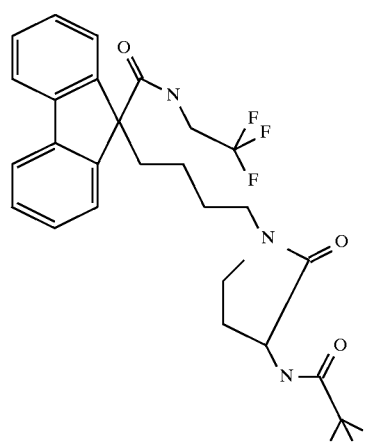 |

-continued
| Example No. | |
|---|---|
| 431 | 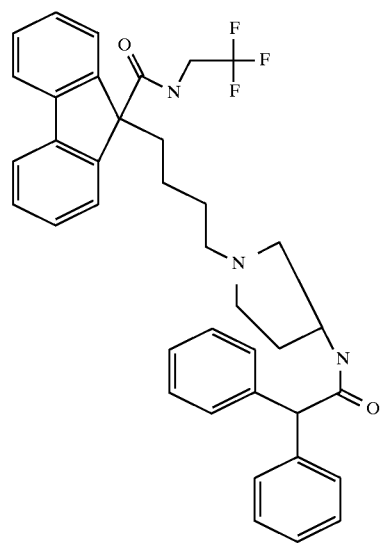 |
| 432 | 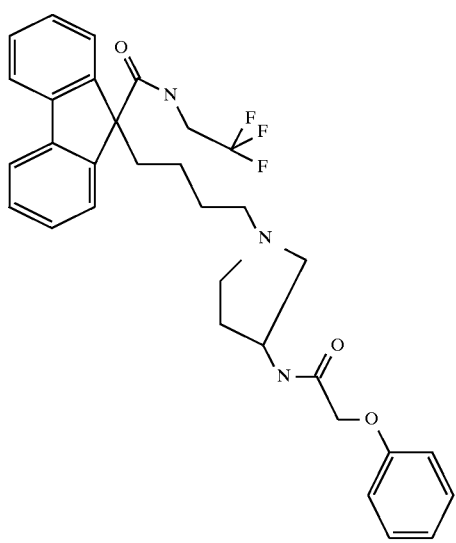 |
| 433 | 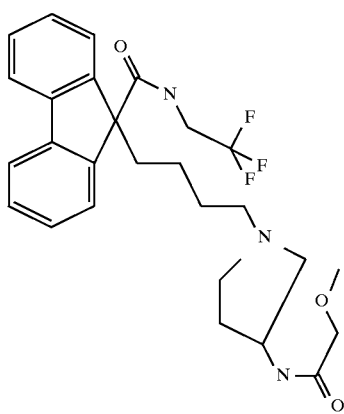 |

-continued
| Example No. | |
|---|---|
| 434 | 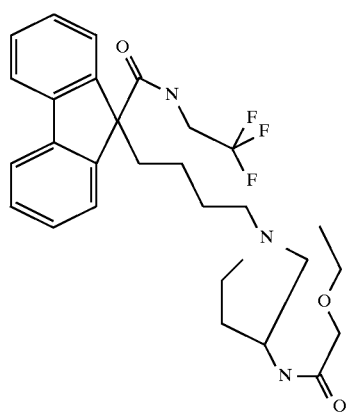 |
| 435 | 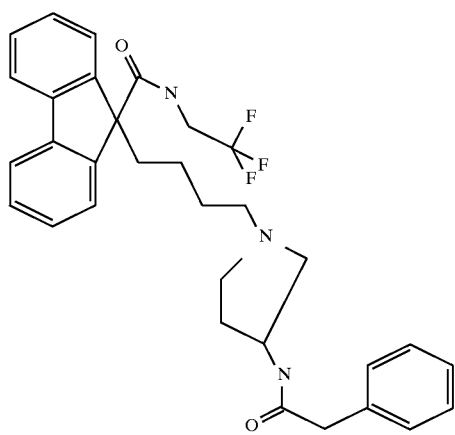 |
| 436 | 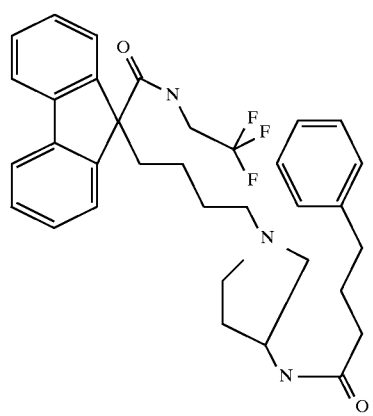 |

| Example No. | |
|---|---|
| 437 | 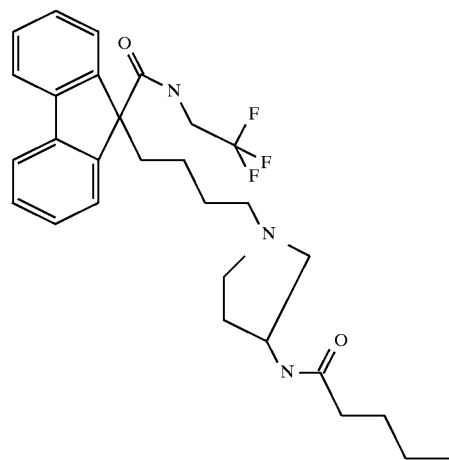 |
| 438 | 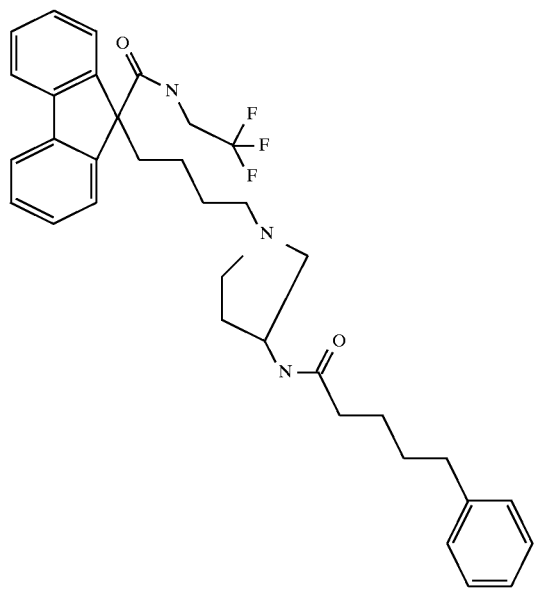 |
| 439 | 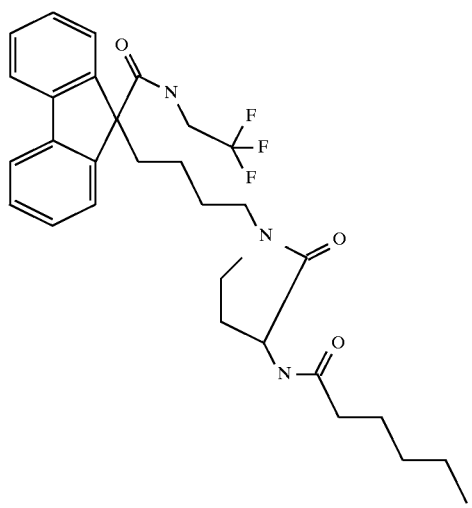 |

| Example No. | |
|---|---|
| 440 | 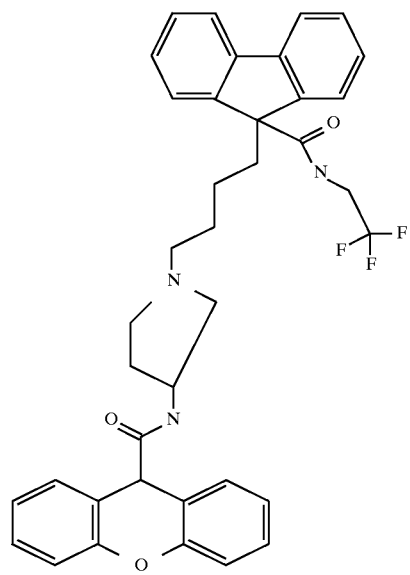 |
| 441 | 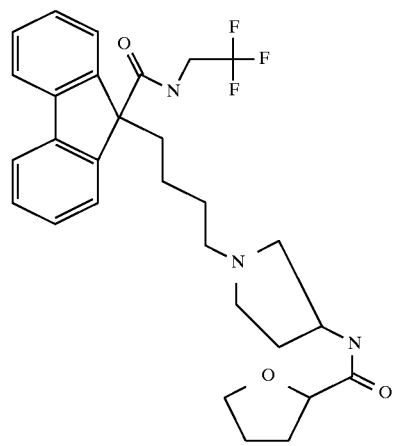 |
| 442 | 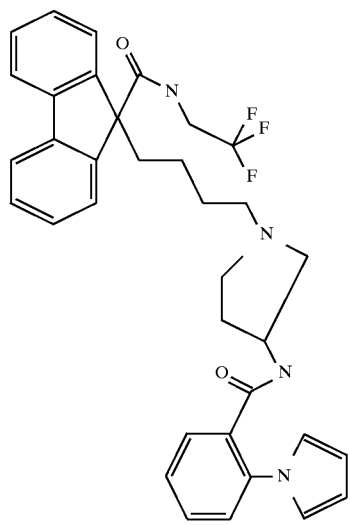 |

-continued
| Example No. | |
|---|---|
| 443 | 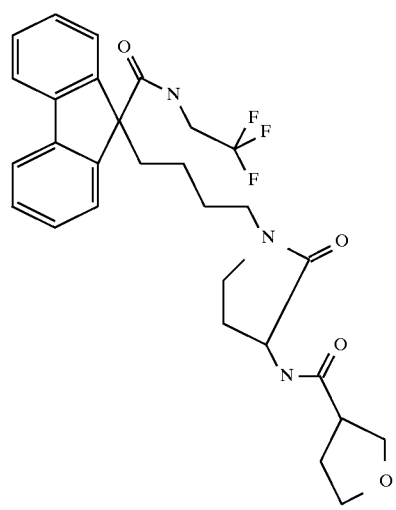 |
| 444 | 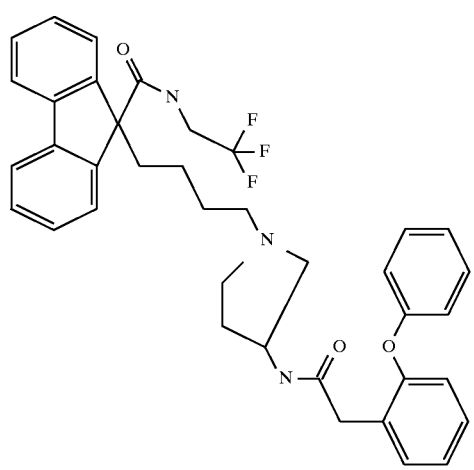 |
| 445 | 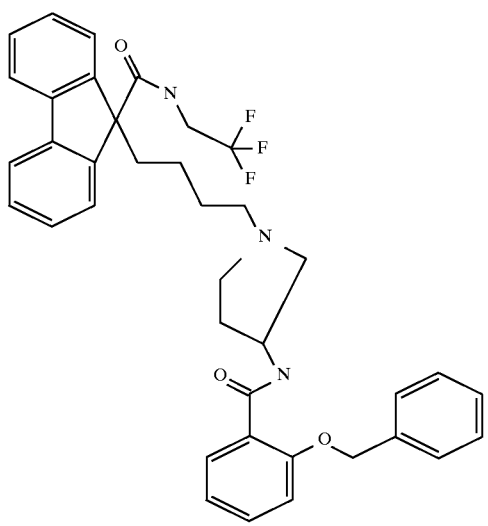 |

| Example No. | |
|---|---|
| 446 | 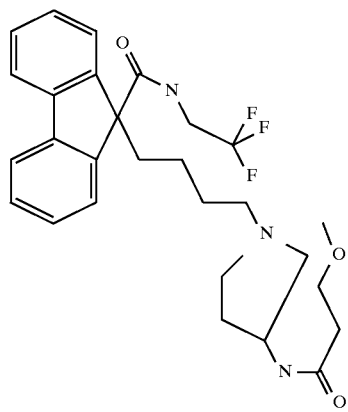 |
| 447 | 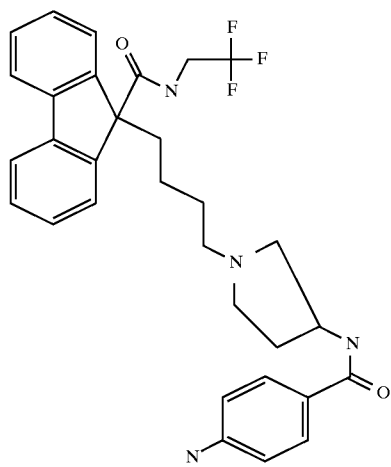 |
| 448 | 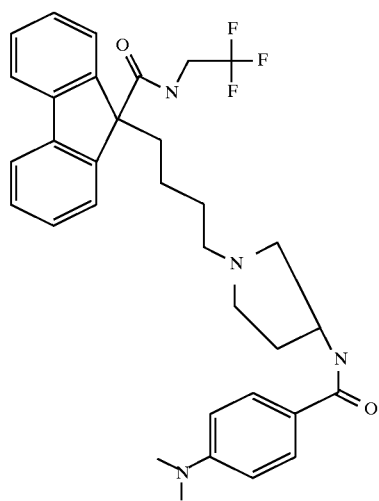 |

| Example No. | |
|---|---|
| 449 | 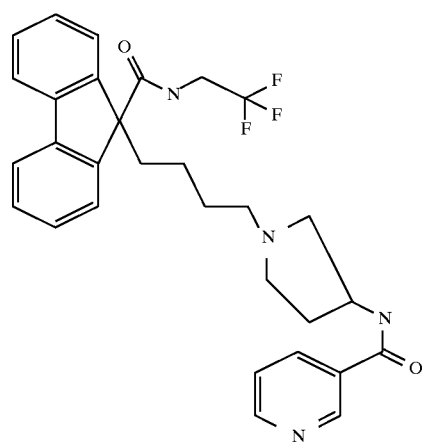 |
| 450 | 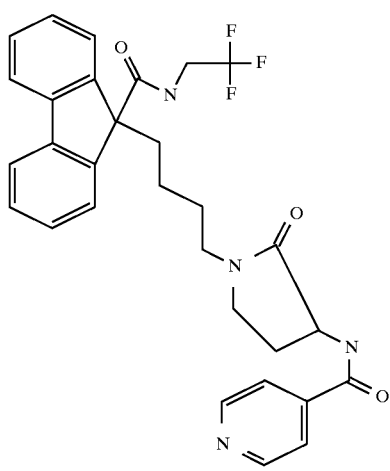 |
| 451 | 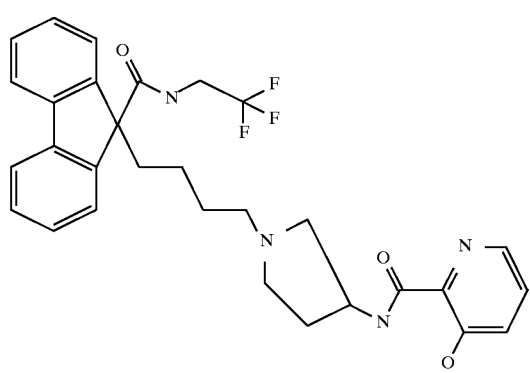 |

| Example No. | |
|---|---|
| 452 | 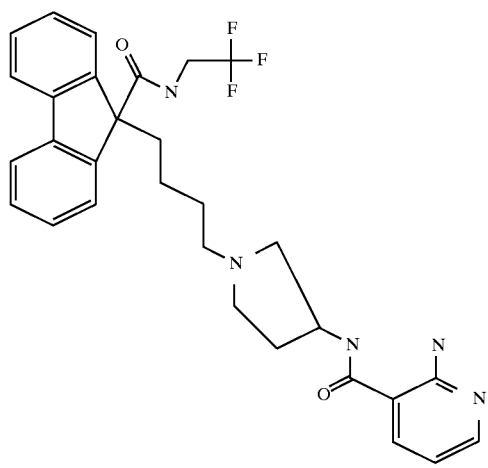 |
| 453 | 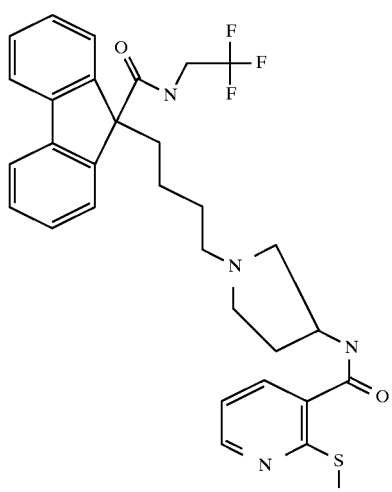 |
| 454 | 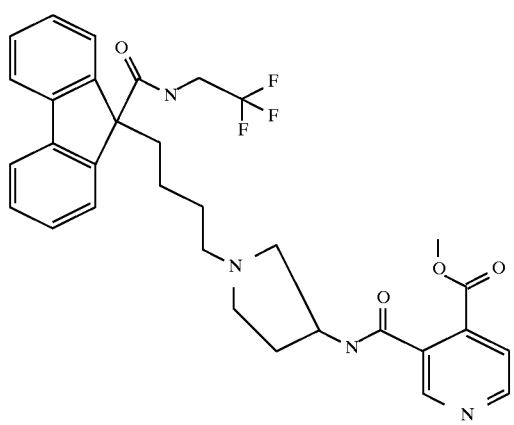 |

| Example No. | |
|---|---|
| 455 | 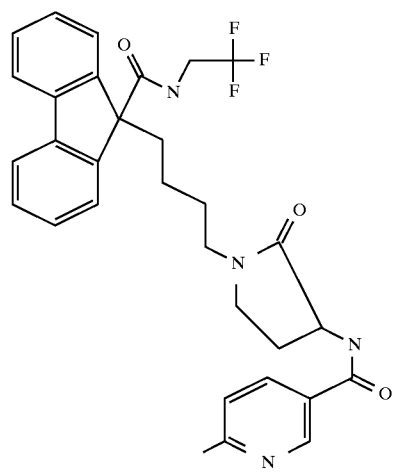 |
| 456 | 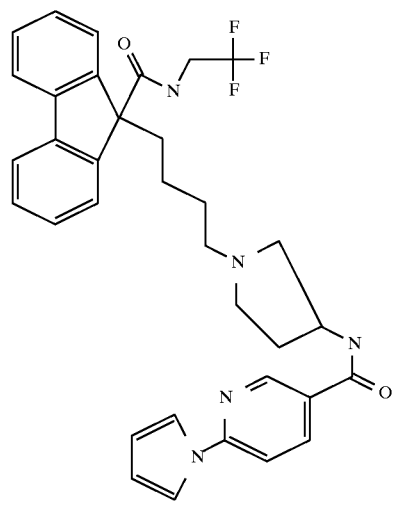 |
| 457 | 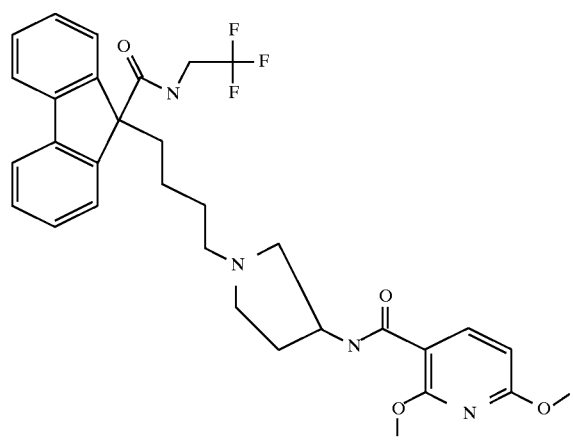 |

-continued
| Example No. | |
|---|---|
| 458 | 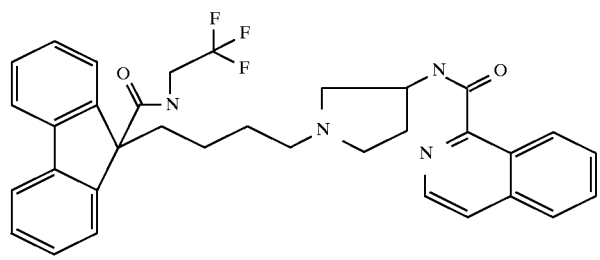 |
| 459 | 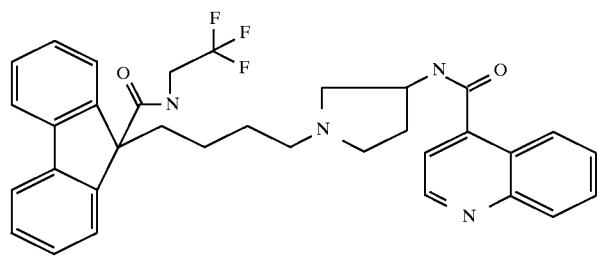 |
| 460 | 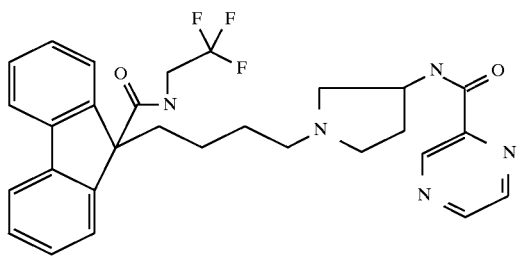 |
| 461 | 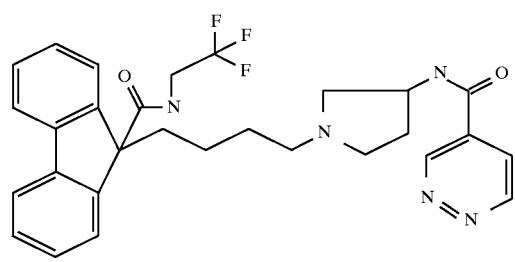 |
| 462 | 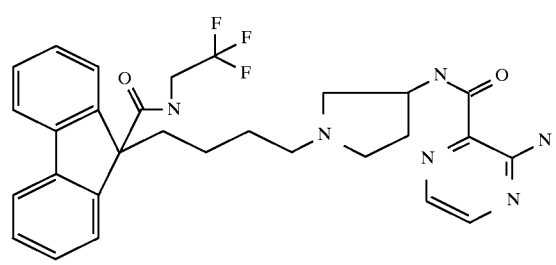 |
| 463 | 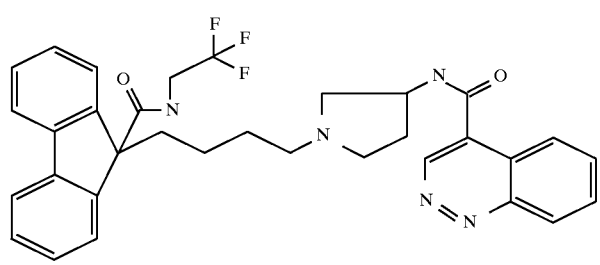 |

| Example No. | |
|---|---|
| 464 | 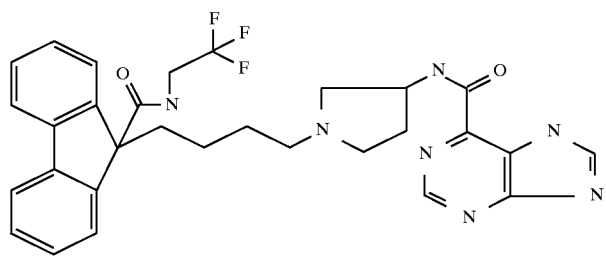 |
| 465 | 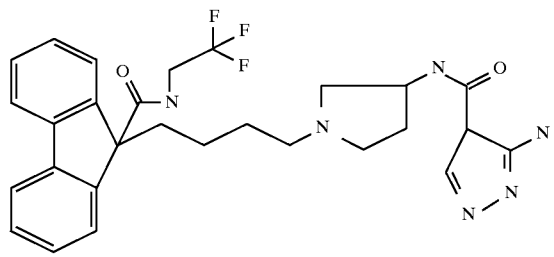 |
| 466 | 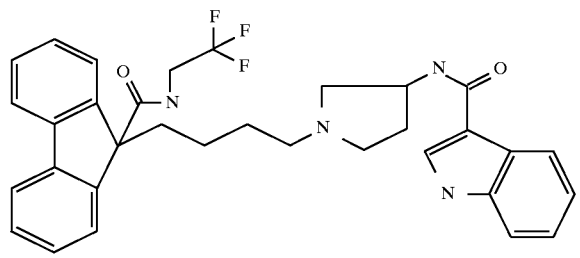 |
| 467 | 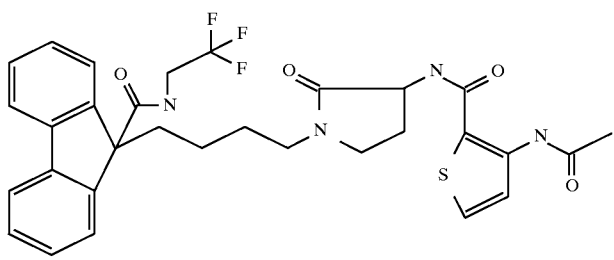 |
| 468 | 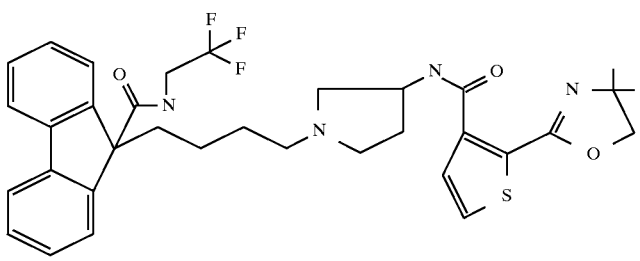 |
| 469 | 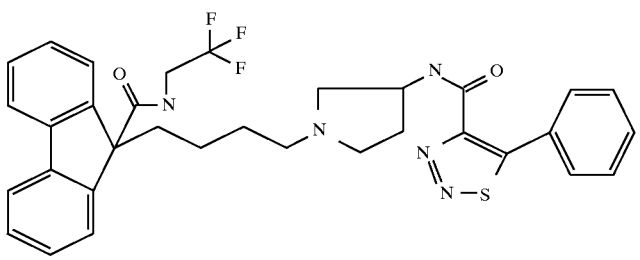 |

| Example No. | |
|---|---|
| 470 | 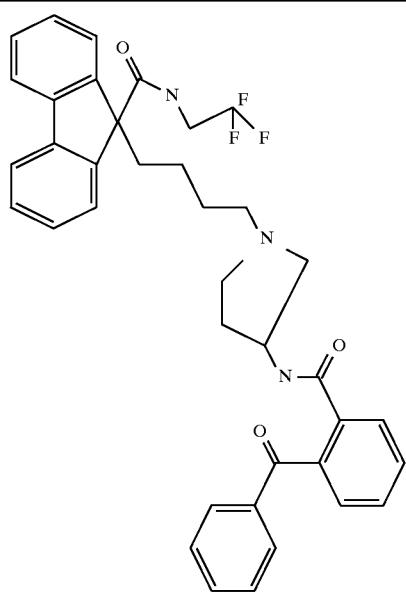 |
| 471 | 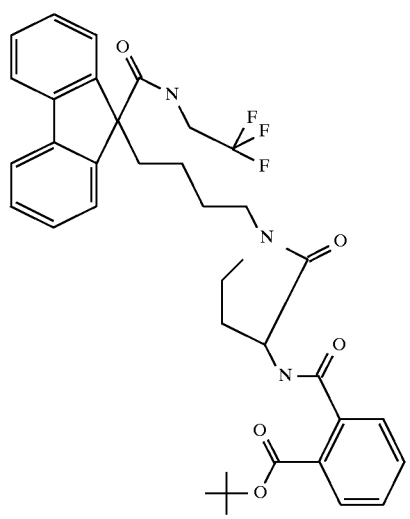 |
| 472 | 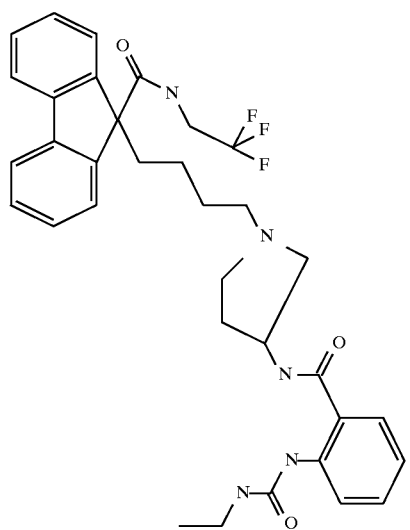 |

| Example No. | |
|---|---|
| 473 | 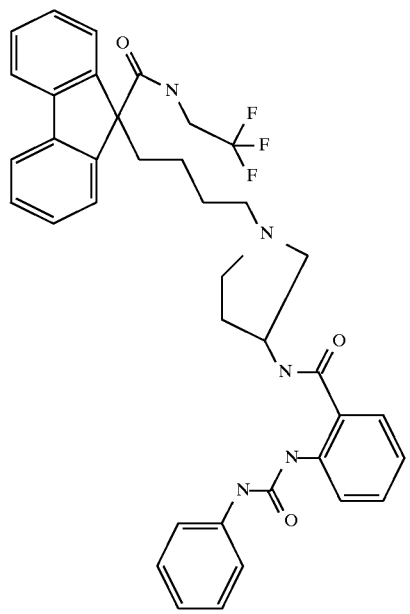 |
| 474 | 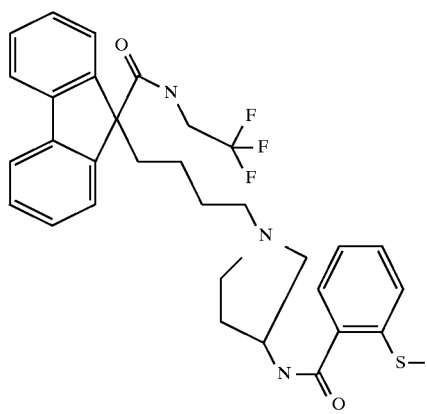 |
| 475 | 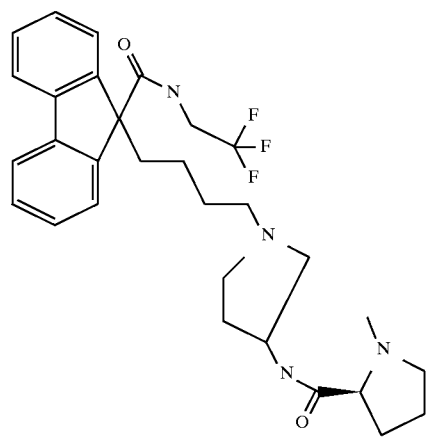 |

EXAMPLE 476

9-[4-[3-[(Phenoxycarbonyl)amino]-1-pyrrolidinyl]butyl]-N-(2,2,2-trifluoroethyl)-9H-fluorene-9-carboxamide, monohydrochloride

EXAMPLE 477

9-[4-[3-[[(Phenylamino)carbonyl]amino]-1-pyrrolidinyl]butyl]-N-(2,2,2-trifluoroethyl)-9H-fluorene-9-carboxamide, monohydrochloride

EXAMPLE 478

9-[4-[3-[(Phenylsulfonyl)amino]-1-pyrrolidinyl]butyl]-N-(2,2,2-trifluoroethyl)-9H-fluorene-9-carboxamide, monohydrochloride

EXAMPLE 479

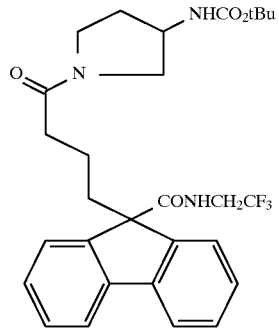

EXAMPLE 480 cis-9-[4-[3-[(2-Phenoxybenzoyl)amino]-1-pyrrolidinyl]butyl]-N-(2,2,2-trifluoroethyl)-9H-fluorene-9-carboxamide, N-oxide

EXAMPLE 481

9-[4-[3-[(2-Phenoxybenzoyl)amino]-1-pyrrolidinyl]-4-oxobutyl]-N-(2,2,2-trifluoroethyl)-9H-fluorene-9-carboxamide

EXAMPLE 482

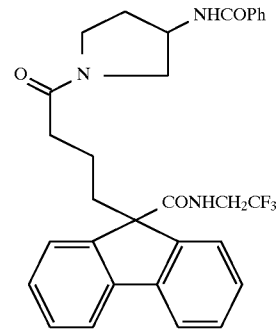

EXAMPLE 483

9-[4-[3-[[(1,1-Dimethylethoxy)carbonyl]amino]-1-pyrrolidinyl]pentyl]-N-(2,2,2-trifluoroethyl)-9H-fluorene-9-carboxamide

EXAMPLE 484

9-[4-[3-[[(2-Phenoxyphenyl)sulfonyl]amino]-1-pyrrolidinyl]butyl]-N-(2,2,2-trifluoroethyl)-9H-fluorene-9-carboxamide, monohydrochloride

EXAMPLE 485

[1-[[[2-[9-[[(2,2,2-Trifluoroethyl)amino)carbonyl]-9H-fluoren-9-yl]ethyl]amino]carbonyl]-3-pyrrolidinyl]carbamic acid, 1,1-dimethylethyl ester

EXAMPLE 486

9-[2-[[[3-(Benzoylamino)-1-pyrrolidinyl]carbonyl]amino]ethyl]-N-(2,2,2-trifluoroethyl)-9H-fluorene-9-carboxamide

EXAMPLE 487

3-[[(1,1-Dimethylethoxy)carbonyl]amino]-1-pyrrolidinecarboxylic acid, 2-[9-[[(2,2,2-trifluoroethyl)amino]carbonyl]-9H-fluoren-9-yl], ethyl ester

EXAMPLE 488

3-[(2-Phenoxybenzoyl)amino]-1-pyrrolidinecarboxylic acid, 2-[9-[[(2,2,2-trifluoroethyl)amino]carbonyl]-9H-fluoren-9-yl]ethyl ester

EXAMPLE 489

9-[4-[3-[(2-Phenoxybenzoyl)amino]-1-pyrrolidinyl]pentyl]-N-(2,2,2-trifluoroethyl)-9H-fluorene-9-carboxamide, monohydrochloride

EXAMPLE 490

9-[2-[[[3-[(2-Phenoxybenzoyl)amino]-1-pyrrolidinyl]carbonyl]amino]ethyl]-N-(2,2,2-trifluoroethyl)-9H-fluorene-9-carboxamide

EXAMPLE 491

3-(Benzoylamino)-1-pyrrolidinecarboxylic acid, 2-[9-[[(2,2,2-trifluoroethyl)amino]carbonyl]-9H-fluoren-9-yl]ethyl ester

EXAMPLE 492

9-[4-[3-(Benzoylamino)-1-pyrrolidinyl]pentyl]-N-(2,2,2-trifluoroethyl)-9H-fluorene-9-carboxamide, monohydrochloride

EXAMPLE 493

9-[4-[3-[[(1,1-Dimethylethoxy)carbonyl]amino]-1-pyrrolidinyl]butyl]-N-(2,2,2-trifluoroethyl)-9H-thioxanthene-9-carboxamide

EXAMPLE 494

9-[4-[3-(Benzoylamino)-1-pyrrolidinyl]-butyl]-N-(2,2,2-trifluoroethyl)-9H-thioxanthene-9-carboxamide

EXAMPLE 495

9-[4-[3-[[(2-Phenoxyphenyl)carbonyl]amino]-1-pyrrolidinyl]butyl]-N-(2,2,2-trifluoroethyl)-9H-thioxanthene-9-carboxamide

EXAMPLE 496

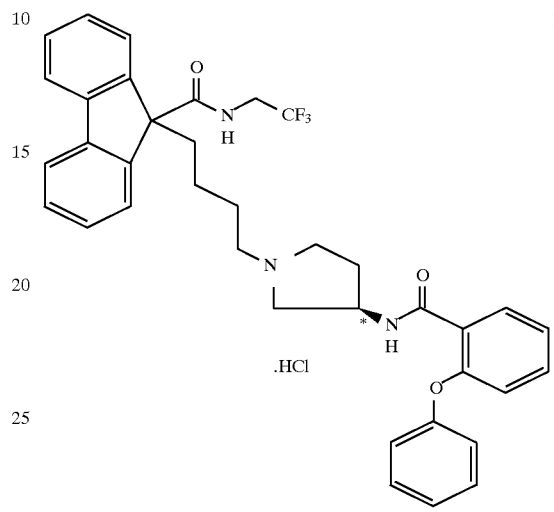

(R)-9-[4-[3-[(2-Phenoxybenzoyl)amino]-1-pyrrolidinyl]butyl]-N-(2,2,2-trifluoroethyl)-9H-fluorene-9-carboxamide, monohydrochloride.

m.p. 112°–115° C. MS (ES, +ions): m/z 628 (M+H) Anal. Calcd for $C_{37}H_{36}F_3N_3O_3+1.0$ HCl+0.9 $H_2O$: C, 65.32; H, 5.75; N, 6.18; F, 8.38; Cl, 5.21 Found: C, 65.30; H, 5.59; N, 6.01; F, 8.83; Cl, 5.35.

EXAMPLE 497

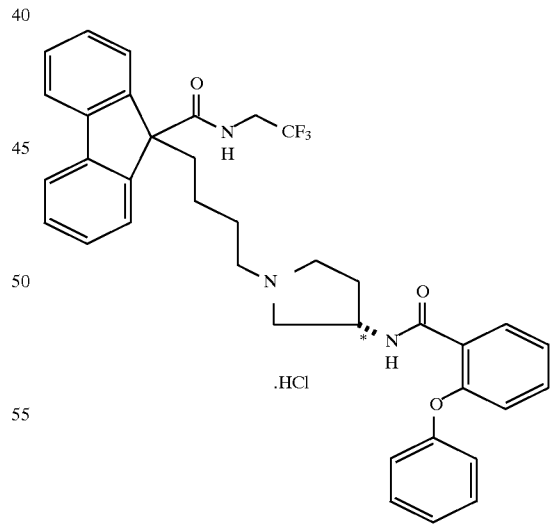

(S)-9-[4-[3-[(2-Phenoxybenzoyl)amino]-1-pyrrolidinyl]butyl]-N-(2,2,2-trifluoroethyl)-9H-fluorene-9-carboxamide, m.p. 98°–103° C. MS (ES, +ions): m/z 628 (M+H). Anal. Calcd for $C_{37}H_{36}F_3N_3O_3+1.0$ HCl+1.5 $H_2O$: C, 64.30; H, 5.83; N, 6.08; F, 8.25 Found: C, 64.34; H, 5.63; N, 5.90; F, 8.46.

EXAMPLE 498

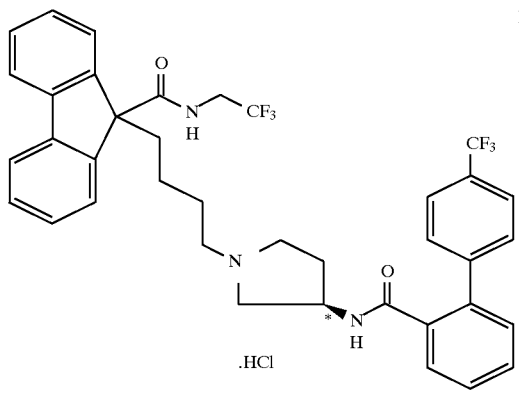

R isomer (R)-N-(2,2,2-Trifluoroethyl)-9-[4-[3-[[4'-(1,1,1-trifluoromethyl)[1,1'-biphenyl]-2-yl]carbonyl]amino]-1-pyrrolidinyl]butyl]-9H-fluorene-9-carboxamide, monohydrochloride.

m.p. 108°–112° C. MS (ES, +ions): m/z 680 (M+H) Anal. Calcd for $C_{38}H_{35}F_6N_3O_2+1.3$ HCl+2.1 $H_2O$: C, 59.67; H, 5.34; N, 5.49; Cl, 6.03 Found: C, 59.75; H, 5.00; N, 5.18; Cl, 5.75.

EXAMPLE 499

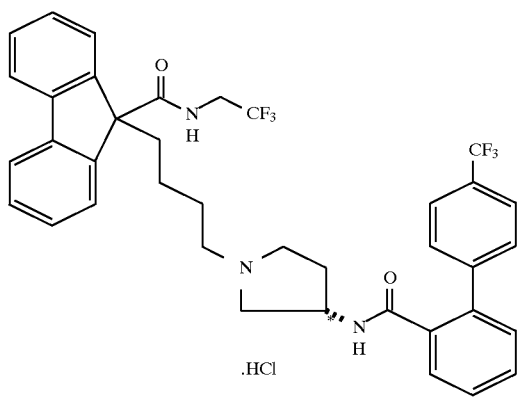

S isomer (S)-N-(2,2,2-Trifluoroethyl)-9-[4-[3-[[4'-(1,1,1-trifluoromethyl)[1,1'-biphenyl]- 2-yl]carbonyl]amino]-1-pyrrolidinyl]butyl]-9H-fluorene-9-carboxamide, monohydrochloride.

m.p. 101°–105° C. MS (ES, +ions): m/z 680 (M+H).

What is claimed is:

1. A compound which has the structure

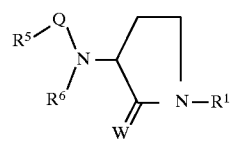

where Q is $-\overset{O}{\underset{\parallel}{C}}-$ or $-\overset{O}{\underset{\parallel}{\underset{O}{S}}}-$;

W is H,H or O;

$R^1$ is alkyl, alkenyl, alkynyl, aryl, heteroaryl, arylalkyl, diarylalkyl, arylalkenyl, diarylalkenyl, arylalkynyl, diarylalkynyl, diarylalkylaryl, heteroarylalkyl, cycloalkyl, or cycloalkylalkyl, all optionally substituted through available carbon atoms with 1, 2, 3 or 4 groups selected from halo, haloalkyl, alkyl, alkenyl, alkoxy, aryloxy, aryl, arylalkyl, alkylmercapto, arylmercapto, cycloalkyl, cyclo-alkylalkyl, heteroaryl, fluorenyl, heteroarylalkyl, hydroxy or oxo;

or $R^1$ is a fluorenyl-type group of the structure

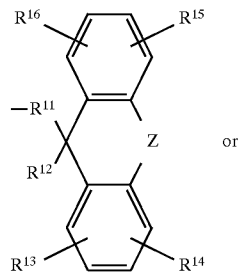  A

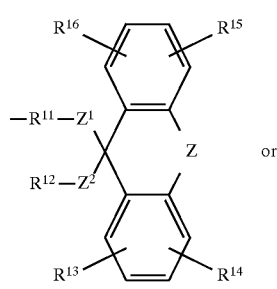  B

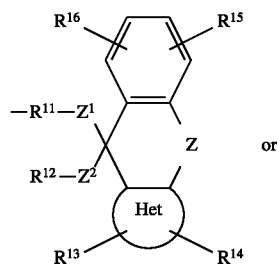  C

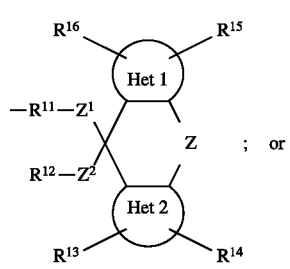  D $R^1$ is an indenyl-type group of the structure

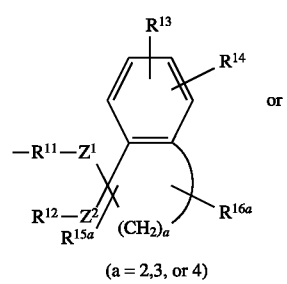  E (a = 2, 3, or 4)

-continued

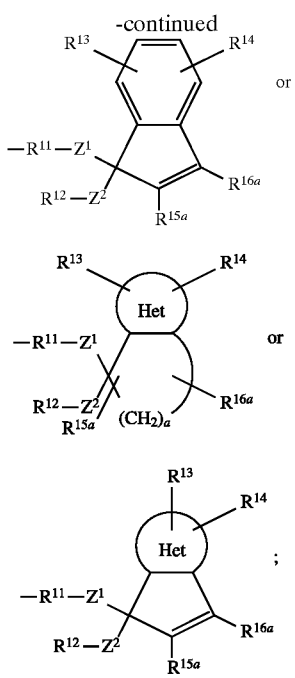

$Z^1$ and $Z^2$ are the same or different and are independently a bond, O, S,

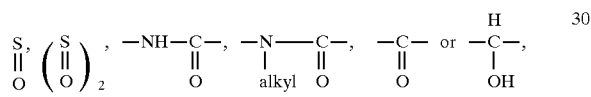

with the proviso that with respect to B, at least one of $Z^1$ and $Z^2$ will be other than a bond; $R^{11}$ is a bond, alkylene, alkenylene or alkynylene of up to 10 carbon atoms; arylene or mixed arylene-alkylene; $R^{12}$ is hydrogen, alkyl, alkenyl, aryl, haloalkyl, trihaloalkyl, trihaloalkylalkyl, heteroaryl, heteroarylalkyl, arylalkyl, arylalkenyl, cycloalkyl, aryloxy, alkoxy, arylalkoxy or cycloalkylalkyl, with the provisos that (1) when $R^{12}$ is H, aryloxy, alkoxy or arylalkoxy, then $Z^2$ is

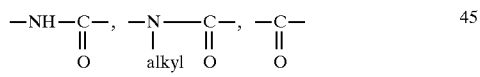

or a bond and (2) when $Z^2$ is a bond, $R^{12}$ cannot be heteroaryl or heteroarylalkyl;

Z is a bond, O, S, N-alkyl, N-aryl, or alkylene or alkenylene from 1 to 5 carbon atoms; $R^{13}$, $R^{14}$, $R^{15}$, and $R^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl or aryloxy;

$R^{15a}$ and $R^{16a}$ are independently hydrogen, alkyl, halo, haloalkyl, aryl, cycloalkyl, cycloheteroalkyl, alkenyl, alkynyl, alkoxy, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl, or aryloxy;

or $R^1$ is a group of the structure

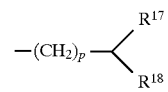

wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl at least one of $R^{17}$ and $R^{18}$ being other than H;

or $R^1$ is a group of the structure

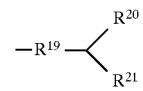

wherein $R^{19}$ is aryl or heteroaryl;

$R^{20}$ is aryl or heteroaryl;

$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;

$R^5$ is independently alkyl, alkenyl, alkynyl, aryl, alkoxy, aryloxy, arylalkoxy, heteroaryl, arylalkyl, heteroarylalkyl, cycloalkyl, cycloalkylalkyl, polycycloalkyl, polycycloalkylalkyl, cycloalkenyl, cycloheteroalkyl, heteroaryloxy, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino thiol, alkylthio, arylthio, heteroarylthio, arylthioalkyl, alkylcarbonyl, arylcarbonyl, arylaminocarbonyl, alkoxycarbonyl aminocarbonyl, alkynyl-aminocarbonyl, alkylaminocarbonyl, alkenyl-aminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, alkylsulfinyl;

$R^6$ is hydrogen or $C_1$–$C_4$ alkyl or $C_1$–$C_4$ alkenyl; all optionally substituted with 1, 2, 3 or 4 groups which may independently be any of the substituents listed in the definition of $R^5$ set out above;

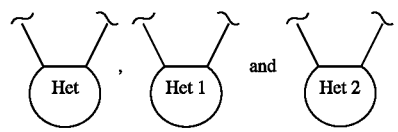

are the same or different and are independently selected from heteroaryl containing 5- or 6-ring members; and an N-oxide

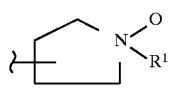

thereof; stereoisomers thereof; and a pharmaceutically acceptable salt thereof, with the proviso that when $R^5$ is aryl, then $R^1$ is other than cycloalkyl, phenyl and phenyllower alkyl.

2. The compound as defined in claim 1 having the formula

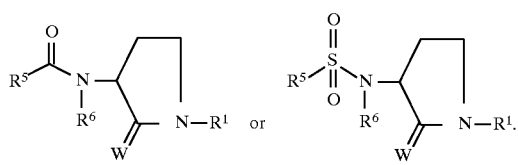

3. The compound as defined in claim 1 having the formula

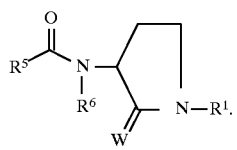

4. The compound as defined in claim 1 wherein $R^1$ is

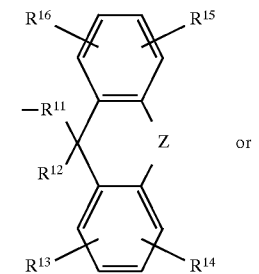   A

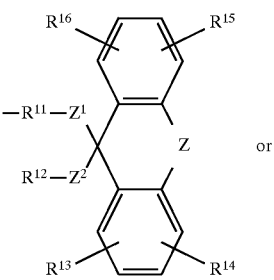   B

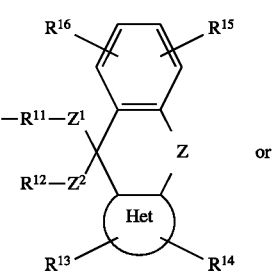   C

-continued

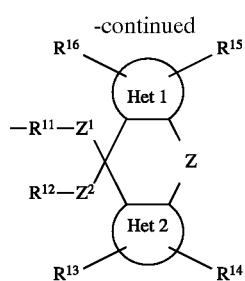   D

5. The compound as defined in claim 4 wherein $R^1$ is

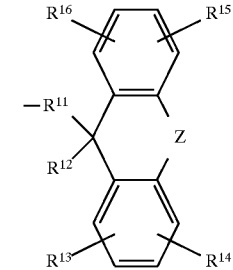   A or

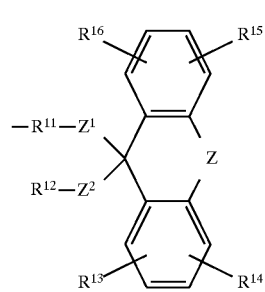   B

Z is a bond, O or S;

$R^{13}$, $R^{14}$, $R^{15}$ and $R^{16}$ are each H or one of $R^{15}$ and $R^{16}$ and one of $R^{13}$ and $R^{14}$ are halogen;

$Z^1$ is a bond or C=O;

$R^{11}$ is alkylene or alkenylene;

$R^{12}$-$Z^2$ is

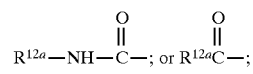

$R^{12a}$ is alkyl, fluorinated lower alkyl or polyfluorinated lower alkyl.

6. The compound as defined in claim 1 wherein $R^1$ is arylalkyl, arylalkenyl, heteroarylalkyl, heteroarylalkenyl,

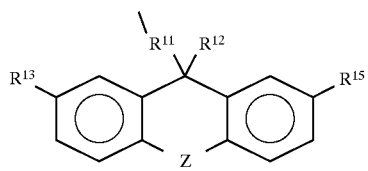

where $R^{11}$ is alkylene or alkenylene; $R^{12}$ is H, alkyl, alkenyl, aralkyl, aralkenyl; and $R^{13}$ is H or F; and $R^{15}$ is H or F; Z is O, S or a bond; or $R^1$ is

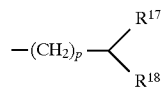

wherein $(CH_2)_p$ represents an alkylene chain or cis alkenylene of up to 6 carbons;

$R^{17}$ and $R^{18}$ are each independently alkyl, alkenyl, aryl, arylalkyl, heteroaryl, heteroarylalkyl, cycloalkyl, cycloalkylalkyl; or $R^1$ is

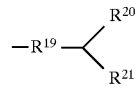

$R^{19}$ is aryl or heteroaryl; $R^{20}$ is aryl or heteroaryl;

$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl, or cycloalkylalkoxy.

7. The compound as defined in claim 1 wherein $R^1$ is an indenyl-type group of the structure

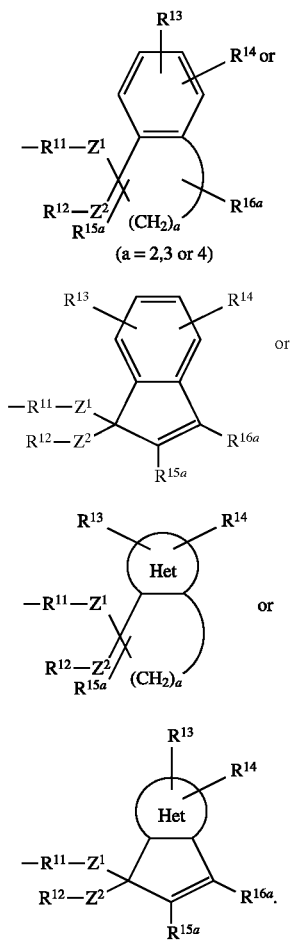

8. The compound as defined in claim 1 having the structrure

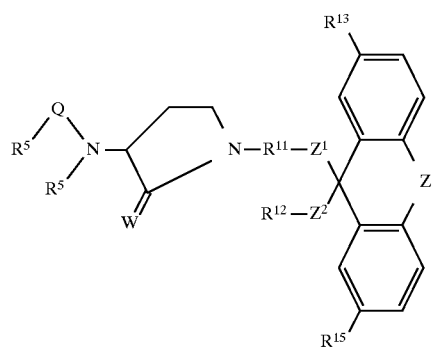

where Q is $-\overset{O}{\underset{\|}{C}}-$ or $-\overset{O}{\underset{\|}{\underset{O}{S}}}-$ ;

Z is a bond, O or S;

where $R^5$ is cycloalkyl, phenyl, aryl, heteroaryl, or cycloalkyl, phenyl, aryl or heteroaryl, independently substituted at the ortho position with alkyl, alkoxy, haloalkyl (optionally substituted with up to 5 halogens), trifluoromethyl, aryl, aryloxy, haloalkoxy (optionally substituted with up to 5 halogens), arylalkyl or arylalkoxy;

$R^6$ is H or $CH_3$;

$R^{13}$ and $R^{15}$ are independently H or F;

$Z^1$ is a bond;

$R^{11}$ is alkylene;

$R^{12}$-$Z^2$ is

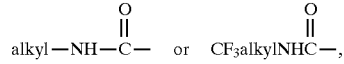

or $Z^2$ is a bond and $R^{12}$ is alkyl.

9. The compound as defined in claim 8 wherein $R^{11}$ is $-(CH_2)_4-$, $Z^1$ is a bond, and $R^{12}$-$Z^2$ is

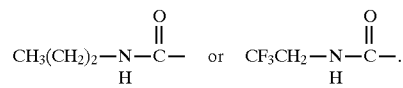

10. The compound as defined in claim 8 having the structure

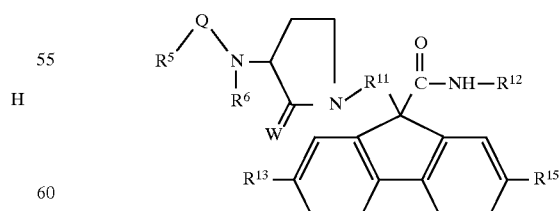

and $R^{12}$ is trifluoromethylalkyl or alkyl.

11. The compound as defined in claim 8 having the structure

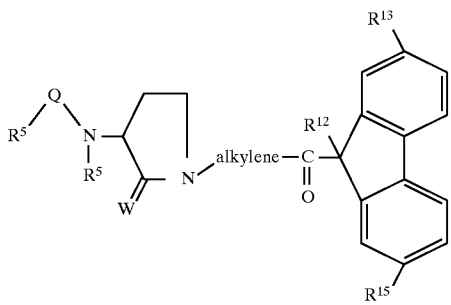

where $R^{12}$ is alkyl.

12. The compound as defined in claim 1 wherein $R^1$ is a group of the structure

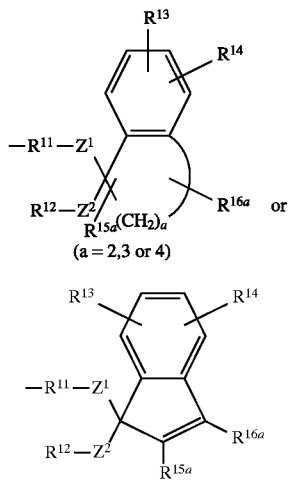

13. The compound as defined in claim 1 having the structrure

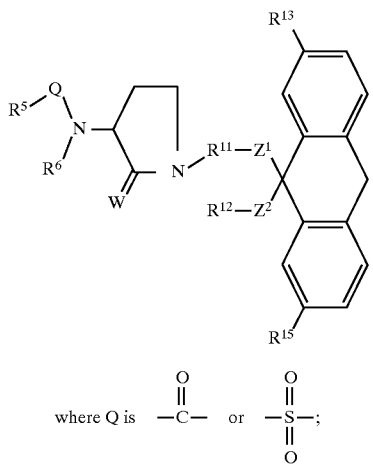

where Q is —C— or —S—;

Z is a bond, O or S;

where $R^5$ is cycloalkyl, phenyl, aryl, heteroaryl, or cycloalkyl, phenyl, aryl or heteroaryl, independently substituted at the ortho position with alkyl, alkoxy, haloalkyl (optionally substituted with up to 5 halogens), trifluoromethyl, aryl, aryloxy, haloalkoxy (optionally substituted with up to 5 halogens), arylalkyl or arylalkoxy;

$R^6$ is H or $CH_3$;

$R^{13}$ and $R^{15}$ are independently H or F;

$Z^1$ is a bond;

$R^{11}$ is alkylene;

$R^{12}$-$Z^2$ is

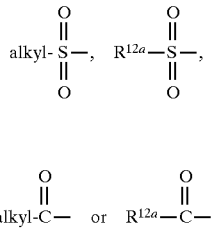

$R^{12a}$ is alkyl, fluorinated lower alkyl or polyfluorinated lower alkyl, or $Z^2$ is a bond and $R^{12}$ is alkyl.

14. The compound as defined in claim 1 which is
9-[4-[3-[(2-phenoxybenzoyl)amino]-1-pyrrolidinyl]butyl]-N-(2,2,2-trifluoroethyl)-9H-fluorene-9-carboxamide, 9-[4-[3-(benzoylamino)-1-pyrrolidinyl]-butyl]-N-(2,2,2-trifluoroethyl)-9H-fluorene-9-carboxamide, (R)-9-[4-[3-[(2-phenoxybenzoyl)amino]-1-pyrrolidinyl]butyl]-N-(2,2,2-trifluoroethyl)-9H-fluorene-9-carboxamide, (S)-9-[4-[3-[(2-phenoxybenzoyl)amino]-1-pyrrolidinyl]butyl]-N-(2,2,2-trifluoroethyl)-9H-fluorene-9-carboxamide, (R)-N-(2,2,2-trifluoroethyl)-9-[4-[3-[[4'-(1,1,1-trifluoromethyl)[1,1'-biphenyl]-2-yl]carbonyl]amino]-1-pyrrolidinyl]butyl]-9H-fluorene-9-carboxamide, (S)-N-(2,2,2-trifluoroethyl)-9-[4-[3-[[4'-(1,1,1-trifluoromethyl)[1,1'-biphenyl]-2-yl]carbonyl]amino]-1-pyrrolidinyl]butyl]-9H-fluorene-9-carboxamide, 9-[4-[2-oxo-3-[[[4'-(trifluoromethyl)[1,1'-biphenyl]-2-yl]carbonyl]amino]-1-pyrrolidinyl]butyl]-N-(2,2,2-trifluoroethyl)-9H-fluorene-9-carboxamide, 9-[4-[3-[[2-(2-benzothiazolyl)benzoyl]amino]-2-oxo-1-pyrrolidinyl]butyl]-N-(2,2,2-trifluoroethyl)-9H-fluorene-9-carboxamide, 9-[4-[2-oxo-3-[(2-phenoxybenzoyl)amino]-1-pyrrolidinyl]butyl]-N-(2,2,2-trifluoroethyl)-9H-fluorene-9-carboxamide, 9-[4-[3-(benzoylamino)-2-oxo-1-pyrrolidinyl]butyl]-N-(2,2,2-trifluoroethyl)-9H-fluorene-9-carboxamide, 9-[4-[2-oxo-3-[[2-(2-pyridinyl)benzoyl]amino]-1-pyrrolidinyl]butyl]-N-(2,2,2-trifluoroethyl)-9H-fluorene-9-carboxamide, or 9-[4-[3-[[2-(4-morpholinyl)benzoyl]amino]-2-1-pyrrolidinyl]butyl]-N-(2,2,2-trifluoroethyl)-9H-fluorene-9-carboxamide, or a pharmaceutically acceptable salt thereof.

15. A method for preventing, inhibiting or treating atherosclerosis in a mammalian species, which comprises administering to a patient in need of treatment a therapeutically effective amount of a compound as defined in claim 1.

16. A method of lowering serum lipid levels, cholesterol and/or triglycerides, or inhibiting and/or treating hyperlipemia, hyperlipidemia, hyperlipoproteinemia, hypercholesterolemia and/or hypertriglyceridemia, which comprises administering to a patient in need of treatment a therapeutically effective amount of a compound as defined in claim 1.

* * * * *